US010562973B2

(12) United States Patent
Barbour et al.

(10) Patent No.: US 10,562,973 B2
(45) Date of Patent: Feb. 18, 2020

(54) BLOOD-BRAIN BARRIER SHUTTLES CONTAINING ANTIBODIES RECOGNIZING ALPHA-SYNUCLEIN

(71) Applicants: Prothena Bioscience Limited, Dublin (IE); Hoffmann-La Roche Inc., Little Falls, NJ (US)

(72) Inventors: Robin Barbour, Walnut Creek, CA (US); Kate Dora Games-Thiel, Belmont, CA (US); Tarlochan S. Niijar, Orinda, CA (US); Wagner Zago, San Mateo, CA (US); Olaf Mundigl, Weilheim (DE); Jens Niewoehner, Munich (DE); Georg Tiefenthaler, Sindelsdorf (DE)

(73) Assignees: Prothena Bioscience Limited, Dublin (IE); Hoffmann-LaRoche Inc., Little Falls, NJ (US)

( * ) Notice: Subject to any disclaimer, the term of this patent is extended or adjusted under 35 U.S.C. 154(b) by 4 days.

(21) Appl. No.: 15/129,676

(22) PCT Filed: Apr. 8, 2015

(86) PCT No.: PCT/IB2015/052524
§ 371 (c)(1),
(2) Date: Sep. 27, 2016

(87) PCT Pub. No.: WO2015/155694
PCT Pub. Date: Oct. 15, 2015

(65) Prior Publication Data
US 2017/0174777 A1   Jun. 22, 2017

Related U.S. Application Data

(60) Provisional application No. 62/023,373, filed on Jul. 11, 2014, provisional application No. 61/977,042, filed on Apr. 8, 2014, provisional application No. 61/977,039, filed on Apr. 8, 2014.

(51) Int. Cl.
*C07K 16/18* (2006.01)
*C07K 16/28* (2006.01)
*C12N 5/12* (2006.01)
*G01N 33/68* (2006.01)

(52) U.S. Cl.
CPC .......... *C07K 16/2881* (2013.01); *C07K 16/18* (2013.01); *C07K 16/28* (2013.01); *C12N 5/12* (2013.01); *G01N 33/6896* (2013.01); *C07K 2317/24* (2013.01); *C07K 2317/34* (2013.01); *C07K 2317/35* (2013.01); *C07K 2317/51* (2013.01); *C07K 2317/515* (2013.01); *C07K 2317/52* (2013.01); *C07K 2317/524* (2013.01); *C07K 2317/526* (2013.01); *C07K 2317/55* (2013.01); *C07K 2317/56* (2013.01); *C07K 2317/565* (2013.01); *C07K 2317/76* (2013.01); *C07K 2317/92* (2013.01); *C07K 2319/33* (2013.01); *C07K 2319/74* (2013.01); *C12N 2510/02* (2013.01); *G01N 2333/47* (2013.01); *G01N 2800/28* (2013.01); *G01N 2800/50* (2013.01)

(58) Field of Classification Search
CPC ................ A61K 49/0058; A61K 49/16; A61K 51/1018; A61K 47/6849
See application file for complete search history.

(56) References Cited

U.S. PATENT DOCUMENTS

| | | |
|---|---|---|
| 4,252,906 A | 2/1981 | Hosokawa et al. |
| 4,476,297 A | 10/1984 | Glass et al. |
| 4,634,664 A | 1/1987 | Oestberg |
| 4,634,666 A | 1/1987 | Engleman et al. |
| 5,208,020 A | 5/1993 | Chari et al. |
| 5,208,362 A | 5/1993 | Glass et al. |
| 5,209,485 A | 5/1993 | Nesbitt et al. |
| 5,225,539 A | 7/1993 | Winter |
| 5,304,489 A | 4/1994 | Rosen |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,733,743 A | 3/1998 | Johnson et al. |
| 5,741,957 A | 4/1998 | Deboer et al. |
| 5,770,429 A | 6/1998 | Lonberg et al. |
| 5,786,464 A | 7/1998 | Seed |
| 5,789,650 A | 8/1998 | Lonberg et al. |
| 5,814,318 A | 9/1998 | Lonberg et al. |
| 5,834,597 A | 10/1998 | Tso et al. |
| 5,837,242 A | 11/1998 | Holliger et al. |
| 5,849,992 A | 12/1998 | Meade et al. |

(Continued)

FOREIGN PATENT DOCUMENTS

| | | |
|---|---|---|
| JP | 2006089637 | 4/2006 |
| WO | 1991/10741 | 7/1991 |

(Continued)

OTHER PUBLICATIONS

Ruoppila et al., "Cognitive Functioning of 75-and 80-year-old People and Changes During a 5-year Follow-Up." Scandinavian Journal of Social Medicine, Supplementum 53, 1997, pp. 44-65.

(Continued)

*Primary Examiner* — Robert C Hayes
(74) *Attorney, Agent, or Firm* — McDonnell Boehnen Hulbert & Berghoff LLP

(57) ABSTRACT

The invention provides blood-brain barrier shuttles comprising monoclonal antibody 5C1 and related antibodies linked to a monovalent binding entity for a blood-brain barrier receptor. The 5C1 antibody binds to an epitope within residues 118-126 of alpha-synuclein. The antibodies are useful, for example, for treating and/or diagnosing synucleinopathies including Lewy body diseases, such as Parkinson's disease, diffuse Lewy body disease (DLBD), Lewy body variant of Alzheimer's disease (LBV), Alzheimer's and Parkinson's disease comorbidity, and pure autonomic failure, as well as multiple system atrophy (MSA).

40 Claims, 13 Drawing Sheets

Specification includes a Sequence Listing.

(56) References Cited

U.S. PATENT DOCUMENTS

| | | | |
|---|---|---|---|
| 5,858,657 | A | 1/1999 | Winter et al. |
| 5,859,205 | A | 1/1999 | Adair et al. |
| 5,871,907 | A | 2/1999 | Winter et al. |
| 5,874,299 | A | 2/1999 | Lonberg et al. |
| 5,877,218 | A | 3/1999 | Herzig et al. |
| 5,877,397 | A | 3/1999 | Lonberg et al. |
| 5,888,809 | A | 3/1999 | Allison |
| 6,063,598 | A | 5/2000 | Enekel et al. |
| 6,114,148 | A | 9/2000 | Seed et al. |
| 6,407,213 | B1 | 6/2002 | Carter et al. |
| 6,583,190 | B2 | 6/2003 | Lee et al. |
| 6,624,821 | B1 | 9/2003 | Shin et al. |
| 6,719,971 | B1 | 4/2004 | Carter et al. |
| 6,720,364 | B2 | 4/2004 | Sueda et al. |
| 6,881,557 | B2 | 4/2005 | Foote |
| 7,022,500 | B1 | 4/2006 | Queen et al. |
| 7,179,873 | B2 | 2/2007 | Reimers et al. |
| 7,358,331 | B2 | 4/2008 | Chilcote et al. |
| 7,566,771 | B1 | 7/2009 | Adair et al. |
| 7,569,339 | B2 | 8/2009 | Kaufmann et al. |
| 7,657,380 | B2 | 2/2010 | Lazar et al. |
| 7,674,599 | B2 | 3/2010 | Chilcote et al. |
| 7,910,333 | B2 | 3/2011 | Chilcote et al. |
| 7,919,088 | B2 | 4/2011 | Schenk et al. |
| 8,092,801 | B2 | 1/2012 | Schenk et al. |
| 8,609,820 | B2 | 12/2013 | Saldanha et al. |
| 8,790,644 | B2 | 7/2014 | Saldanha et al. |
| 9,217,030 | B2 | 12/2015 | Saldanha et al. |
| 9,234,031 | B2 | 1/2016 | Saldanha et al. |
| 2002/0077379 | A1 | 6/2002 | Hughes et al. |
| 2005/0009150 | A1 | 1/2005 | Basi et al. |
| 2005/0147613 | A1 | 7/2005 | Raso et al. |
| 2008/0014194 | A1 | 1/2008 | Schenk et al. |
| 2009/0010924 | A1 | 1/2009 | Wu et al. |
| 2009/0202432 | A1 | 8/2009 | Schenk et al. |
| 2009/0208487 | A1 | 8/2009 | Schenk et al. |
| 2010/0031377 | A1 | 2/2010 | Schenk et al. |
| 2010/0035763 | A1 | 2/2010 | Chen et al. |
| 2010/0081796 | A1 | 4/2010 | Brinkmann et al. |
| 2010/0099103 | A1 | 4/2010 | Hsieh et al. |
| 2010/0151471 | A1 | 6/2010 | Faham et al. |
| 2010/0203631 | A1 | 8/2010 | Chilcote et al. |
| 2010/0256338 | A1 | 10/2010 | Brinkmann et al. |
| 2010/0291066 | A1 | 11/2010 | Horowitz et al. |
| 2011/0052498 | A1 | 3/2011 | Lannfelt et al. |
| 2011/0053803 | A1 | 3/2011 | Xin et al. |
| 2012/0204275 | A1 | 8/2012 | Schenk et al. |
| 2012/0220730 | A1 | 8/2012 | Li et al. |
| 2012/0276019 | A1 | 11/2012 | Charles et al. |
| 2013/0053496 | A1 | 2/2013 | Austin et al. |
| 2013/0137824 | A1 | 5/2013 | Gray et al. |
| 2014/0127131 | A1 | 5/2014 | Barbour et al. |
| 2014/0275495 | A1 | 9/2014 | Saldanha et al. |
| 2015/0024433 | A1 | 1/2015 | Saldanha et al. |
| 2015/0056187 | A1 | 2/2015 | Saldanha et al. |
| 2015/0079074 | A1 | 3/2015 | Garidel et al. |
| 2015/0259404 | A1 | 9/2015 | Barbour et al. |

FOREIGN PATENT DOCUMENTS

| | | |
|---|---|---|
| WO | 1991/17271 | 11/1991 |
| WO | 1992/01047 | 1/1992 |
| WO | 1993/01222 | 1/1993 |
| WO | 1994/04678 | 3/1994 |
| WO | 2004/039234 | 5/2004 |
| WO | 2004/041067 | 5/2004 |
| WO | 2004/050884 | 6/2004 |
| WO | 2005/019442 | 3/2005 |
| WO | 2005/047860 | 5/2005 |
| WO | 2007/011907 | 1/2007 |
| WO | 2007/068429 | 6/2007 |
| WO | 2008/011348 | 1/2008 |
| WO | 2008/012142 | 1/2008 |
| WO | 2008/103472 | 8/2008 |
| WO | 2008/103473 | 8/2008 |
| WO | 2008/107388 | 9/2008 |
| WO | 2008/116103 | 9/2008 |
| WO | 2009/027471 | 3/2009 |
| WO | 2010/031377 | 3/2010 |
| WO | 2010/069603 | 6/2010 |
| WO | 2011/090720 | 7/2011 |
| WO | 2013/066866 | 5/2012 |
| WO | 2012/075037 | 6/2012 |
| WO | 2012/160536 | 11/2012 |
| WO | 2012/174568 | 12/2012 |
| WO | 2012/177997 | 12/2012 |
| WO | 2013/063516 | 5/2013 |
| WO | 2013/112945 | 8/2013 |
| WO | 2014/033074 | 3/2014 |
| WO | 2014/039234 | 3/2014 |
| WO | 2014/058924 | 4/2014 |
| WO | 2015/001504 | 1/2015 |

OTHER PUBLICATIONS

Schneider et al., "Primary structure of human transferrin receptor deduced from the mRNA sequence," Nature, 1984, pp. 675-678, vol. 311, No. 5987.

Songsivilai et al., "Bispecific antibody: a tool for diagnosis and treatment of disease," Clin. Exp. Immunol., 1990, pp. 315-321, vol. 79.

Spillantini et al., "α Synuclein in Lewy Bodies," Nature, 1997, pp. 839-840, vol. 388.

Takeda et al., "Abnormal Accumulation of α-Synuclein in Neurodegenerative Discorders," American Journal of Pathology, Feb. 1998, pp. 367-372, vol. 152, No. 2.

Tamura et al., "Structural Correlates of an Anticarcinoma Antibody: Identification of Specificity-Determining Residues (SDRs) and Development of a Minimally Immunogenic Antibody Variant by Retention of SDRs Only," Journal of Immunology, 2000, pp. 1432-1441, vol. 164.

Uéda et al., "Molecular cloning of cDNA encoding an unrecognized component of amyloid in Alzheimer disease," Proc. Natl. Acad. Sci. USA, Dec. 1993, pp. 11282-11286, vol. 90.

UniProtKB Accession No. P06213, "INSR_HUMAN," Jul. 2017, 23 pages.

UniProtKB Accession No. P08069, "IGF1R_HUMAN," Jun. 7, 2017, 15 pages.

UniProtKB Accession No. Q07954, "LRP1_HUMAN," Jul. 5, 2017, 27 pages.

UniProtKB Accession No. Q14114, "LRP8_HUMAN," Jul. 5, 2017, 13 pages.

UniProtKB Accession No. Q99075, "HBEGF_HUMAN," Jun. 7, 2017, 8 pages.

UniProtKB Accession No. P02786, "TFR1_HUMAN," Jun. 7, 2017, 12 pages.

Vajdos et al., "Comprehensive Functional Maps of the Antigenbinding Site of an Anti-ErbB2 Antibody Obtained with Shotgun Scanning Mutagenesis," J. Mol. Biol., 2002, pp. 415-528, vol. 320, No. 2.

Volles et al., "Zeroing in on the Pathogenic Form of α-Synuclein and its Mechanism of Neurotoxicity in Parkinson's Disease," Biochemistry, Jul. 8, 2003, pp. 7871-7878, vol. 42, No. 26.

Wakabayashi et al., "NACP, a presynaptic protein, immunoreactivity in Lewy bodies in Parkinson's disease," Neuroscience Letters, 1997, pp. 45-48, vol. 239, No. 1.

Wang, Shixia, "Advances in the production of human monoclonal antibodies," Antibody Technology Journal, 2011, pp. 1-4, vol. 1.

Wang et al., "Antibody Structure, Instability, and Formulation," Journal of Pharmaceutical Sciences, Jan. 2007, pp. 1-26, vol. 96, No. 1.

Wang, Wei, "Instability, stabilization, and formulation of liquid protein pharmaceuticals," International Journal of Pharmaceutics, 1999, pp. 129-188, vol. 185.

Ward et al., "Binding activities of a repertoire of single immunoglobulin variable domains secreted from *Escherichia coli*," Nature, Oct. 12, 1989, pp. 544-546, vol. 341.

(56) References Cited

OTHER PUBLICATIONS

Warne, Nicholas W., "Development of high concentration protein biopharmaceuticals: The use of platform approaches in formulation development," European Journal of Pharmaceutics and Biopharmaceutics, 2011, pp. 208-211, vol. 78.

Yang et al., "Structural basis of immunosuppression by the therapeutic antibody daclizumab," Cell Research, 2010, pp. 1361-1371, vol. 20.

Yu et al., "Boosting Brain Uptake of a Therapeutic Antibody by Reducing its Affinity for a Transcytosis Target," Science Translational Medicine, 2011, 9 pages, vol. 3, Issue 84.

Zatsepin et al. "Covalent binding of modified nucleic acids to proteins as a method for investigation of specific protein—nucleic acid interactions," Russian Chemical Reviews, 2005, pp. 77-95, vol. 74, No. 1.

Choi et al., "Fine epitope mapping of monoclonal antibodies specific to human alpha-synuclein", Neuroscience Letters, 397:53-58 (2006).

Spiess et al., "Alternative molecular formats and therapeutic applications for bispecitic antibodies", Mol. Immol., 67:95-105 (2015).

Felgenhauer et al., "Protein size and cerebrospinal fluid composition", Klin. WSCHR, 52:1152-1164 (1974).

Kontermann et al., "Dual targeting strategies with bispecific antbodies", mAbs, 4(2):182-197 (Mar. 2012).

Padlan et al., "A possible procedure for reducing the immunogenicity of antibody variable domains while preserving their ligand-binding properties", Mol Immunol., 28(4-5):489-98 (Apr. 1991).

Atwal et al., "A Therapeutic Antibody Targeting BACE1 Inhibits Amyloid-β Production in Vivo," Science Translational Medicine, 2011, 15 pages, vol. 3, Issue 84.

Boado et al. "Engineering and expression of a chimeric transferrin receptor monoclonal antibody for blood-brain barrier delivery in the mouse." Biotechnology and Bioengineering, 2009, pp. 1251-1258, vol. 102, No. 4.

Carter et al., "'Knobs-into-holes' provides a rational design strategy for engineering antibody CH3 domains for heavy chain heterodimerization," Immunotechnology, 1996, p. 73, vol. 2, No. 1.

Chari et al., "Immunoconjugates containing novel maytansinoids: promising anticancer drugs," Cancer Research, 1992, pp. 127-131, vol. 52, No. 1.

Chothia et al., "Canonical Structures for the Hypervariable Regions of Immunoglobulins," J. Mol. Biol., 1987, pp. 901-917, vol. 196.

Chothia et al, "Conformations of immunoglobulin hypervariable regions," Nature, 1989, pp. 878-883, vol. 342.

Co et al., "Chimeric and Humanized Antibodies with Specificity for the CD33 Antigen," J. Immunol., Feb. 15, 1992, pp. 1149-1154, vol. 148.

Conway et al., "Acceleration of oligomerization, not fibrillization, is a shared property of both α-synuclein mutations linked to early-onset Parkinson's disease: implications for pathogenesis and therapy," Proceedings of the National Academy of Sciences, 2000, pp. 571-576, vol. 97, No. 2.

Daugherty et al., "Formulation and delivery issues for monoclonal antibody therapeutics," Advanced Drug Delivery Reviews, 2006, pp. 686-706, vol. 58.

De Pascalis et al., "Grafting of "abbreviated" complementarity-determining regions containing specificity-determining residues essential for ligand contact to engineer a less immunogenic humanized monoclonal antibody," The Journal of Immunology, 2002, pp. 3076-3084, vol. 169.

El-Agnaf et al., "α-Synuclein implicated in Parkinson's disease is present in extracellular biological fluids, including human plasma," The FASEB Journal, 2003, 17 pages.

Feany et al., "A Drosophila model of Parkinson's disease," Nature, 2000, pp. 394-398, vol. 404.

Finlay et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J. Mol. Biol., 2009, pp. 541-558, vol. 388.

Foote et al., "Antibody framework residues affecting the conformation of the hypervariable loops," Journal of Molecular Biology, 1992, 224.2, pp. 487-499, vol. 224, No. 2.

Friden et al., "Blood-brain Barrier Penetration and in Vivo Activity of an NGF Conjugate," Science, 1993, pp. 373-377, vol. 259, No. 5093.

Friden et al., "Anti-transferrin receptor antibody and antibody-drug conjugates cross the blood-brain barrier," Proc. Natl. Acad. Sci. USA, Jun. 1991, pp. 4771-4775, vol. 88.

Galasko et al. "Clinical-Neuropathological Correlations in Alzheimer's Disease and Related Dementias." Archives of Neurology, 1994, pp. 888-895, vol. 51, No. 9.

GenBank—PDB—accession No. 3NFP_A, "Chain A, Crystal Structure of the Fab Fragment of Therapeutic Antibody Daclizumab in Complex With Il-2ra (cd25) Ectodomain," Oct. 19, 2013, 3 pages.

GenBank accession No. AAC28255.1, "immunoglobulin kappa light chain, partial [Mus musculus]," Jul. 25, 2016, 2 pages.

GenBank accession No. AAF88044.1, "immunoglobulin heavy chain variable region, partial [Mus musculus]," Jul. 26, 2016, 2 pages.

GenBank—UniProtKB/Swiss-Prot. accession No. P37840, "RecName: Full=Alpha-synuclein: Full=Non-A beta component of AD amyloid; AltName: Full=Non-A4 component of amyloid precursor; Short= NACP," Jan. 18, 2017, 13 pages.

Greenspan et al., "Idiotypes: structure and immunogenicity," The FASEB Journal, 1993, pp. 437-444, vol. 7, No. 5.

Hackett Jr. et al., "Recombinant Mouse-Human Chimeric Antibodies as Caliborators in Immunoassays That Measure Antibodies to Toxoplasma gondii," Journal of Clinical Microbiology, May 1998, pp. 1277-1284, vol. 36, No. 5.

Hinton et al., "Engineered Human IgG Antibodies with Longer Serum Half-lives in Primates," J. Biol. Chem., 2004, pp. 6213, vol. 279.

Hust et al., "Single chain Fab (scFab) fragment," BMC Biotechnology, 2007, 15 pages, vol. 7, No. 14.

Iwahashi et al., "CDR substitutions of a humanized monoclonal antibody (CC49): contributions of individual CDRs to antigen binding and immunogenicity," Molecular Immunology, 1999, 1079-1091, vol. 36, No. 15.

Jensen et al., "Residues in the synuclein consensus motif of the α-synuclein fragment, NAC, participate in transglutaminase-catalysed cross-linking to Alzheimer-disease amyloid βA4 peptide," Biochemical Journal 310.1, 1995, pp. 91-94.

Junghans et al., "Anti-Tac-H, a humanized antibody to the interleukin 2 receptor with new features for Immunotherapy in malignant and immune disorders," Cancer Research, 1990, pp. 1495-1502, vol. 50, No. 5.

Kashmiri et al., "SDR grafting—a new approach to antibody humanization," Methods, 2005, pp. 25-34, vol. 36, No. 1.

Kostelny et al., "Formation of a Bispecitic Antibody by the Use of Leucine Zippers," The Journal of Immunology, Mar. 1, 1992, pp. 1547-1553, vol. 148, No. 5.

Kruger et al., "AlaSOPro mutation in the gene encoding α-synuclein in Parkinson's disease," Nature Gen., 1998, pp. 106-108, vol. 18.

Lazar et al., "Engineered antibody Fc variants with enhanced effector function," Proc. Natl Acad Sci USA, Mar. 14, 2006, pp. 4005-4010, vol. 103, No. 11.

Lewy Body Dementia Association ("LBDA"), "Incidence of Lewy Body Dementias in a General Population," http://www.lbda.org/content/incidence-lewy-body-dementias-general- population, 2013, 3 pages.

Mahowald et al., "When and where do synucleinopathies begin?" Neurology, 2010, pp. 488-489, vol. 75, No. 6.

Martin et al., "Structural families in loops of homologous proteins: automatic classification, modelling and application to antibodies," Journal of Molecular Biology, 1996, pp. 800-815, vol. 263, No. 5.

Masliah et al., Passive Immunization Reduces Behavioral and Neuropathological Deficits in an Alpha-Synuclein Transgenic Model of Lewy Body Disease, PLOS ONE, Jan. 2011, 20 pages, vol. 6, No. 4.

(56) References Cited

OTHER PUBLICATIONS

Masliah et al., "Effects of α-Synuclein Immunization in a Mouse Model of Parkinson's Disease," Neuron, Jun. 16, 2005, pp. 857-868, vol. 46.

Masliah et al. "Dopaminergic Loss and Inclusion Body Formation in α-Synuclein Mice: Implications for Neurodegenerative Disorders," Science, 2000, pp. 1265-1269, vol. 287.

McKeith et al. "Consensus guidelines for the clinical and pathologic diagnosis of dementia with Lewy bodies (DLB) Report of the consortium on DLB international workshop," Neurology, Nov. 1996, pp. 1113-1124, vol. 47, No. 5.

Mihara et al., "CTLA4lg inhibits T cell-dependent B-cell maturation in murine systemic lupus erythematosus," The Journal of Clinical Investigation, Jul. 2000, pp. 91-101, vol. 106, No. 1.

Näsström et al., "Antibodies against Alphas-Synuclein Reduce Oligomerization in Living Cells," PLoS ONE, 10 pages, vol. 6, No. 10.

Niewoehner et al., "Increased Brain Penetration and Potency of a Therapeutic Antibody Using a Monovalent Molcular Shuttle," Neuro, Cell Press, US, Jan. 2014, pp. 49-60, vol. 81, No. 1.

Nisonoff, Alfred, "American Associate of Immunologist—Presidential Address 0 IDIOTYPES: Concepts and Applications," The Journal of Immunology, Oct. 15, 1991, pp. 2429-2438, vol. 147.

Oestberg et al., "Human x (Mouse x Human) Hybridomas Stably Producing Human Antibodies," Hybridoma, 1983, pp. 361-367, vol. 2, No. 4.

Polymeropoulos et al., "Mutation in the α-Synuclein Gene Identified in Families with Parkinson's Disease," Science, 1997, pp. 2045-2047, vol. 276.

Queen et al., "Cell-Type Specific Regulation of a K Immunoglobulin Gene by Promoter and Enhancer Elements," Immunological Reviews, 1986, pp. 49-68, vol. 89, No. 1.

Rae, Michael, "Unbinding the Mummies: Human Testing of Rejuvenation Biotechnology Targeting [alpha]-Synuclein Begins," SENS Research Foundation, Oct. 2013, 16 pages.

Reddy et al., "Monoclonal antibodies isolated without screening by analyzing the variable-gene repertoire of plasma cells," Nature Biotechnology, 2010, pp. 965-969, vol. 28, No. 9.

Ridgway et al., "'Knobs-into-holes' engineering of antibody CH3 domains for heavy chain heterodimerization," Protein Engineering, Design and Selection, 1996, pp. 617-621, vol. 9, No. 7.

5C1-VH

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m5C1VH | Q | V | Q | L | Q | Q | S | G | A | E | L | A | K | P | G | T | S | V | Q | M |

| Kabat Numbering | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| m5C1VH | S | C | K | A | S | G | Y | T | F | T | N | Y | W | M | N | W | I | K | A | R |

| Kabat Numbering | 41 | 42 | 43 | 44 | 45 | 46 | 47 | 48 | 49 | 50 | 51 | 52 | 52A | 53 | 54 | 55 | 56 | 57 | 58 | 59 |
|---|---|---|---|---|---|---|---|---|---|---|---|---|---|---|---|---|---|---|---|---|
| m5C1VH | P | G | Q | G | L | E | W | I | G | A | T | N | P | N | N | G | Y | T | D | Y |

| Kabat Numbering | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|
| m5C1VH | N | Q | R | F | K | D | K | A | I | L | T | A | D | K | S | S | N | T | A | Y |

| Kabat Numbering | 80 | 81 | 82 | 82A | 82B | 82C | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|
| m5C1VH | M | H | L | S | S | L | T | S | E | D | S | A | V | Y | F | C | A | S | G | G |

| Kabat Numbering | 97 | 98 | 99 | 100 | 101 | 102 | 103 | 104 | 105 | 106 | 107 | 108 | 109 | 110 | 111 | 112 | 113 | 114 |
|---|---|---|---|---|---|---|---|---|---|---|---|---|---|---|---|---|---|---|
| m5C1VH | H | L | A | - | - | Y | W | G | Q | G | T | V | V | T | V | S | A | - |

(SEQ ID NO: 9)

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m5C1VL | D | V | V | M | T | Q | I | P | L | Y | L | S | V | S | P | G | D | Q | A | S |

| Kabat Numbering | 21 | 22 | 23 | 24 | 25 | 26 | 27 | 27A | 27B | 27C | 27D | 27E | 27F | 28 | 29 | 30 | 31 | 32 | 33 | 34 |
|---|---|---|---|---|---|---|---|---|---|---|---|---|---|---|---|---|---|---|---|---|
| m5C1VL | I | S | C | R | S | S | Q | S | L | F | H | S | – | K | G | N | T | Y | L | H |

| Kabat Numbering | 35 | 36 | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|---|---|
| m5C1VL | W | Y | L | Q | K | P | G | Q | S | P | K | L | L | I | N | R | V | S | N | R |

| Kabat Numbering | 55 | 56 | 57 | 58 | 59 | 60 | 61 | 62 | 63 | 64 | 65 | 66 | 67 | 68 | 69 | 70 | 71 | 72 | 73 | 74 |
|---|---|---|---|---|---|---|---|---|---|---|---|---|---|---|---|---|---|---|---|---|
| m5C1VL | F | S | G | V | P | D | R | F | S | G | S | G | S | G | T | D | F | T | L | K |

| Kabat Numbering | 75 | 76 | 77 | 78 | 79 | 80 | 81 | 82 | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|
| m5C1VL | I | S | G | V | E | A | E | D | L | G | V | Y | F | C | S | O | S | A | H | V |

| Kabat Numbering | 95 | 96 | 97 | 98 | 99 | 100 | 101 | 102 | 103 | 104 | 105 | 106 | 107 |
|---|---|---|---|---|---|---|---|---|---|---|---|---|---|
| m5C1VL | P | W | T | F | G | G | G | T | K | L | E | I | R (SEQ ID NO: 24) |

FIG. 2

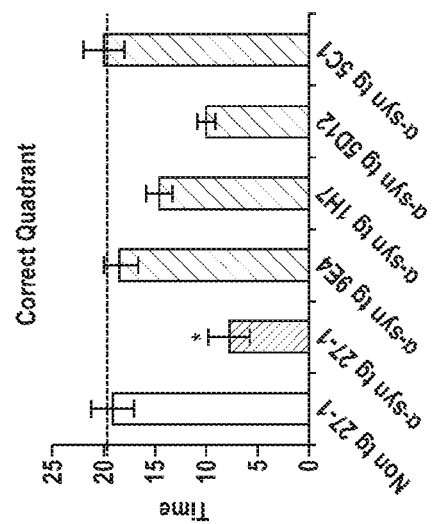
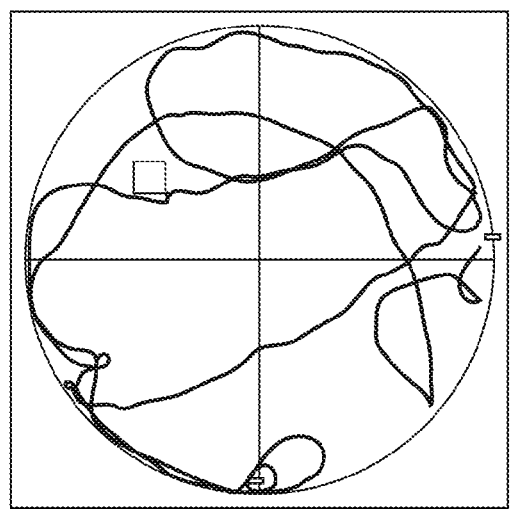
FIG. 3

(SEQ ID NO: 74)

QVQLVQSGAELKKPGSSVKVSCKASGYTFTNYWMNWVRQAPGQGLEWIGATNPNNGYTDYNQRFKDRATLTADKSTNTAY 80
——————————————————————— 5C1VH ———————————————————————

MELSSLRSEDTAVYYCASGGHLAYWGQGTLVTVSSASTKGPSVFPLAPSSKSTSGGTAALGCLVKDYFPEPVTVSWNSGA 160
——— 5C1VH ——— ———————————— hIgG1 constant region ————————————

LTSGVHTFPAVLQSSGLYSLSSVVTVPSSSLGTQTYICNVNHKPSNTKVDKKVEPKSCDKTHTCPPCPAPELLGGPSVFL 240
———————————————————————— hIgG1 constant region ————————————————————————

FPPKPKDTLMISRTPEVTCVVVDVSHEDPEVKFNWYVDGVEVHNAKTKPREEQYNSTYRVVSVLTVLHQDWLNGKEYKCK 320
———————————————————————— hIgG1 constant region ————————————————————————

VSNKALPAPIEKTISKAKGQPREPQV[C]TLPPSRDELTKNQVSL[S]C[A]VKGFYPSDIAVEWESNGQPENNYKTTPPVLDSDG 400
———————————————————————— hIgG1 constant region ————————————————————————

SFFL[V]SKLTVDKSRWQQGNVFSCSVMHEALHNHYTQKSLSLSPGK (SEQ ID NO: 53)
——————— hIgG1 constant region ———————

HOLE residues are in rectangles, additional
Cys residue for S-S bond is in a circle.

FIG. 11

DVVMTQSPLSLSVSPGEPASISCRSSQSLFHSKGNTYLHWYLQKPGQSPQLLINRVSNRFSGVPDRFSGSGSGTDFTLKI
———————————————————————————— 5C1VL_v3 ————————————————————————————

SRVEAEDVGVYFCSQSAHVPWTFGGGTKVEIKRTVAAPSVFIFPPSDEQLKSGTASVVCLLNNFYPREAKVQWKVDNALQ
————————— 5C1VL_v3 —————————————————————————— Hu Igkappa ——————————

SGNSQESVTEQDSKDSTYSLSSTLTLSKADYEKHKVYACEVTHQGLSSPVTKSFNRGEC (SEQ ID NO: 59)
—————————————————————————— Hu Igkappa ——————————————————————

FIG. 12

BLOOD-BRAIN BARRIER SHUTTLES CONTAINING ANTIBODIES RECOGNIZING ALPHA-SYNUCLEIN

CROSS REFERENCE TO RELATED APPLICATIONS

This application is a national-stage application under 35 U.S.C. § 371 of International Application No. PCT/IB2015/052524, filed Apr. 8, 2015, which claims the benefit of U.S. Application No. 61/977,039, filed Apr. 8, 2014, U.S. Application No. 61/977,042, filed Apr. 8, 2014, and U.S. Application No. 62/023,373, filed Jul. 11, 2014, each of which is incorporated by reference in its entirety for all purposes.

SEQUENCE LISTING

The sequence listing written in file 459015SEQLIST.txt is 123 kilobytes in size, was created on Apr. 1, 2015, and is hereby incorporated by reference.

BACKGROUND

Synucleinopathy is a neuropathological finding in a subset of chronic, mostly age-related, neurodegenerative disorders that are characterized by degeneration of the dopaminergic and other neural systems, motor disabilities, cognitive impairment, and formation of specific intraneuronal or intraglial accumulations, such as Lewy bodies (LBs) or Lewy neurites. (McKeith et al., Neurology 47:1113-1124 (1996)). Synucleinopathies include Lewy body diseases, such as Parkinson's disease (including idiopathic Parkinson's disease), diffuse Lewy body disease (DLBD) (also known as dementia with Lewy bodies (DLB)), Lewy body variant of Alzheimer's disease (LBV), Alzheimer's and Parkinson disease comorbidity, and pure autonomic failure, as well as multiple system atrophy (MSA; e.g., olivopontocerebellar atrophy, striatonigral degeneration and Shy-Drager syndrome). Several nonmotor signs and symptoms are thought to be harbingers for synucleinopathies in the prodromal phase of the diseases (i.e., the presymptomatic, subclinical, preclinical, or premotor period). Such early signs include, for example, REM sleep behavior disorder (RBD), loss of smell and constipation (Mahowald et al., Neurology 75:488-489 (2010)). Lewy body diseases continue to be a common cause for movement disorders and cognitive deterioration in the aging population (Galasko et al., Arch. Neurol. 51:888-895(1994)).

Alpha-synuclein is part of a large family of proteins including beta- and gamma-synuclein and synoretin. Alpha-synuclein is expressed in the normal state, and some of it is located in presynaptic terminals, where it regulates vesicular fusion to the synaptic membrane and is believed to play a role in neural function, plasticity, learning, and memory. The protein can aggregate to form insoluble fibrils in pathological conditions, and disorders with histological presence of such aggregates in the brain are therefore called synucleinopathies. Several studies have implicated alpha-synuclein with a central role in Parkinson's disease pathogenesis. For example, alpha-synuclein accumulates in Lewy bodies (LBs) (Spillantini et al., Nature 388:839-840 (1997); Takeda et al., J. Pathol. 152:367-372 (1998); Wakabayashi et al., Neurosci. Lett. 239:45-48 (1997)). Mutations in the alpha-synuclein gene co-segregate with rare familial forms of parkinsonism (Kruger et al., Nature Gen. 18:106-108 (1998); Polymeropoulos, et al., Science 276:2045-2047 (1997)). Overexpression of alpha-synuclein in transgenic mice (Masliah et al., Science 287:1265-1269 (2000)) and Drosophila (Feany et al., Nature 404:394-398 (2000)) mimics several pathological aspects of Lewy body disease. In addition, it has been suggested that soluble oligomers of alpha-synuclein may be neurotoxic (Conway et al., Proc. Nat'l Acad. Sci. USA 97:571-576 (2000); Volles et al., J. Biochem. 42:7871-7878 (2003)). The accumulation of alpha-synuclein with similar morphological and neurological alterations in species and animal models as diverse as humans, mice, and flies suggests that this molecule contributes to the development of Lewy body disease.

Antibodies to alpha-synuclein, or fragments of alpha-synuclein to induce such antibodies, have been proposed for methods of immunotherapy against synucleinopathies such as Lewy body disease. However, brain penetration of antibodies may be limited by the blood-brain barrier (BBB).

SUMMARY OF THE CLAIMED INVENTION

The invention provides blood-brain barrier shuttles comprising: (a) a brain effector entity comprising an antibody having CDRs at least substantially from the 5C1 antibody, wherein 5C1 is a mouse antibody characterized by a heavy chain variable region having an amino acid sequence comprising SEQ ID NO: 9 and light chain variable region having an amino acid sequence comprising SEQ ID NO: 24; and (b) a monovalent binding entity that binds to a blood-brain barrier receptor; wherein the brain effector entity is coupled to the monovalent binding entity. Optionally, the brain effector entity antibody comprises three heavy chain CDRs having amino acid sequences of SEQ ID NOS: 10, 11, and 12, respectively, and three light chain CDRs having amino acid sequences of SEQ ID NOS: 25, 26, and 27, respectively.

The invention further provides blood-brain barrier shuttles comprising: (a) a brain effector entity comprising an antibody that binds to human alpha-synuclein, wherein alanine scanning mutagenesis of residues 118-126 of full-length human alpha-synuclein indicates residues 120, 121, and 122 each contributes to the binding more than each of residues 123 and 124, and residues 123 and 124 each contributes to binding more than each of residues 118, 119, 125 and 126; and (b) a monovalent binding entity that binds to a blood-brain barrier receptor; wherein the brain effector entity is coupled to the monovalent binding entity.

In some of the blood-brain barrier shuttles described above, the brain effector entity antibody binds to human alpha-synuclein at an epitope consisting essentially of residues 120-122 of SEQ ID NO: 1 and excluding residues 118-119 of SEQ ID NO: 1. In some of the blood-brain barrier shuttles described above, the brain effector entity antibody binds to human alpha-synuclein at an epitope consisting of residues 120-124 of SEQ ID NO: 1.

The invention further provides blood-brain barrier shuttles comprising: (a) a brain effector entity comprising an antibody comprising three light chain CDRs as defined by Kabat and three heavy chain CDRs as defined by Kabat of monoclonal antibody 5C1, wherein 5C1 is a mouse antibody characterized by a heavy chain variable region having an amino acid sequence comprising SEQ ID NO: 9 and light chain variable region having an amino acid sequence comprising SEQ ID NO: 24; and (b) a monovalent binding entity that binds to a blood-brain barrier receptor; wherein the brain effector entity is coupled to the monovalent binding entity.

In some of the blood-brain barrier shuttles described above, the brain effector entity antibody is chimeric, veneered, humanized, or human. In some of the blood-brain barrier shuttles described above, the brain effector entity antibody is a humanized antibody. In some of the blood-brain barrier shuttles described above, the brain effector entity antibody is a chimeric antibody. In some of the blood-brain barrier shuttles described above, the brain effector entity antibody is a veneered antibody. In some of the blood-brain barrier shuttles described above, the brain effector entity antibody is of the isotype human IgG1.

In some of the blood-brain barrier shuttles described above, the brain effector entity antibody has at least one mutation in the constant region. Optionally, the mutation reduces complement fixation or activation by the constant region. Optionally, the brain effector entity antibody has a mutation in the constant region at one or more of positions 241, 264, 265, 270, 296, 297, 322, 329, and 331 by EU numbering. Optionally, the brain effector entity antibody has an alanine at positions 318, 320, and 322. Optionally, the brain effector entity antibody has a mutation at one or more of positions 234, 235, 237, and 329 by EU numbering. Optionally, the brain effector entity antibody has an alanine at one or more of positions 234, 235, and 237. Optionally, the brain effector entity antibody has an alanine at positions 234 and 235 and a glycine at position 329.

In some of the blood-brain barrier shuttles described above, the brain effector entity antibody has an isotype of human IgG2 or IgG4.

In some of the blood-brain barrier shuttles described above, the brain effector entity antibody is a Fab fragment, F(ab')2 fragment, or scFv.

The invention further provides blood-brain barrier shuttles comprising: (a) a brain effector entity comprising an antibody comprising a mature heavy chain variable region having an amino acid sequence at least 90% identical to H4 (SEQ ID NO: 17) and a mature light chain variable region having an amino acid sequence at least 90% identical to L3 (SEQ ID NO: 31), wherein the antibody specifically binds to human alpha-synuclein; and (b) a monovalent binding entity that binds to a blood-brain barrier receptor; wherein the brain effector entity is coupled to the monovalent binding entity. Optionally, the brain effector entity antibody comprises three Kabat CDRs of SEQ ID NO: 9 and three Kabat CDRs of SEQ ID NO: 24. Optionally, at least one of positions H11, H27, H30, H48, and H73 in the brain effector entity antibody is occupied by L, Y, T, I, and K, respectively, and at least one of positions L12 and L14 in the brain effector entity antibody is occupied by S. Optionally, positions H11, H27, H30, H48, and H73 in the brain effector entity antibody are occupied by L, Y, T, I, and K, respectively, and positions L12 and L14 in the brain effector entity antibody are occupied by S. Optionally, at least one of positions H67, H69, and H94 in the brain effector entity antibody is occupied by A, L, and S, respectively. Optionally, positions H67, H69, and H94 in the brain effector entity antibody are occupied by A, L, and S, respectively. Optionally, position H94 in the brain effector entity antibody is occupied by S. Optionally, at least one of positions L2, L49, and L87 in the brain effector entity antibody is occupied by V, N, and F, respectively. Optionally, positions L2, L49, and L87 in the brain effector entity antibody are occupied by V, N, and F, respectively. Optionally, the brain effector entity antibody comprises a mature heavy chain variable region having an amino acid sequence at least 95% identical to H4 (SEQ ID NO: 17) and a mature light chain variable region at least 95% identical to L3 (SEQ ID NO: 31). Optionally, any differences in the CDRs of the brain effector entity antibody's mature heavy chain variable region and mature light chain variable region from the CDRs of H4 (SEQ ID NO: 17) and L3 (SEQ ID NO: 31), respectively, reside in positions H60-H65. Optionally, the brain effector entity antibody's mature heavy chain variable region has an amino acid sequence designated H4 (SEQ ID NO: 17) and the brain effector entity antibody's mature light chain variable region has an amino acid sequence designated L3 (SEQ ID NO: 31). Optionally, the brain effector entity antibody's mature heavy chain variable region has an amino acid sequence designated H5 (SEQ ID NO: 18) and the brain effector entity antibody's mature light chain variable region has an amino acid sequence designated L3 (SEQ ID NO: 31).

In some of the blood-brain barrier shuttles described above, the brain effector entity antibody's mature heavy chain variable region is fused to a heavy chain constant region, and the brain effector entity antibody's mature light chain variable region is fused to a light chain constant region. Optionally, the brain effector entity antibody's heavy chain constant region is a mutant form of a natural human heavy chain constant region which has reduced binding to an Fcγ receptor relative to the natural human heavy chain constant region. Optionally, the brain effector entity antibody's mature heavy chain variable region is fused to a heavy chain constant region having the sequence of SEQ ID NO: 66 and/or the brain effector entity antibody's mature light chain variable region is fused to a light chain constant region having the sequence of SEQ ID NO: 52. Optionally, the brain effector entity antibody's mature heavy chain variable region is fused to a heavy chain constant region having the sequence of SEQ ID NO: 66 or 75 and/or the brain effector entity antibody's mature light chain variable region is fused to a light chain constant region having the sequence of SEQ ID NO: 52.

In some of the blood-brain barrier shuttles described above, the brain effector entity antibody is a Fab fragment, F(ab')2 fragment, or scFv.

In some of the blood-brain barrier shuttles described above, the monovalent binding entity comprises a blood-brain barrier receptor ligand, antibody fragment, or other polypeptide. Optionally, the monovalent binding entity comprises an antibody fragment that is a scFv, Fv, scFab, sFab, or VHH. Optionally, the monovalent binding entity comprises a sFab.

In some of the blood-brain barrier shuttles described above, the blood-brain barrier receptor is a transferrin receptor, insulin receptor, insulin-like growth factor receptor, low density lipoprotein receptor-related protein 8, low density lipoprotein receptor-related protein 1, or heparin-binding epidermal growth factor-like growth factor. Optionally, the blood-brain barrier receptor is a transferrin receptor.

In some of the blood-brain barrier shuttles described above, the monovalent binding entity comprises a sFab that specifically binds to a transferrin receptor. Optionally, the sFab binds to an epitope within SEQ ID NO: 43, SEQ ID NO: 44, and/or SEQ ID NO: 45.

In some of the blood-brain barrier shuttles described above, the brain effector entity is coupled to the monovalent binding entity by a first linker. Optionally, the first linker is a peptide linker. Optionally, the peptide linker has a length of at least 20 amino acids. Optionally, the peptide linker has a length of 25 to 50 amino acids. Optionally, the peptide linker has an amino acid sequence of SEQ ID NO: 41. Optionally, the peptide linker has an amino acid sequence of SEQ ID NO: 42. Optionally, the peptide linker has an amino acid sequence of SEQ ID NO: 73. Optionally, the monovalent binding entity is coupled to the C-terminal end of a heavy chain of the brain effector entity antibody by the first linker.

In some of the blood-brain barrier shuttles described above, the monovalent binding entity comprises a CH2-CH3 Ig entity and a sFab that specifically binds to the blood-brain barrier receptor, wherein the sFab is coupled to the C-terminal end of the CH2-CH3 Ig entity. Optionally, the CH2-CH3 Ig entity is a CH2-CH3 IgG entity In some of the blood-brain barrier shuttles described above, the monovalent binding entity comprises a CH2-CH3 Ig entity and a sFab that specifically binds to the blood-brain barrier receptor, a first linker couples the N-terminal end of the CH2-CH3 Ig domain to the brain effector entity, and a second linker couples the C-terminal end of the CH2-CH3 Ig domain to the sFab. Optionally, the CH2-CH3 Ig entity is a CH2-CH3 IgG entity.

In some of the blood-brain barrier shuttles described above, the brain effector entity antibody includes the Fc region of a heavy chain, and the monovalent binding entity is coupled to the C-terminal end of the Fc region of the heavy chain. Optionally, the brain effector entity antibody comprises two heavy chains, and the monovalent binding entity is coupled to the C-terminal end of the Fc region of only one of the heavy chains. Optionally, the brain effector entity antibody comprises a heterodimerized heavy chain comprising first and second dimerization modules, and only one the first and second dimerization modules is coupled to the monovalent binding entity. Optionally, the first dimerization module comprises knobs and the second dimerization module comprises holes to receive the knobs.

In some of the blood-brain barrier shuttles described above, the brain effector entity antibody comprises an IgG heavy chain including an Fc region, the monovalent binding entity comprises a sFab, the C-terminal end of the Fc region of the brain effector entity antibody heavy chain is coupled to the N-terminal end of the variable light chain domain of the sFab, and the C-terminal end of the C-kappa light chain domain of the sFab is coupled to the N-terminal end of the variable heavy chain domain of the sFab.

The invention further provides blood-brain barrier shuttles comprising: (a) a brain effector entity comprising an antibody with a light chain having an amino acid sequence comprising SEQ ID NO: 59 and a heterodimerized heavy chain with first and second dimerization modules having amino acid sequences comprising SEQ ID NOS: 53 and 69, respectively, or SEQ ID NOS: 55 and 70, respectively; (b) a first linker; and (c) a monovalent binding entity comprising an 8D3-scFab comprising a heavy chain variable region having an amino acid sequence comprising SEQ ID NO: 64 and a light chain variable region having an amino acid sequence comprising SEQ ID NO: 63, wherein the heavy and light chains of the 8D3-scFab are coupled by a second linker; wherein only one of the first and second dimerization modules of the brain effector entity antibody is coupled to the monovalent binding entity by the first linker. Optionally, the 8D3-scFab comprises heavy and light chains having amino acid sequences comprising SEQ ID NOS: 62 and 61, respectively. Optionally, the first linker couples the C-terminal end of a heavy chain of the brain effector entity antibody to the N-terminal end of the monovalent binding entity. Optionally, the first linker has an amino acid sequence comprising SEQ ID NO: 41, 42, or 73. Optionally, the second linker has an amino acid sequence comprising SEQ ID NO: 41, 42, or 73. Optionally, the 8D3-scFab has an amino acid sequence comprising SEQ ID NO: 60.

In some of the blood-brain barrier shuttles described above, the brain effector antibody comprises a first heavy chain and a second heavy chain, the first heavy chain comprises the mature heavy chain variable region fused to a heavy chain constant region having an amino acid sequence comprising SEQ ID NO: 46, and the second heavy chain comprises the mature heavy chain variable region fused to a heavy chain constant region having an amino acid sequence comprising SEQ ID NO: 67. Optionally, the monovalent binding entity is coupled to the C-terminal end of the second heavy chain. Optionally, the monovalent binding entity comprises an 8D3-scFab comprising a heavy chain variable region having an amino acid sequence comprising SEQ ID NO: 64 and a light chain variable region having an amino acid sequence comprising SEQ ID NO: 63. Optionally, the monovalent binding entity comprises an 8D3-scFab comprising heavy and light chains having amino acid sequences comprising SEQ ID NOS: 62 and 61, respectively. Optionally, the brain effector entity and the monovalent entity are coupled by a first linker and the 8D3 heavy and light chains are coupled by a second linker. Optionally, the first linker has an amino acid sequence comprising SEQ ID NO: 73, and the second linker has an amino acid sequence comprising SEQ ID NO: 41.

The invention further provides pharmaceutical compositions comprising any of the blood-brain barrier shuttles described above and a pharmaceutically acceptable carrier.

The invention further provides nucleic acids encoding any of the blood-brain barrier shuttles described above. Optionally, the nucleic acid encodes an amino acid sequence comprising SEQ ID NOS: 53, 57, and/or 59. Optionally, the nucleic acid encodes an amino acid sequence comprising SEQ ID NOS: 55, 58, and/or 59.

The invention further provides recombinant expression vectors comprising any of the nucleic acids described above. Optionally, the recombinant expression vector comprises a nucleic acid encoding an amino acid sequence comprising SEQ ID NO: 53, SEQ ID NO: 57, or SEQ ID NO: 59. Optionally, the recombinant expression vector comprises a nucleic acid encoding an amino acid sequence comprising SEQ ID NO: 55, SEQ ID NO: 58, or SEQ ID NO: 59.

The invention further provides a transfection mixture comprising three recombinant expression vectors comprising nucleic acids encoding amino acid sequences comprising SEQ ID NOS: 53, 57, and 59, respectively. The invention further provides a transfection mixture comprising nucleic acids encoding amino acid sequences comprising SEQ ID NOS: 55, 58, and 59, respectively. Optionally, the three recombinant expression vectors are present in equimolar amounts.

The invention further provides host cells transformed with any of the recombinant expression vectors or any of the transfection mixtures described above.

The invention further provides a method for producing a blood-brain barrier shuttle, the method comprising: (a) culturing cells transformed with any of the nucleic acids described above so that the cells secrete the blood-brain barrier shuttle; and (b) purifying the secreted blood-brain barrier shuttle.

The invention further provides a method for producing a cell line producing a blood-brain barrier shuttle, the method comprising: (a) introducing any of the recombinant expression vectors described above into cells, wherein the recombinant expression vector further comprises a selectable marker; (b) propagating the cells under conditions to select for cells having increased copy number of the vector; (c) isolating single cells from the selected cells; and (d) banking cells cloned from a single cell based on yield of the blood-brain barrier shuttle. Optionally, the method further comprises propagating the cells under selective conditions and screening for cell lines naturally expressing and secreting at least 100 mg/L/10⁶ cells/24 h.

The invention further provides a method of treating or effecting prophylaxis of a synucleinopathy in a patient, the method comprising administering to the patient an effective regime of any of the blood-brain barrier shuttles described above. Optionally, the synucleinopathy is a Lewy body disease. Optionally, the patient has EM sleep behavior disorder (RBD). Optionally, the synucleinopathy is Parkinson's disease. Optionally, the synucleinopathy is multiple system atrophy (MSA) or dementia with Lewy bodies (DLB). Optionally, the method inhibits decline of cognitive function in the patient. Optionally, the method reduces neuritic and/or axonal alpha-synuclein aggregates. Optionally, the method reduces neuritic dystrophy in the patient. Optionally, the method preserves synaptic and/or dendritic densities. Optionally, the method preserves synaptophysin and/or MAP2 in the patient.

The invention further provides a method of inhibiting alpha-synuclein aggregation or reducing alpha-synuclein aggregates in a patient having or at risk of a synucleinopathy, the method comprising administering to the patient an effective amount of any of the blood-brain barrier shuttles described above. Optionally, the alpha-synuclein aggregates comprise Lewy bodies, and the synucleinopathy is a Lewy body disease. Optionally, the synucleinopathy is Parkinson's disease. Optionally, the synucleinopathy is multiple system atrophy (MSA) or dementia with Lewy bodies (DLB). Optionally, the method inhibits decline of cognitive function in the patient. Optionally, the method reduces neuritic and/or axonal alpha-synuclein aggregates. Optionally, the method reduces neuritic dystrophy in the patient. Optionally, the method preserves synaptic and/or dendritic densities. Optionally, the method preserves synaptophysin and/or MAP2 in the patient.

The invention further provides a method of detecting alpha-synuclein aggregates in a patient having or at risk of a synucleinopathy, the method comprising: (a) administering to the patient an effective amount of any of the blood-brain barrier shuttles described above, wherein the brain effector entity antibody binds to Lewy bodies; and (b) detecting bound brain effector entity antibody in the patient. Optionally, the alpha-synuclein aggregates comprise Lewy bodies, and the synucleinopathy is a Lewy body disease.

The invention further provides a method of transporting a brain effector entity across a blood-brain barrier, the method comprising exposing any of the blood-brain barrier shuttles described above to the blood-brain barrier such that the monovalent binding entity transports the brain effector entity across the blood-brain barrier.

The invention further provides an antibody comprising: (a) a pair of light chains, each having an amino acid sequence comprising SEQ ID NO: 59; (b) a first heavy chain having an amino acid sequence comprising SEQ ID NO: 53; and (c) a second heavy chain having an amino acid sequence comprising SEQ ID NO: 57; wherein the first and second heavy chains form a heterodimer.

The invention further provides an antibody comprising: (a) a pair of light chains, each having an amino acid sequence comprising SEQ ID NO: 59; (b) a first heavy chain having an amino acid sequence comprising SEQ ID NO: 55; and (c) a second heavy chain having an amino acid sequence comprising SEQ ID NO: 58; wherein the first and second heavy chains form a heterodimer.

BRIEF DESCRIPTION OF THE DRAWINGS

FIG. 1 shows the amino acid sequences of mouse 5C1 heavy chain mature variable region. CDR regions according to Kabat definition are underlined and in bold.

FIG. 2 shows the amino acid sequences of mouse 5C1 light chain mature variable region. CDR regions according to Kabat definition are underlined and in bold.

FIG. 3 shows the results of passive immunotherapy with 5C1 on memory performance of human alpha-synuclein transgenic mice in probe portion of the Morris water maze test.

FIG. 11 depicts the "hole" 5C1H4-HuIgG1 heavy chain fusion protein.

FIG. 12 depicts the 5C1L3-HuIgKappa light chain fusion protein.

BRIEF DESCRIPTION OF THE SEQUENCES

Figure 4:
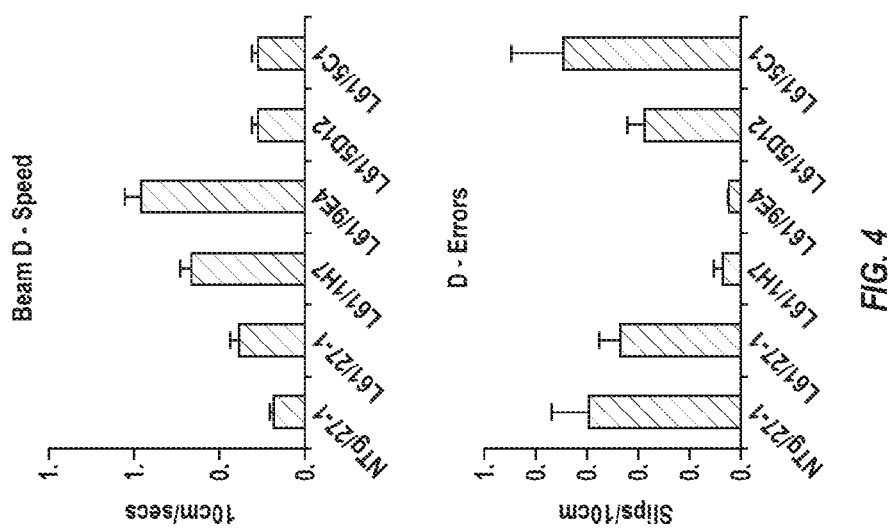
FIG. 4 shows the results of passive immunotherapy in human alpha-synuclein transgenic mice with 5C1 on speed and errors in the round beam test.

SEQ ID NO: 1 is wild-type human alpha-synuclein.

SEQ ID NO: 2 is the non-amyloid component (NAC) domain of alpha-synuclein, as reported by Jensen et al. (1995).

SEQ ID NO: 3 is the non-amyloid component (NAC) domain of alpha-synuclein, as reported by Ueda et al. (1993).

SEQ ID NO: 4 is the 5C1 peptide immunogen amino acid residues 118-129 of human alpha-synuclein.

SEQ ID NO: 5 is the nucleic acid sequence encoding the murine 5C1 heavy chain variable region with sequence encoding signal peptide.

SEQ ID NO: 6 is the murine 5C1 heavy chain variable region with signal peptide.

SEQ ID NO: 7 is the nucleic acid sequence encoding the murine 5C1 light chain variable region with sequence encoding signal peptide.

SEQ ID NO: 8 is the murine 5C1 light chain variable region sequence with signal peptide.

SEQ ID NO: 9 is the murine 5C1 mature heavy chain variable region.

SEQ ID NO: 10 is the sequence of the 5C1 heavy chain CDR1 as defined by Kabat.

SEQ ID NO: 11 is the sequence of the 5C1 heavy chain CDR2 as defined by Kabat.

SEQ ID NO: 12 is the sequence of the 5C1 heavy chain CDR3 as defined by Kabat.

SEQ ID NO: 13 is the human VH Acceptor FR (Acc # AAY42876.1).

SEQ ID NO: 14 is the sequence of humanized 5C1H1.

SEQ ID NO: 15 is the sequence of humanized 5C1H2.

SEQ ID NO: 16 is the sequence of humanized 5C1H3.

SEQ ID NO: 17 is the sequence of humanized 5C1H4.

SEQ ID NO: 18 is the sequence of humanized 5C1H5.

SEQ ID NO: 19 is the nucleic acid sequence encoding humanized 5C1H1 with sequence encoding signal peptide.

SEQ ID NO: 20 is the nucleic acid sequence encoding humanized 5C1H2 with sequence encoding signal peptide.

SEQ ID NO: 21 is the nucleic acid sequence encoding humanized 5C1H3 with sequence encoding signal peptide.

SEQ ID NO: 22 is the nucleic acid sequence encoding humanized 5C1H4 with sequence encoding signal peptide.

SEQ ID NO: 23 is the nucleic acid sequence encoding humanized 5C1H5 with sequence encoding signal peptide.

SEQ ID NO: 24 is the murine 5C1 mature light chain variable region sequence.

SEQ ID NO: 25 is the sequence of the 5C1 light chain CDR1 as defined by Kabat.

SEQ ID NO: 26 is the sequence of the 5C1 light chain CDR2 as defined by Kabat.

SEQ ID NO: 27 is the sequence of the 5C1 light chain CDR3 as defined by Kabat.

SEQ ID NO: 28 is the human VL Acceptor FR (Acc # CAB51293.1).

SEQ ID NO: 29 is the sequence of humanized 5C1L1.

SEQ ID NO: 30 is the sequence of humanized 5C1L2.

SEQ ID NO: 31 is the sequence of humanized 5C1L3.

SEQ ID NO: 32 is the sequence of humanized 5C1L4.

SEQ ID NO: 33 is the nucleic acid sequence encoding humanized 5C1L1 with sequence encoding signal peptide.

SEQ ID NO: 34 is the nucleic acid sequence encoding humanized 5C1L2 with sequence encoding signal peptide.

SEQ ID NO: 35 is the nucleic acid sequence encoding humanized 5C1L3 with sequence encoding signal peptide.

SEQ ID NO: 36 is the nucleic acid sequence encoding humanized 5C1L4 with sequence encoding signal peptide.

SEQ ID NO: 37 is the nucleic acid sequence encoding an exemplary human IgG1 constant region.

SEQ ID NO: 38 is the amino acid sequence of an exemplary human IgG1 constant region.

SEQ ID NO: 39 is the nucleic acid sequence encoding an exemplary human kappa light chain constant region without an N-terminal arginine.

SEQ ID NO: 40 is the amino acid sequence of an exemplary human kappa light chain constant region without an N-terminal arginine.

SEQ ID NO: 41 is the amino acid sequence of a peptide linker with the formula $(G_4S)_6G_2$.

SEQ ID NO: 42 is the amino acid sequence of a peptide linker with the formula $(G_4S)_4$.

SEQ ID NO: 43 is the amino acid sequence of 8D3 epitope mapping peptide 373.

SEQ ID NO: 44 is the amino acid sequence of 8D3 epitope mapping peptide 374.

SEQ ID NO: 45 is the amino acid sequence of 8D3 epitope mapping peptide 375.

SEQ ID NO: 46 is the amino acid sequence of HU-IGG1-HC-HOLE.

SEQ ID NO: 47 is the amino acid sequence of HU-IGG1-HC-KNOB.

SEQ ID NO: 48 is the amino acid sequence of HU-IGG1-HC-HOLE_LALAPG.

SEQ ID NO: 49 is the amino acid sequence of HU-IGG1-HC-KNOB_LALAPG.

SEQ ID NO: 50 is the amino acid sequence of HU-IGG1-HC-KNOB_8D3-scFab.

SEQ ID NO: 51 is the amino acid sequence of HU-IGG1-HC-KNOB_LALAPG_8D3-scFab.

SEQ ID NO: 52 is the amino acid sequence of HU-IGKAPPA-LC (with N-terminal arginine).

SEQ ID NO: 53 is the amino acid sequence of 5C1-H4_HU-IGG1-HC-HOLE.

SEQ ID NO: 54 is the amino acid sequence of 5C1-H4_HU-IGG1-HC-KNOB.

SEQ ID NO: 55 is the amino acid sequence of 5C1-H4_HU-IGG1-HC-HOLE_LALAPG.

SEQ ID NO: 56 is the amino acid sequence of 5C1-H4_HU-IGG1-HC-KNOB_LALAPG.

SEQ ID NO: 57 is the amino acid sequence of 5C1-H4_HU-IGG1-HC-KNOB_8D3-scFab.

SEQ ID NO: 58 is the amino acid sequence of 5C1-H4_HU-IGG1-HC-KNOB_LALAPG_8D3-scFab.

SEQ ID NO: 59 is the amino acid sequence of 5C1-L3_HU-IGKAPPA-LC.

SEQ ID NO: 60 is the amino acid sequence of 8D3-scFab.

SEQ ID NO: 61 is the amino acid sequence of 8D3VL-HU-IGKAPPA-LC.

SEQ ID NO: 62 is the amino acid sequence of 8D3VH-HU-CH1.

SEQ ID NO: 63 is the amino acid sequence of 8D3VL.

SEQ ID NO: 64 is the amino acid sequence of 8D3VH.

SEQ ID NO: 65 is the amino acid sequence of HU-CH1.

SEQ ID NO: 66 is the amino acid sequence of an exemplary human IgG1 constant region of the IgG1 G1m3 allotype.

SEQ ID NO: 67 is the amino acid sequence of HU-IGG1-HC-KNOB with the C-terminal glycine and lysine residues removed.

SEQ ID NO: 68 is the amino acid sequence of HU-IGG1-HC-KNOB_LALAPG with the C-terminal glycine and lysine residues removed.

SEQ ID NO: 69 is the amino acid sequence of 5C1-H4_HU-IGG1-HC-KNOB with the C-terminal glycine and lysine residues removed.

SEQ ID NO: 70 is the amino acid sequence of 5C1-H4_HU-IGG1-HC-KNOB_LALAPG with the C-terminal glycine and lysine residues removed.

SEQ ID NO: 71 is the nucleic acid sequence encoding HU-IGKAPPA-LC (with N-terminal arginine).

SEQ ID NO: 72 is the nucleic acid sequence encoding an exemplary human IgG1 constant region of the IgG1 G1m3 allotype.

SEQ ID NO: 73 is the amino acid sequence of a peptide linker with the formula $G_3S(G_4S)_3$.

SEQ ID NO: 74 is amino acid residues 118-126 of human alpha-synuclein.

SEQ ID NO: 75 is the amino acid sequence of an exemplary human IgG1 constant region of the IgG1 G1m3 allotype.

DEFINITIONS

The basic antibody structural unit is a tetramer of subunits. Each tetramer includes two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. When initially expressed, this variable region is typically linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function. A constant region can include any or all of a CH1 region, hinge region, CH2 region, and CH3 region.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except for bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the regions FR1, CDR1, FR2, CDR2, FR3, CDR3 and FR4. The assignment of amino acids to each region is in accordance with the definitions of Kabat, *Sequences of Proteins of Immunological Interest* (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number (e.g., H83 means position 83 by Kabat numbering in the mature heavy chain variable region; likewise position L36 means position 36 by Kabat numbering in the mature light chain variable region). Kabat numbering is used throughout in referring to positions in the variable region of an antibody unless explicitly stated otherwise.

The term "antibody" includes intact antibodies and binding fragments thereof. Typically, fragments compete with the intact antibody from which they were derived for specific binding to the target. Fragments include separate heavy chains, separate light chains, Fab, Fab', F(ab')2, F(ab)c, Fv, single chain antibodies, and single domain antibodies. Single (variable) domain antibodies include VH regions separated from their VL partners (or vice versa) in conventional antibodies (Ward et al., 1989, Nature 341: 544-546), as well as VH regions (sometimes known as VHH) from species such as *Camelidae* or cartilaginous fish (e.g., a nurse shark) in which VH regions are not associated with VL regions (see, e.g., WO 9404678). Single domain antibodies in which one chain is separated from its natural partners are sometimes known as Dabs and single domain antibodies from *Caemelidae* or cartilaginous fish are sometimes known as nanobodies. Constant regions or parts of constant regions may or may not be present in single domain antibodies. For example, natural single variable region antibodies from *Camelidae* include a VHH variable region, and CH2 and CH3 constant regions. Single domain antibodies, such as nanobodies, can be subject to humanization by analogous approaches to conventional antibodies. Dabs antibodies are usually obtained from antibodies of human origin. Fragments can be produced by recombinant DNA techniques, or by enzymatic or chemical separation of intact immunoglobulins.

The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol. 148:1547-53 (1992)). In some bispecific antibodies, the two different heavy/light chain pairs include a humanized 5C1 heavy chain/light chain pair and a heavy chain/light chain pair specific for a different epitope on alpha-synuclein than that bound by 5C1.

In some bispecific antibodies, one heavy chain light chain pair is a humanized 5C1 antibody as further disclosed below and the heavy light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., PNAS 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distributioin in the brain (see, e.g., Atwal. et al. Sci. Trans. Med. 3, 84ra43, 2011; Yu et al. Sci. Trans. Med. 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

An "antigen" is an entity to which an antibody specifically binds.

The term "epitope" refers to a site on an antigen to which an antibody binds. For protein antigens, an epitope can be formed from contiguous amino acids or noncontiguous amino acids juxtaposed by tertiary folding of one or more proteins. Epitopes formed from contiguous amino acids are typically retained on exposure to denaturing solvents, whereas epitopes formed by tertiary folding are typically lost on treatment with denaturing solvents. An epitope typically includes at least 2, 3, and more usually, at least 5 or 8-10 amino acids in a unique spatial conformation. Methods of determining spatial conformation of epitopes include, for example, X-ray crystallography and 2-dimensional nuclear magnetic resonance. See, e.g., Epitope Mapping Protocols, in Methods in Molecular Biology, Vol. 66, Glenn E. Morris, Ed. (1996). An epitope can include a C-terminal residue or an N-terminal residue. An epitope can also include, but need not include, the free amino group of a polypeptide or the free carboxyl group of a polypeptide. Thus, an epitope can include a C-terminal or an N-terminal residue, but not necessarily include the free carboxyl group or the free amino group, respectively. Antibody binding specificity is sometimes defined by a range of amino acids. If an antibody is said to bind to an epitope within amino acids 118-126 of SEQ ID NO: 1, for example, what is meant is that the epitope is within the recited range of amino acids including those defining the outer-limits of the range. It does not necessarily mean that every amino acid within the range constitutes part of the epitope. Thus, for example, an epitope within amino acids 118-126 of SEQ ID NO: 1 may consist of amino acids 118-124, 119-125, 120-126, 120-124, or 120-122, among other segments of SEQ ID NO: 1.

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues (the epitope being defined by the residues making contact). Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen. See, e.g., Junghans et al. (1990), Cancer Res. 50:1495. A test antibody competes with a reference antibody if an excess of a test antibody (e.g., at least 2×, 5×, 10×, 20× or 100×) inhibits binding of the reference antibody by at least 50%, 75%, 90%, 95%, 98%, or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

Antibodies typically bind to their designated target with an affinity constant of at least $10^6$, $10^7$, $10^8$, $10^9$, or $10^{10}$ M−1. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

When comparing antibody sequences, percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Monoclonal antibodies are typically provided in isolated form. This means that the antibody is typically at least 50% w/w pure of interfering proteins and other contaminants arising from its production or purification, but does not exclude the possibility that the agent is combined with an excess of pharmaceutically-acceptable carrier(s) or other vehicle intended to facilitate its use. Sometimes monoclonal antibodies are at least 60%, 70%, 80%, 90%, 95%, 96%, 97%, 98%, or 99% w/w pure of aggregates or fragments of such monoclonal antibodies or of other proteins and contaminants. Some such monoclonal antibodies may include aggregates or fragments but are at least 99% w/w pure of other proteins and contaminants.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses values within the margin of error of measurement (SEM) of a stated value.

Statistical significance means $p \leq 0.05$.

A "patient" includes a human or other mammalian subject that receives either prophylactic or therapeutic treatment.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor.

The term "symptom" refers to a subjective evidence of a disease, such as altered gait, as perceived by the patient. A "sign" refers to objective evidence of a disease as observed by a physician.

"Cognitive function" refers to mental processes such as any or all of attention, memory, producing and understanding language, solving problems, and taking an interest in one's surroundings and self-care.

"Enhanced cognitive function" or "improved cognitive function" refers to improvement relative to a baseline, for example, diagnosis or initiation of treatment. "Decline of cognitive function" refers to a decrease in function relative to such a base line.

In animal model systems such as rat or mouse, cognitive function may be measured methods including using a maze in which subjects use spatial information (e.g., Morris water maze, Barnes circular maze, elevated radial arm maze, T maze and others), fear conditioning, active avoidance, illuminated open-field, dark activity meter, elevated plus-maze, two-compartment exploratory test or forced swimming test.

In humans, cognitive function can be measured by one or more of several standardized tests. Examples of a test or assay for cognitive function were described (Ruoppila and Suutama, Scand. J. Soc. Med. Suppl. 53, 44-65, 1997) and include standardized psychometric tests (e.g., Wechsler Memory Scale, the Wechsler Adult Intelligence Scale, Raven's Standard Progressive Matrices, Schaie-Thurstone Adult Mental Abilities Test), neuropsychological tests (e.g., Luria-Nebraska), metacognitive self-evaluations (e.g., Metamemory Questionnaire), visual-spatial screening tests (e.g., Poppelreuter's Figures, Clock Recognition, Honeycomb Drawing and Cancellation), cognitive screening tests (e.g., Folstein's Mini Mental State Test) and reaction time tests. Other standard tests for cognitive performance include the Alzheimer's Disease Assessment Scale-cognitive subscale (ADAS-cog); the clinical global impression of change scale (CIBIC-plus scale); the Alzheimer's Disease Cooperative Study Activities of Daily Living Scale (ADCS-ADL); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG), Stroop Test, Trail Making, Wechsler Digit Span, and the CogState computerized cognitive test. In addition, cognitive function may be measured using imaging techniques such as Positron Emission Tomography (PET), functional magnetic resonance imaging (fMRI), Single Photon Emission Computed Tomography (SPECT), or any other imaging technique that allows one to measure brain function.

A "transfection mixture" is any combination of agents required for the introduction of an extracellular nucleic acid into a host cell by any method. Such methods can include, for example, calcium phosphate-DNA co-precipitation, DEAE-dextran-mediated transfection, polybrene-mediated transfection, electroporation, microinjection, microparticle bombardment, liposome fusion, lipofection, protoplast fusion, retroviral infection, viral transduction, and biolistics.

The singular forms of the articles "a," "an," and "the" include plural references unless the context clearly indicates otherwise. For example, the term "a compound" or "at least one compound" can include a plurality of compounds, including mixtures thereof.

DETAILED DESCRIPTION

I. General

The invention provides blood-brain barrier (BBB) shuttles formed by coupling monoclonal antibody 5C1 or a related antibody, such as antibodies that bind to the same epitope on alpha-synuclein, to a monovalent binding entity that binds to a receptor on the cells forming the BBB (blood-brain barrier receptor, or BBB receptor). Although practice of the invention is not dependent on an understanding of mechanism, binding of the monovalent binding entity to the blood-brain barrier receptor facilitates passage of the antibody across the blood-brain barrier. The antibodies are useful, for example, for treating disorders associated with alpha-synuclein accumulation (e.g., synucleinopathies). Such disorders include Lewy body diseases, such as Parkinson's disease, diffuse Lewy body disease (DLBD), Lewy body variant of Alzheimer's disease (LBV), Alzheimer's and Parkinson's disease comorbidity, and pure autonomic failure, as well as multiple system atrophy (MSA). The antibodies are also useful for diagnoses of synucleinopathies.

II. Target Molecules

Natural human wild-type alpha-synuclein is a peptide of 140 amino acids having the amino acid sequence of SEQ ID NO: 1 (Uéda et al., Proc. Natl. Acad. Sci. USA, 90:11282-6, 1993; GenBank accession number: P37840). The protein has three recognized domains, a KTKE repeat domain covering amino acids 1-61, a NAC (Non-amyloid component) domain running from about amino acids 60-95, and a C-terminal acidic domain running from about amino acid 98 to 140. Jensen et al. (1995) reported that NAC has the amino acid sequence of SEQ ID NO: 2 (Jensen et al., Biochem. J. 310.1: 91-94; GenBank accession number S56746). However, Uéda et al. (1993) reported that NAC has the amino acid sequence of SEQ ID NO: 3 (Uéda et al., Proc. Natl. Acad. Sci. USA, 90:11282-6).

Unless otherwise apparent from the context, reference to alpha-synuclein or its fragments includes the natural human wild-type amino acid sequences indicated above, and human allelic variants thereof, particularly those associated with familial inherited forms of Lewy body and Parkinson's disease (e.g., E46K, A30P and A53T, with the first letter indicates the amino acid in SEQ ID NO: 1, the number is the codon position in SEQ ID NO: 1, and the second letter is the amino acid in the allelic variant). Such variants can optionally be present individually or in any combination. The induced mutations E83Q, A90V, A76T, which enhance alpha-synuclein aggregation, can also be present individually or in combination with each other and/or human allelic variants E46K, A30P and A53T.

III. Lewy Body Diseases and Other Synucleinopathies

Lewy body diseases (LBDs), and in particular Parkinson's disease, are characterized by degeneration of the dopaminergic system, motor alterations, cognitive impairment, and formation of Lewy bodies (LBs) (McKeith et al., Neurology (1996) 47:1113-24). Lewy bodies are spherical protein deposits found in nerve cells. Their presence in the brain disrupts the brain's normal function interrupting the action of chemical messengers including acetylcholine and dopamine Lewy body diseases include Parkinson's disease (including idiopathic Parkinson's disease), diffuse Lewy body disease (DLBD) (also known as dementia with Lewy bodies (DLB)), Lewy body variant of Alzheimer's disease (LBV), and Alzheimer's and Parkinson disease comorbidity. DLBD shares symptoms of both Alzheimer's and Parkinson's disease. DLBD differs from Parkinson's disease mainly in brain region in which synucleinopathy is first observed. In DLBD, Lewy bodies form initially in the cortex. In Parkinson's disease, they originate in the midbrain and brain stem, e.g. the substantia nigra. In both disorders, the pathology progresses chronically to other regions of the brain in a spatiotemporal-defined fashion. Other Lewy body diseases include pure autonomic failure, Lewy body dysphagia, incidental LBD, and inherited LBD (e.g., mutations of the alpha-synuclein gene, PARK3 and PARK4). Multiple system atrophy (MSA; e.g., olivopontocerebellar atrophy, striatonigral degeneration and Shy-Drager syndrome) is a synucleinopathy in which oligodendrocytes are affected by intracellular deposition of alpha-synuclein concomitant with dysfunctional neuromuscular communication.

IV. Antibodies

A. Binding Specificity and Functional Properties

5C1 is an exemplary antibody for incorporation into the brain shuttles described herein. Its heavy and light chain mature variable regions are designated SEQ ID NO: 9 and SEQ ID NO: 24, respectively. Other antibodies that can be incorporated include antibodies binding to the same epitope as 5C1. Such antibodies can have similar functional properties, such as reducing neuronal aggregates of alpha-synuclein, improving cognitive function, and/or preserving synaptic density and/or dendritic density. Previous applications describing the 5C1 antibody and related antibodies include PCT Application No. PCT/US2013/63945 filed Oct. 8, 2013, and U.S. Application Nos. 61/711,204 filed Oct. 8, 2012, 61/719,281 filed Oct. 26, 2012, 61/840,432 filed Jun. 27, 2013, 61/872,366 filed Aug. 30, 2013, and U.S. application Ser. No. 14/049,169 filed Oct. 8, 2013, all of which are incorporated by reference in their entirety for all purposes.

Other antibodies having such binding specificity can be produced by immunizing mice or other animals (e.g., guinea pig, primate, rabbit, or rat) with alpha-synuclein or a fragment thereof (e.g., a fragment including amino acid residues 118-126, or a portion thereof). See Harlow & Lane, *Antibodies, A Laboratory Manual* (CSHP NY, 1988). Such an immunogen can be obtained from a natural source, by peptide synthesis, or by recombinant expression. The immunogen can optionally be administered fused or otherwise complexed with a carrier protein. The immunogen can optionally be administered with an adjuvant. Several types of adjuvant can be used as described below. Complete Freund's adjuvant followed by incomplete adjuvant can be used for immunization of laboratory animals. Rabbits or guinea pigs are typically used for making polyclonal antibodies. Mice are typically used for making monoclonal antibodies. The resulting antibodies can be screened for binding to alpha-synuclein, optionally in competition with 5C1. Antibodies can also be screened for their effect in: (1) alpha-synuclein transgenic rodent models subjected to behavioral assays, such as the Morris Water Maze (MWM) test or horizontal beam test, and/or immunological assays for the detection of alpha-synuclein, alpha-synuclein aggregation, synaptophysin, MAP2, and/or PSD95 in brain tissue; (2) rodent or other non-human animal models for a disease characterized by alpha-synuclein accumulation, using behavioral assays such as the Morris Water Maze (MWM) test or horizontal beam test and/or immunological assays for the detection of alpha-synuclein, alpha-synuclein aggregation, synaptophysin, MAP2, and/or PSD95 in brain tissue; and/or (3) humans with a condition associated with alpha-synuclein accumulation, using appropriate behavioral assays. Alternatively, or in addition to any of the foregoing approaches, antibodies can be screened against mutagenized forms of alpha-synuclein to identify an antibody showing the same or similar binding profile as 5C1 to a collection of mutational changes. The mutations can be systematic substitution with alanine (or serine if an alanine is present already) one residue at a time, or more broadly spaced intervals, throughout alpha-synuclein or through a section thereof in which the epitope is known to reside (e.g., residues 118-126).

Figure 6:
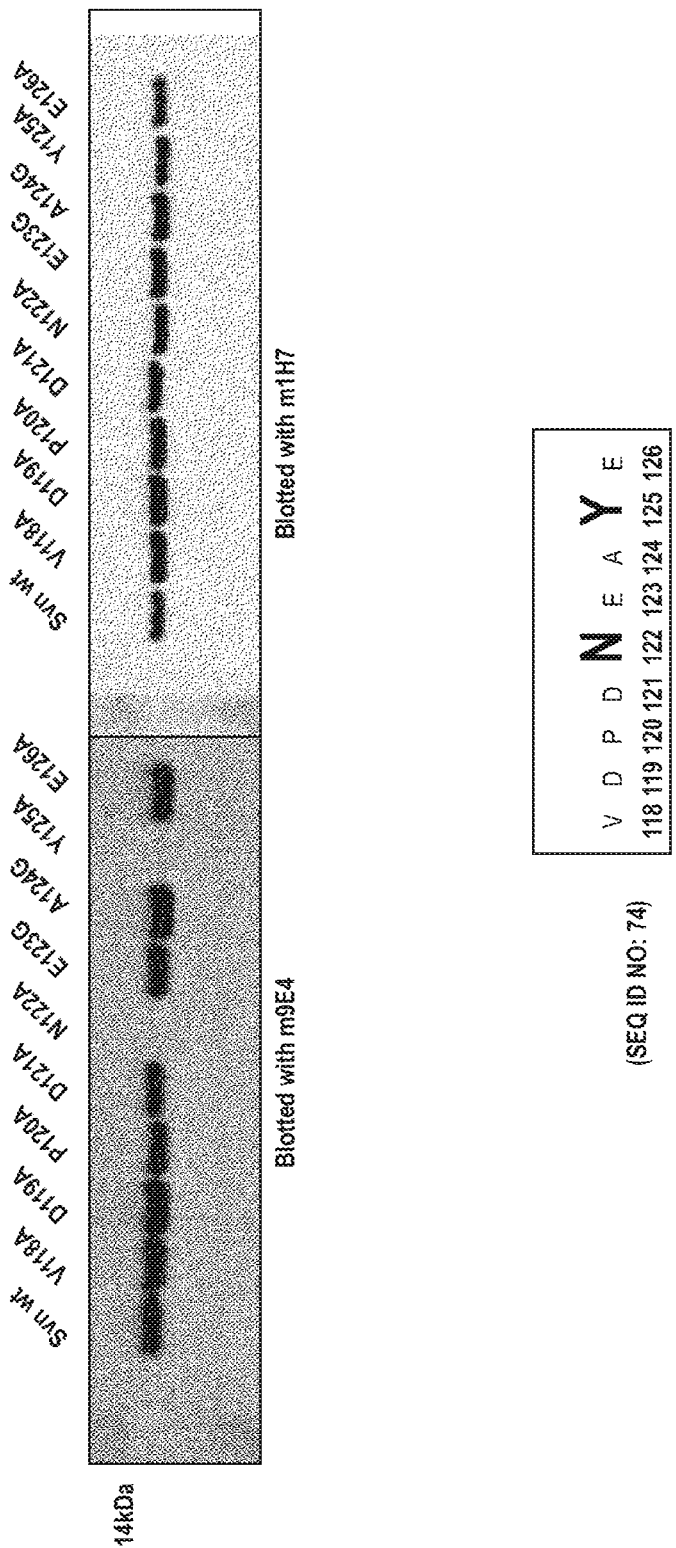
FIG. 6 shows the results of an alanine scanning mutagenesis experiment used to determine the epitope of alpha-synuclein bound by the 9E4 antibody. The upper portion of the figure shows Western blots of full-length alpha-synuclein (wild-type or individual point mutations of residues 118-126, as indicated) stained with 9E4 antibody (left panel) or control antibody 1H7 (right panel). The lower portion of the figure shows the epitope of alpha-synuclein bound by the 9E4 antibody.
Figure 7:
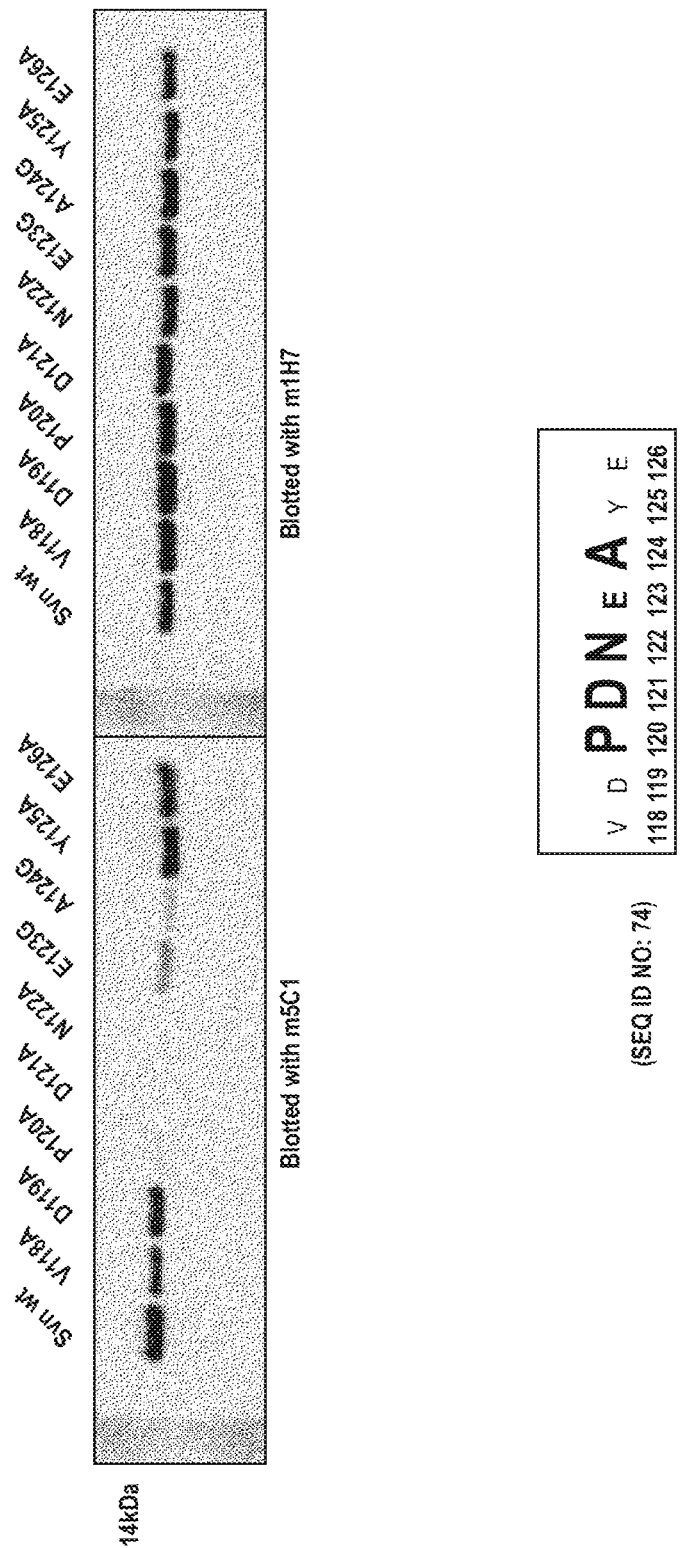
FIG. 7 shows the results of an alanine scanning mutagenesis experiment used to determine the epitope of alpha-synuclein bound by the 5C1 antibody. The upper portion of the figure shows Western blots of full-length alpha-synuclein (wild-type or individual point mutations in residues 118-126, as indicated) stained with 5C1 antibody (left panel) or control antibody 1H7 (right panel). The lower portion of the figure shows the epitope of alpha-synuclein bound by the 5C1 antibody.
Figure 8:
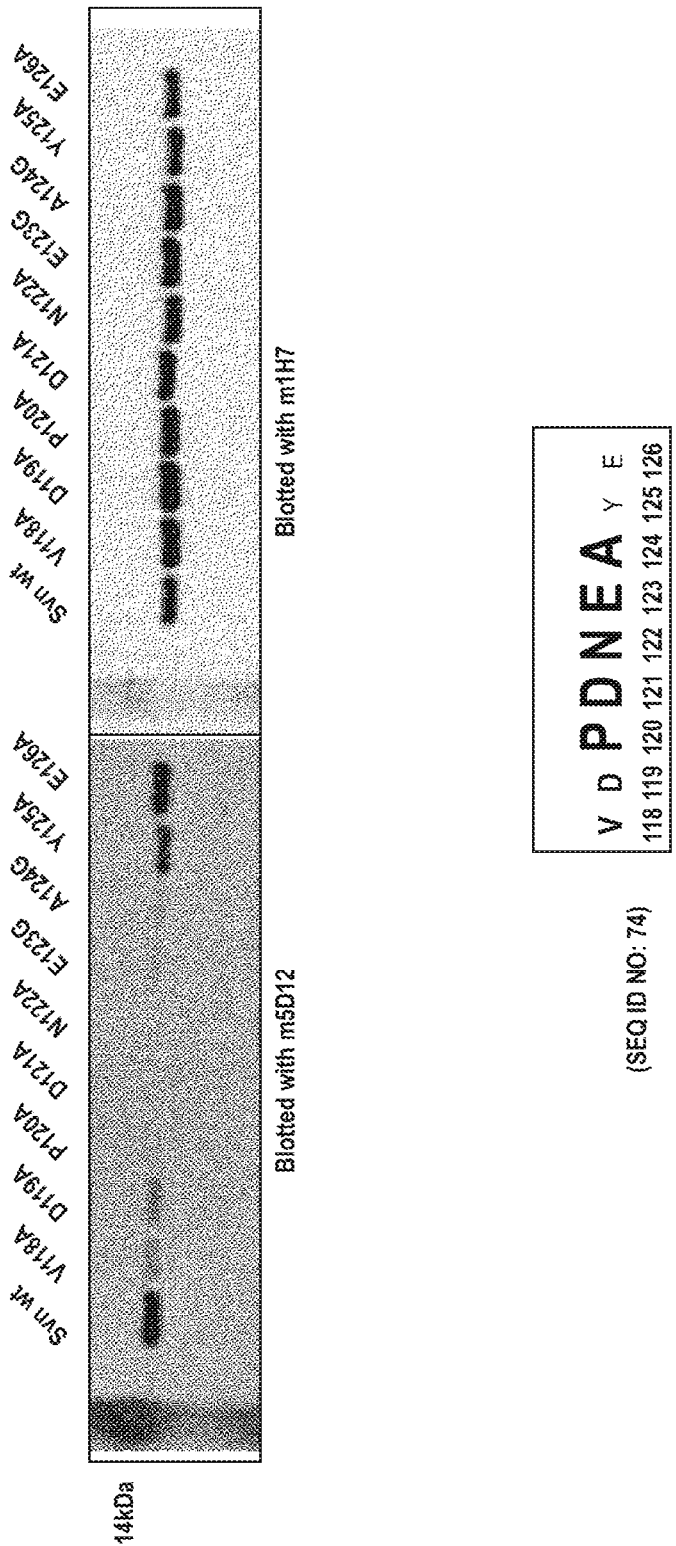
FIG. 8 shows the results of an alanine scanning mutagenesis experiment used to determine the epitope of alpha-synuclein bound by the 5D12 antibody. The upper portion of the figure shows Western blots of full-length alpha-synuclein (wild-type or individual point mutations in residues 118-126, as indicated) stained with 5D12 antibody (left panel) or control antibody 1H7 (right panel). The lower portion of the figure shows the epitope of alpha-synuclein bound by the 5D12 antibody.
Figure 9:
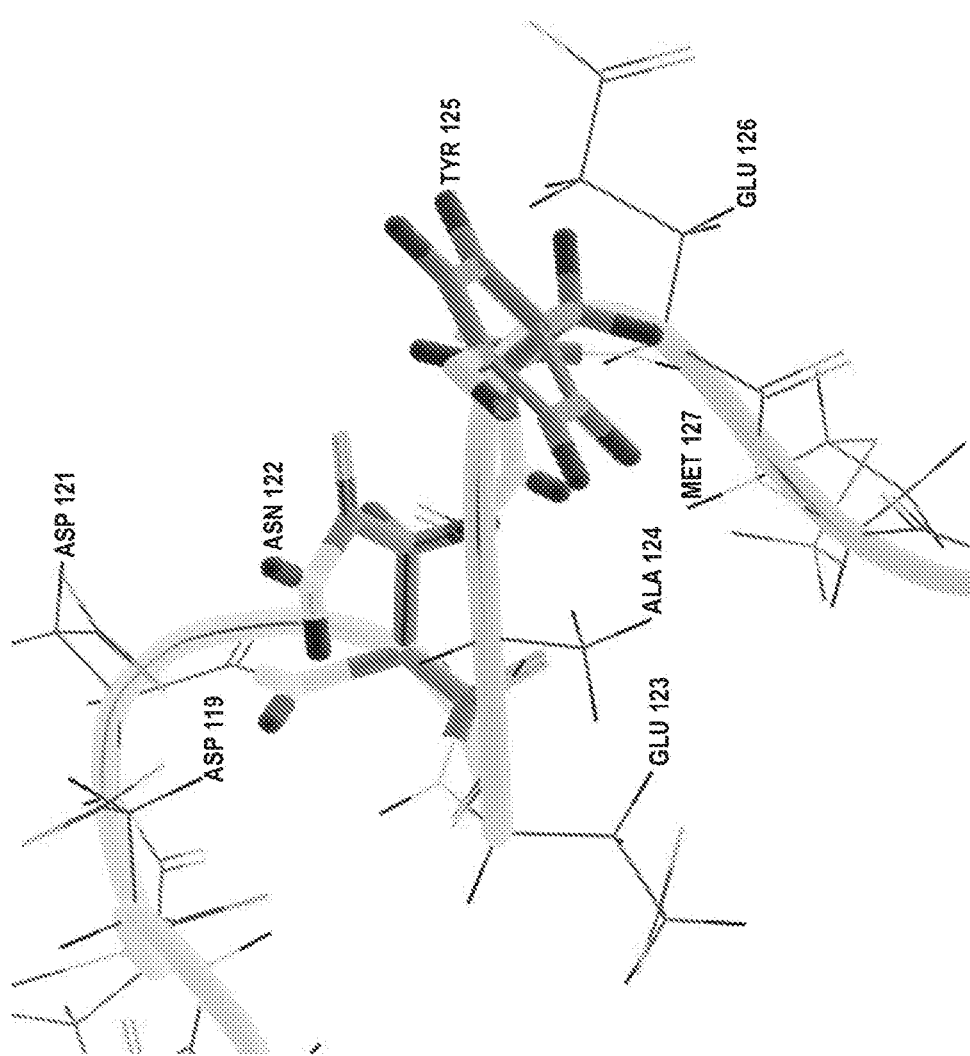
FIG. 9 depicts a ball and stick model of the amino acids of alpha-synuclein proximate to the binding sites of the 9E4, 5C1 and 5D12 antibodies.

FIGS. 6-8 and Example 6 characterize the epitope of 5C1 in comparison with two other antibodies binding within residues 118-126, namely 9E4 and 5D12. Alanine mutagenesis tests the effect of mutating individual amino acids, one at a time, in the 118-126 of alpha-synuclein. The profile of relative changes of binding affinity (in other words, contribution to binding) caused by mutation of different amino acids within residues 118-126 characterizes the epitope. For 5C1, mutagenesis of any of residues 120-122 has the greatest reduction of binding. Mutagenesis of residue 123 or 124 results in a significant reduction of binding, but not as much as at any of positions 120-122. Mutagenesis of residue 118, 119, 125 or residue 126 results in still less loss of binding affinity, essentially unchanged. For simplicity, the effects of mutagenesis can be approximately subdivided into three categories: essentially complete reduction of binding for residues 120-122 (indistinguishable from negative control), essentially no reduction of binding for residues 118, 119, 125 and 126 (indistinguishable from positive control) and intermediate reduction of binding affinity for residues 123 and 124. The epitope of 5C1 can thus be approximately characterized as a linear epitope consisting of or consisting essentially of residues 120-124 of SEQ ID NO: 1, with residues 120-122 making the greatest contribution to binding. Antibodies having the 5C1 epitope as characterized by any of the descriptions in this paragraph are provided. Some antibodies are characterized by an epitope consisting essentially of residues 120-122 and excluding residues 119-120 meaning that residues 120-122 each contribute more to binding than any other residue and residues 119 and 120 make no detectable contribution to binding (e.g., by the alanine scanning method of the example). Residues 123 and 124 may or may not make a minor contribution to binding in such antibodies.

Antibodies having the binding specificity of a selected murine antibody (e.g., 5C1) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for alpha-synuclein (e.g., at least $10^8$ $M^{-1}$ or at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for alpha-synuclein are selected. The resulting antibodies usually have the same or similar epitope specificity as the murine starting material.

Other antibodies can be obtained by mutagenesis of cDNA encoding the heavy and light chains of an exemplary antibody, such as 5C1. Accordingly, monoclonal antibodies that are at least 70%, 80%, 90%, 95%, 96%, 97%, 98% or 99% identical to 5C1 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention.

Antibodies having some or all (e.g., 3, 4, 5, and 6) CDRs entirely or substantially from 5C1 can be incorporated into the brain shuttles described herein. Such antibodies can include a heavy chain variable region that has at least two, and usually all three, CDRs entirely or substantially from the heavy chain variable region of 5C1 and/or a light chain variable region having at least two, and usually all three, CDRs entirely or substantially from the light chain variable region of 5C1. The antibodies can include both heavy and light chains. A CDR is substantially from a corresponding 5C1 CDR when it contains no more than 4, 3, 2 or 1 substitutions, insertions or deletions, except that CDRH2 (when defined by Kabat) can have no more than 6, 5, 4, 3, 2, or 1 substitutions, insertion or deletions. Such antibodies can have at least 70%, 80%, 90%, 95%, 96%, 97%, 98% or 99% identity to 5C1 in the amino acid sequence of the mature heavy and/or light chain variable regions and maintain its functional properties, and/or differ from 5C1 by a small number of functionally inconsequential amino acid substitutions (e.g., conservative substitutions), deletions, or insertions.

Some antibodies show similar functional activity to 5C1, e.g., reducing neuritic and/or axonal alpha-synuclein aggregates, reducing neuritic dystrophy, improving cognitive function, reversing, treating or inhibiting cognitive decline, and/or preserving or increasing synaptic density and/or dendritic density.

B. Chimeric and Veneered Antibodies

Chimeric and veneered forms of non-human antibodies, particularly 5C1, can be incorporated into the brain shuttles described herein.

A chimeric antibody is an antibody in which the mature variable regions of light and heavy chains of a non-human antibody (e.g., a mouse) are combined with human light and heavy chain constant regions. Typically, the light and heavy chain constant regions are of human origin, but the constant regions can originate from a different non-human species as needed (e.g., to facilitate testing of the non-human antibody in an appropriate animal model). Such antibodies substantially or entirely retain the binding specificity of the mouse antibody, and can be about two-thirds human sequence contributed by the human constant regions.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

C. Humanized Antibodies

Humanized 5C1 antibodies specifically bind to human alpha-synuclein. The affinity of some humanized antibodies (i.e., Ka) is can be, for example, within a factor of five or two of that of the murine 5C1 antibody. Some humanized antibodies have an affinity that is the same, within experimental error, as murine 5C1. Some humanized antibodies have an affinity greater than that of murine 5C1. Some humanized antibodies bind to the same epitope and/or compete with murine 5C1 for binding to human alpha-synuclein.

A humanized antibody is a genetically engineered antibody in which the CDRs from a non-human "donor" antibody (e.g., murine 5C1) are grafted into human "acceptor" antibody sequences (see, e.g., Queen, U.S. Pat. Nos. 5,530, 101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized 5C1 antibody is an antibody having some or all CDRs entirely or substantially from murine 5C1 and variable region framework sequences and constant regions, if present, entirely or substantially from human antibody sequences. Similarly a humanized heavy chain has at least two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region, respectively, when at least 85%, 90%, 95%, 96%, 97%, 98%, 99%, or 100% of corresponding residues defined by Kabat are identical.

Although humanized antibodies often incorporate all six CDRs (preferably as defined by Kabat) from a mouse antibody, they can also be made with less than all CDRs (at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

In some antibodies only part of the CDRs, namely the subset of CDR residues required for binding, termed the specificity determining residues (SDRs) (Kashmiri et al., Methods (2005) 36(1):25-34), are needed to retain binding in a humanized antibody. CDR residues not contacting antigen and not in the SDRs can be identified based on previous studies (for example one or more or all of residues H60-H65 in CDR H2 are sometimes not required), from regions of Kabat CDRs lying outside Chothia hypervariable loops (Chothia, J. Mol. Biol. 196:901 (1987)), by molecular modeling and/or empirically, or as described in Gonzales et al., Mol. Immunol. 41: 863, 2004. In such humanized antibodies, at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65%-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;
(2) is adjacent to a CDR region;
(3) otherwise interacts with a CDR region (e.g. is within about 6 Å of a CDR region), (e.g., identified by modeling the light or heavy chain on the solved structure of a homologous known immunoglobulin chain); or
(4) is a residue participating in the VL-VH interface.

Framework residues from classes (1)-(3) as defined by Queen, U.S. Pat. No. 5,530,101 are sometimes alternately referred to as canonical and vernier residues. Framework residues that help define the conformation of a CDR loop are sometimes referred to as canonical residues (Chothia and Lesk, J. Mol. Biol. 196:901-917 (1987), Thornton & Martin J. Mol. Biol., 263:800-815 (1996)). Framework residues that support antigen-binding loop conformations and play a role in fine-tuning the fit of an antibody to antigen are sometimes referred to as vernier residues (Foote & Winter, J. Mol. Biol. 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Humanized forms of the mouse 5C1 antibody can be incorporated into the brain shuttles described herein. The mouse antibody comprises mature heavy and light chain variable regions having amino acid sequences comprising SEQ ID NO: 9 and SEQ ID NO: 24, respectively. The invention provides five exemplified humanized mature heavy chain variable regions: H1, SEQ ID NO: 14; H2, SEQ ID NO: 15; H3, SEQ ID NO: 16; H4, SEQ ID NO: 17; and H5, SEQ ID NO: 18. The invention further provides four exemplified humanized mature light chain variable regions: L1, SEQ ID NO: 29; L2, SEQ ID NO: 30; L3, SEQ ID NO: 31; and L4, SEQ ID NO: 32. Antibodies include any permutations of these mature heavy and light chain variable regions are provided, i.e., H1L2, H1L3, H1L4, H2L1, H2L2, H2L3, H2L4, H3L1, H3L2, H3L3, H3L4, H4L1, H4L2, H4L3, H4L4, H5L1, H5L2, H5L3, or H5L4. The H4L3 variant, which includes eight heavy chain backmutations and five light chain backmutations, has an affinity to alpha-synuclein (as measured on a Biacore instrument) that is within a factor of two of the affinities of the murine and chimeric 5C1 antibodies. See Table 3, below. As measured by ELISA, the H4L3 variant has an affinity for alpha-synuclein that is substantially the same as a chimeric 5C1 antibody (within experimental error) and superior to the murine 5C1 antibody. See FIG. 5. In addition, the H5L3 variant, which includes six heavy chain backmutations and five light chain backmutations, provides an affinity to human alpha-synuclein (as measured on a Biacore instrument) that is within a factor of four the affinities of the murine and chimeric 5C1 antibodies. See Table 3, below. The H3L4 variant, which includes nine heavy chain backmutations and two light chain backmutations, also provides an affinity to human alpha-synuclein (as measured by ELISA) that is substantially the same a chimeric 5C1 antibody, within experimental error, and the H3L3 and H3L1 variants, which each include nine heavy chain backmutations and five and six light chain backmutations, respectively, provide affinities to alpha-synuclein that are superior to the murine 5C1 antibody (as measured by ELISA).

The invention provides variants of the H4L3 humanized 5C1 antibody in which the humanized mature heavy chain variable region shows at least 90%, 95%, 96%, 97%, 98%, or 99% identity to H4 (SEQ ID NO: 17) and the humanized mature light chain variable region shows at least 90%, 95%, 96%, 97%, 98%, or 99% sequence identity to L3 (SEQ ID NO: 31). In some such antibodies, at least one, two, three, four, five, six, seven, eight, nine, ten, eleven, twelve, or all thirteen of the backmutations in H4L3 are retained. The invention also provides variants of the H5L3 humanized 5C1 antibody in which the humanized mature heavy chain variable region shows at least 90%, 95%, 96%, 97%, 98%, or 99% identity to H5 (SEQ ID NO: 18) and the humanized mature light chain variable region shows at least 90%, 95%, 96%, 97%, 98%, or 99% sequence identity to L3 (SEQ ID NO: 31). In some such antibodies, at least one, two, three, four, five, six, seven, eight, nine, ten, or all eleven of the backmutations in H5L3 are retained Variants of the H3L4 humanized 5C1 antibody in which the humanized mature heavy chain variable region shows at least 90%, 95%, 96%, 97%, 98%, or 99% identity to H3 (SEQ ID NO: 16) and the humanized mature light chain variable region shows at least 90%, 95%, 96%, 97%, 98%, or 99% sequence identity to L4 (SEQ ID NO: 32) can be incorporated into the brain shuttles described herein. In some such antibodies, at least one, two, three, four, five, six, seven, eight, nine, ten, or all eleven of the backmutations in H3L4 are retained. In some antibodies, at least one of positions H11, H27, H30, H48, and H73 in the Vh region is occupied by L, Y, T, I, and K, respectively. In some antibodies, positions H11, H27, H30, H48, and H73 in the Vh region are occupied by L, Y, T, I, and K, respectively. In some antibodies, at least one of positions H67, H69, H91, and H94 in the Vh region is occupied by A, L, F, and S, respectively. In some antibodies, positions H67, H69, and H94 in the Vh region are occupied by A, L, and S, respectively, such as in version H4. In some antibodies, position H94 is occupied by S, such as in version H5. In some antibodies, positions H67, H69, H91, and H94 in the Vh region are occupied by A, L, F, and S, respectively, such as in version H3. In some antibodies, at least one of positions L12 and L14 in the Vk region is occupied by S. In some antibodies, positions L12 and L14 in the Vk region are both occupied by S, such as in versions L3 and L4. In some antibodies, at least one of positions L2, L45, L49, and L87 in the Vk region is occupied by V, K, N, and F, respectively. In some antibodies, positions L2, L49, and L87 in the Vk region are occupied by V, N, and F, respectively, such as in version L3. In some antibodies, positions L2, L45, L49, and L87 in the Vk region are occupied by V, K, N, and F, respectively, such as in version L1. The CDR regions of such humanized antibodies can be identical or substantially identical to the CDR regions of H4L3 or H5L3, which are the same as those of the mouse donor antibody. The CDR regions can be defined by any conventional definition (e.g., Chothia) but are preferably as defined by Kabat.

One possibility for additional variation in humanized 5C1 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution or even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutation. For example, when using a heavy chain acceptor sequence in which position H11 is already occupied by L, H48 is already occupied by I, and/or H73 is already occupied by K, the corresponding backmutation(s) is not necessary. Similarly, when using a light chain acceptor sequence in which position L12 and/or L14 is occupied by S, the corresponding backmutation(s) is not necessary.

Humanized antibodies in which the mature light and heavy chain variable regions shows at least 90%, 95%, 96%, 97%, 98%, or 99% sequence identity to the mature light and heavy chain variable regions of the humanized 5C1 H1L1, H1L2, H1L3, H1L4, H2L1, H2L2, H2L3, H2L4, H3L1, H3L2, H3L3, H4L1, H4L2, H4L4, H5L1, H5L2, or H5L4 can be incorporated into the brain shuttles described herein. The CDR regions of such humanized antibodies can be identical or substantially identical to those of the mouse donor antibody. The CDR regions can be defined by any conventional definition (e.g., Chothia) but are preferably as defined by Kabat.

D. Selection of Constant Region

The heavy and light chain variable regions of chimeric, humanized, veneered, or human antibodies can be linked to at least a portion of a constant region sufficient to interact with an Fc receptor. The constant region is typically human, but a non-human constant region can be selected as needed.

The choice of constant region depends, in part, on whether antibody-dependent complement and/or cellular mediated cytotoxicity is desired. For example, human isotopes IgG1 and IgG3 have complement-mediated cytotoxicity whereas human isotypes IgG2 and IgG4 have poor or no complement-mediated cytotoxicity. Human IgG1 and IgG3 also induce stronger cell-mediated effector functions than human IgG2 and IgG4. A human IgG1 constant region suitable for inclusion in the antibodies can have the sequence of SEQ ID NO: 38. Light chain constant regions can be lambda or kappa. A human kappa light chain constant region suitable for inclusion in the antibodies can have the sequence of SEQ ID NO: 52. The N-terminal arginine of SEQ ID NO: 52 can be omitted, in which case the kappa light chain constant region has the amino acid sequence of SEQ ID NO: 40. Antibodies can be expressed as tetramers containing two light and two heavy chains, as separate heavy chains, as separate light chains, as Fab, Fab', F(ab')$_2$, or Fv fragments, or as single chain antibodies in which heavy and light chain variable regions are linked through a spacer.

Human constant regions show allotypic variation and isoallotypic variation between different individuals. That is, the constant regions can differ in different individuals at one or more polymorphic positions. Isoallotypes differ from allotypes in that sera recognizing an isoallotype binds to a non-polymorphic region of one or more other isotypes. Thus, for example, another heavy chain constant region is of the IgG1 G1m3 allotype and has the amino acid sequence of SEQ ID NO: 66. Another heavy chain constant region of the IgG1 G1m3 allotype has the amino acid sequence of SEQ ID NO: 75. Reference to a human constant region includes a constant region with any natural allotype or any permutation of residues occupying polymorphic positions in natural allotypes or up to 3, 5 or 10 substitutions for reducing or increasing effector function as described below.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduces affinity for Fcγ receptors, particularly FcγRI receptor (see, e.g., U.S. Pat. No. 6,624,821). An alanine substitution at positions 234, 235 and 237 of human IgG1 can be used for reducing effector functions. Optionally, positions 234, 236 and/or 237 in human IgG2 are substituted with alanine and position 235 with glutamine (see, e.g., U.S. Pat. No. 5,624,821). In some antibodies, a mutation at one or more of positions 241, 264, 265, 270, 296, 297, 322, 329, and 331 by EU numbering of human IgG1 is used. In some antibodies, a mutation at one or more of 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine, such as in SEQ ID NO: 75. In some antibodies, the isotype is human IgG2 or IgG4.

E. Human Antibodies

Human antibodies against alpha-synuclein are provided by a variety of techniques described below. Some human antibodies are selected by competitive binding experiments, or otherwise, to have the same or overlapping epitope specificity as 5C1. Human antibodies can also be screened for a particular epitope specificity by using only a fragment of alpha-synuclein (e.g., amino acid residues 118-126) as the immunogen, and/or by screening antibodies against a collection of deletion mutants of alpha-synuclein. One technique for producing human antibodies is trioma methodology (Oestberg et al., Hybridoma 2:361-367 (1983); Oestberg, U.S. Pat. No. 4,634,664; and Engleman et al., U.S. Pat. No. 4,634,666). Another technique involves immunizing transgenic mice expressing human immunoglobulin genes, such as the XenoMouse®, AlivaMab Mouse or Veloceimmune mouse (see, e.g., Lonberg et al., W093/1222, U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, and WO 91/10741). Another technique is phage display (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332). In these methods, libraries of phage are produced in which members display different antibodies on their outer surfaces. Antibodies are usually displayed as Fv or Fab fragments. Phage displaying antibodies with a desired specificity are selected by affinity enrichment to an alpha-synuclein peptide or fragment thereof. Another technique is to sequence DNA from human B cells according to the general protocols outlined in Reddy et al., Nat. Biotechnol. 2010 Sep. 28(9):965-9 (Epub 2010 Aug. 29), and US 20110053803, 20100099103, 20100291066, 20100035763, and 20100151471. Briefly, B cells can be obtained from a human suspected of having anti-alpha-synuclein antibodies, e.g., a human immunized with alpha-synuclein, fragments thereof, longer polypeptides containing alpha-synuclein or fragments thereof, or anti-idiotypic antibodies. The mRNA of the antibodies from B cells is then reverse transcribed into cDNA and sequenced using, e.g., 454 sequencing technology. After obtaining the sequences of the chains from each antibody, the chains can be paired together (e.g., using bioinformatics), cloned, expressed, and screened for desired properties.

F. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter, "Schenk"). The sequences from multiple, independently-derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions. Exemplary sequences encoding human constant regions include SEQ ID NOS: 37 and 72, which encode the human IgG1 constant regions represented by SEQ ID NOS: 38 and 66, respectively, and SEQ ID NOS: 39 and 71, which encode the human kappa light chain constant regions represented by SEQ ID NOS: 40 and 52, respectively.

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant nucleic acid constructs typically include an expression control sequence operably linked to the coding sequences of antibody chains, including naturally associated or heterologous expression control element(s), such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the cross reacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host useful for cloning the DNA sequences encoding the polypeptides disclosed herein. Microbes, such as yeast are also useful for expression. *Saccharomyces* is a yeast host, with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a host cell for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed, and include CHO cell lines, various COS cell lines, HeLa cells, L cells, human embryonic kidney cell (HEK293 cells), and myeloma cell lines. The cells can be nonhuman Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., J. Immunol. 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assays, such as ELISA or Biacore. A selected clone can then be banked in multiple vials and stored frozen for subsequent use.

Once expressed, antibodies can be purified according to standard procedures, including protein A capture, HPLC purification, column chromatography, gel electrophoresis, and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464, 6,114,148, 6,063,598, 7,569,339, W02004/050884, W02008/012142, W02008/012142, W02005/019442, W02008/107388, and W02009/027471, and U.S. Pat. No. 5,888,809).

G. Antibody Screening Assays

Antibodies can be subject to several screens including binding assays, functional screens, screens in animal models of diseases associated with alpha-synuclein deposits, and clinical trials. Binding assays test for specific binding and, optionally, affinity and epitope specificity to alpha-synuclein (or a fragment thereof, such as amino acid residues 118-126). Such screens are sometimes performed in competition with an exemplary antibody such as 5C1. Optionally, either the antibody or alpha-synuclein target is immobilized in such assay. Functional assays can be performed in cellular models including cells naturally expressing alpha-synuclein or transfected with DNA encoding alpha-synuclein or a fragment thereof. Suitable cells include neuronal cells. Cells can be screened for reduced levels of alpha-synuclein (e.g., by Western blotting or immunoprecipitation of cell extracts or supernatants), reduced levels of aggregated alpha-synuclein (e.g., by immunohistochemical and/or confocal methods), and/or reduced toxicity attributable to alpha-synuclein.

Animal model screens test the ability of the antibody to therapeutically or prophylactically treat signs or symptoms in an animal model simulating a human disease associated with alpha-synuclein deposits, such as a Lewy body disease. Suitable signs or symptoms that can be monitored include motor balance, coordination, and cognitive deficits. The extent of impairment can be determined by comparison with an appropriate control, such as motor balance, coordination, or cognitive deficiency in control animals that have received a control antibody (e.g., an isotype matched control antibody), a placebo, or no treatment at all. Transgenic or other animal models of Lewy body diseases can express a human alpha-synuclein transgene. To facilitate testing in animal models, antibodies having a constant region appropriate for the animal model can be used. It can be concluded that a humanized version of an antibody will be effective if the corresponding mouse antibody or chimeric antibody is effective in an appropriate animal model and the humanized antibody has similar binding affinity (e.g., by a factor of 1.5, 2, or 3, within experimental error).

Clinical trials test for safety and efficacy in a human having a disease associated with alpha-synuclein deposits.

H. Nucleic Acids

Also provided are nucleic acids encoding any of the heavy and light chains described above. Typically, the nucleic acids also encode a signal peptide fused to the mature heavy and light chains. Suitable example of signal peptides include amino acid residues 1-19 of SEQ ID NO: 6 (encoded by nucleotides 1-57 of SEQ ID NO: 5) and amino acid residues 1-19 of SEQ ID NO: 8 (encoded by nucleotides 1-57 of SEQ ID NO: 7). Coding sequences of nucleic acids can be in operable linkage with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

V. Blood-Brain Barrier Shuttles

An anti-alpha-synuclein antibody as disclosed herein can be coupled to a monovalent binding entity capable of binding to a blood-brain barrier receptor, thus forming a blood-brain barrier shuttle. The coupling can be direct or through linker(s). The coupling can be such as to form a contiguous fusion protein comprising one of the chains, often the heavy chain of the anti-alpha-synuclein antibody, an optional linker, and the monovalent binding entity, with the light chain of the anti-alpha-synuclein antibody complexed to the heavy chain. Chemical coupling can also be used between the anti-alpha-synuclein antibody and monovalent binding entity. Blood-brain barrier shuttles are described in Bohrmann et al., WO 2014/033074, incorporated by reference in its entirety for all purposes.

A brain effector entity is a molecule or compound that is to be transported to the brain across the blood-brain barrier by the blood-brain barrier shuttle. The brain effector entity typically has a characteristic therapeutic activity that is desired to be delivered to the brain. When the anti-alpha-synuclein antibodies disclosed herein are part of a blood-brain barrier shuttle, they are referred to as brain effector entity antibodies. The brain effector entity antibodies, alone or in combination with other compounds, make up the brain effector entities.

Coupling of the anti-alpha-synuclein antibodies to monovalent binding entities in a blood-brain barrier shuttle can facilitate transport of the antibodies across the blood-brain barrier. Assays for evaluating uptake of systemically administered blood-brain barrier shuttles and other activities of the blood-brain barrier shuttles are disclosed in WO 2014/033074. Concentration within the parenchyma space of the central nervous system can also be measured. For example, microdialysis or the capillary depletion method can be combined with ELISA or radioactivity measurements of labeled blood-brain barrier shuttles.

A. Blood-Brain Barrier Receptors

The blood-brain barrier (BBB) is the physiological barrier between the peripheral circulation and the brain and spinal cord. It is formed by tight junctions within the brain capillary endothelial plasma membranes, creating a tight barrier that restricts the transport of molecules into the brain, including even very small molecules such as urea (60 Daltons). Blood-brain barrier (BBB) collectively refers to the BBB within the brain, the blood-spinal cord barrier within the spinal cord, and the blood-retinal barrier within the retina, which are contiguous capillary barriers within the central nervous system. The BBB also encompasses the blood-CSF barrier (choroid plexus) where the barrier is comprised of ependymal cells rather than capillary endothelial cells.

A blood-brain barrier receptor (R/BBB) is an extracellular membrane-linked receptor protein expressed on brain endothelial cells that is capable of transporting molecules across the BBB or being used to transport exogenously administered molecules. Examples of blood-brain barrier receptors include: transferrin receptor (TfR) (e.g., UniProt Accession Number P02786), insulin receptor (e.g., UniProt Accession Number P06213), insulin-like growth factor receptor (IGF-R) (e.g., UniProt Accession Number P08069), low density lipoprotein receptors including low density lipoprotein receptor-related protein 1 (LRP1) (e.g., UniProt Accession Number Q07954) and low density lipoprotein receptor-related protein 8 (LRP8) (e.g., UniProt Accession Number Q14114), and heparin-binding epidermal growth factor-like growth factor (HB-EGF) (e.g., UniProt Accession Number Q99075).

A transferrin receptor is a transmembrane glycoprotein with a molecular weight of about 180,000 Daltons that is composed of two disulfide-bonded subunits (each with an apparent molecular weight of about 90,000 Daltons) involved in iron uptake in vertebrates. For example, a transferrin receptor can be a human TfR comprising the amino acid sequence described in Schneider et al., Nature 311:675-678 (1984).

B. Monovalent Binding Entities

A monovalent binding entity is a molecule able to bind specifically and in a monovalent binding mode to a blood-brain barrier receptor (i.e., 1:1 binding molecule to receptor). Blood-brain barrier receptor antigens can be used for production of, or screening for, monovalent binding entities. Such antigens can be, for example, a soluble form of a blood-brain barrier receptor or a portion thereof (e.g., the extracellular domain) containing a desired epitope. Alternatively, cells expressing a blood-brain barrier receptor at their cell surface can be used to generate, or screen for, monovalent binding entities.

Various techniques are available for determining binding of a monovalent binding entity to a blood-brain barrier receptor. One such assay is an enzyme linked immunosorbent assay (ELISA) in which binding of a monovalent binding entity to a blood-brain barrier receptor is measured after coating plates with recombinant blood-brain barrier receptor and incubating the plates with a sample including the monovalent binding entity.

Figure 10:
FIG. 10 depicts the "knob" 5C1H4-HuIgG1-scFab(8D3) heavy chain fusion protein.

The monovalent binding entity can be a protein, polypeptide, or peptide, such as a blood-brain barrier receptor ligand. The monovalent binding entity can be an antibody fragment such as a Fab, Fab', Fv, or VHH fragment, or a single-chain antibody molecule such as a single-chain Fab or scFv. The single chain Fab (scFab) format is described in Hust et al., BMC Biotechnol. 7:14 (Mar. 8, 2007). A scFab includes the VH and CH1 regions of a heavy chain (i.e., the portion of the heavy chain that is included in a Fab fragment; also known as the Fd fragment) connected via a linker to a light chain including VL and CL regions. In some instances, the linker joins the N-terminus of the VH region to the C-terminus of the CL region (see FIG. 10). Optionally, one or more cysteines which in an intact antibody form disulfides between the CH1 region of the heavy chain and the constant region of the light chain can be omitted. A monovalent binding entity that comprises one and only one scFab is referred to as having a single Fab (sFab). The monovalent binding entity can be a scaffold protein engineered using technologies such as phage display or immunization. The blood-brain barrier shuttle can be characterized by the presence of a single unit of a monovalent binding entity (i.e., the blood-brain shuttle comprises no more than one unit of the monovalent binding entity).

The monovalent binding entity can also comprise a CH2-CH3 Ig domain and a sFab directed to a blood-brain barrier receptor. The sFab can be coupled to the C-terminal end of the CH2-CH3 Ig domain by a linker. A CH2-CH3 Ig entity is a protein entity derived from immunoglobulin CH2 or CH3 domains. The CH2-CH3 Ig entity can comprise two CH2-CH3 polypeptides forming a dimer. The immunoglobulin can be IgG, IgA, IgD, IgE or IgM. A CH2-CH3 Ig entity can include native CH2-CH3 domain sequences and/or variant CH2-CH3 domain sequences. The CH2-CH3 Ig entity can be derived from an IgG immunoglobulin, in which case it is referred to as a CH2-CH3 IgG entity. For example, a CH2-CH3 Ig entity can be from a human heavy chain CH2-CH3 IgG domain that extends from Cys226 or Pro230 to the carboxyl-terminus of the heavy chain. The C-terminal lysine (Lys447) of the Fc region can be present or absent. Unless otherwise specified, numbering of amino acid residues in the CH2-CH3 domain region or constant region is according to the EU numbering system, also called the EU index, as described in Kabat et al., *Sequences of Proteins of Immunological Interest*, 5th Ed. Public Health Service, National Institutes of Health, Bethesda, Md. (1991).

Some monovalent binding entities are directed to a transferrin receptor. For example, a monovalent binding entity can comprise one scFab (i.e., a sFab) directed to a transferrin receptor. In some instances, the sFab recognizes an epitope in the transferrin receptor comprising an amino acid sequence within SEQ ID NO: 43, SEQ ID NO: 44, and/or SEQ ID NO: 45. Some monovalent binding entities directed to a transferrin receptor are derived from the mouse 8D3 anti-transferrin antibody described in Boado et al., Biotechnology and Bioengineering 102:1251-1258 (2009) and WO 2014/033074. For example, the monovalent binding entity can comprise a scFab of the 8D3 antibody (e.g., SEQ ID NO: 60), as in Example 7 (see also FIG. 13).

Monovalent binding mode refers to specific binding to a blood-brain barrier receptor in which the interaction between the monovalent binding entity and the blood-brain barrier receptor takes place through one single epitope. The single epitope interaction point in monovalent binding mode can prevent any dimerization or multimerization of the blood-brain barrier receptor. Monovalent binding mode can also prevent significant alteration of the intracellular sorting of the blood-brain barrier receptor. Various assays for measuring monovalent binding mode are available, including Scatchard assays and surface plasmon resonance techniques (e.g., using Biacore) and in vivo investigations as described in WO 2014/033074. Epitope mapping and X-ray structure determinations can also be used to test a monovalent binding entity for its single antigen binding activity towards a blood-brain barrier receptor.

One way of achieving monovalent binding mode when the brain effector entity antibody includes a heavy chain is to couple the monovalent binding entity to only one of the heavy chains (e.g., the Fc region of the heavy chain). This can be accomplished through use of the "knobs-into-holes" antibody engineering strategy described in Ridgway et al., Protein Engineering 9(7): 617-621 (1996) and Carter et al., Immunotechnology 2(1):73-73(1) (1996). For example, CH3 chains can be engineered for heterodimerization through this method by creating "knobs" by replacing small amino acid side chains at the interface between CH3 domains with larger amino acid side chains, and by creating "holes" by replacing large side chains with smaller ones.

In some blood-brain barrier shuttles, the first heavy chain of a brain effector entity antibody comprises a first dimerization module, and the second heavy chain of the brain effector entity antibody comprises a second dimerization module, thereby allowing heterodimerization of the two heavy chains. For instance, the first dimerization module can comprise "knobs," and the second dimerization module can comprise "holes" to receive the knobs according to the "knobs-into-holes" strategy. A knob or protuberance is a term of art for an amino acid or a small cluster of spatially close together amino acids of an antibody chain having at least one side chain that projects outward from the surface of the chain. Such a knob may project or insert into a hole or cavity, i.e., an indentation or pocket, in the interface of another antibody chain so as to make favorable contacts and stabilize the interaction between the chains; the hole is then said to receive the knob.

The "knobs-into-holes" strategy can be used in this manner to achieve monovalent binding by coupling the monovalent binding entity to the first dimerization module but not the second dimerization module. For example, the first dimerization module can be a fusion protein comprising the following elements in the following order: (1) the heavy chain variable region of 5C1 H4; (2) a human IgG1 constant region; (3) a linker; (4) the light chain variable region of the mouse 8D3 anti-transferrin antibody; (5) a human Ig kappa light chain constant region; (6) a linker; (7) the variable heavy chain region of the mouse 8D3 anti-transferrin antibody; and (8) a human IgG1 CH1 heavy chain domain. The second dimerization module can then be a fusion protein comprising the following elements in the following order: (1) the heavy chain variable region of 5C1 H4 and (2) a human IgG1 constant region. See Example 7 and FIGS. 10-12. When the first and second dimerization modules heterodimerize, only a single monovalent binding entity will be present.

C. Coupling of Entities of the Blood-Brain Barrier Shuttle

Coupling of different entities on the blood-brain barrier shuttle can be achieved through direct covalent conjugation. For example, such conjugation can couple an anti-alpha-synuclein antibody disclosed herein and a monovalent binding entity. Direct conjugation can be achieved by construction of a protein fusion through genetic fusion of the two genes encoding the monovalent binding entity and the brain effector entity so that they are expressed as a single protein. Direct conjugation can also be achieved by formation of a covalent bond between a reactive group on the monovalent binding entity and a corresponding group or acceptor on the brain effector entity. Direct conjugation can also be achieved by modification (e.g., genetic modification) of one of the two molecules to be conjugated to include a reactive group (e.g., a sulfhydryl group or a carboxyl group) that forms a covalent attachment to the other molecule to be conjugated under appropriate conditions. For example, a molecule (e.g., an amino acid) with a desired reactive group (e.g., a cysteine residue) can be introduced into the monovalent binding entity and a disulfide bond can then be formed with the brain effector entity antibody. Methods for covalent conjugation of nucleic acids to proteins are also known (i.e., photocrosslinking, see, e.g., Zatsepin et al., Russ. Chem. Rev. 74:77-95 (2005))

Covalent conjugation may also be performed using a variety of linkers. Such linkers can covalently connect different entities in the blood-brain barrier shuttle. Some linkers connect the brain effector entity to the monovalent binding entity. The monovalent binding entity can be coupled to the C-terminal end of the brain effector entity by a linker. For instance, a monovalent binding entity can be coupled by a linker to the C-terminal end of the Fc region of a heavy chain of a brain effector entity antibody. In some cases, the Fc region of the heavy chain of the brain effector entity antibody to which the monovalent binding entity is linked can be truncated compared to a full-length Fc region.

Linkers can also connect other entities of the blood-brain barrier shuttle. For example, in some blood-brain barrier shuttles, the monovalent binding entity can comprise a CH2-CH3 Ig entity and a sFab directed to a blood-brain barrier receptor. In such blood-brain barrier shuttles, a linker can connect the sFab to the C-terminal end of the CH3-CH2 Ig entity. For example, such blood-brain barrier shuttles can have a first linker connecting the brain effector entity to the N-terminal end of the CH2-CH3 Ig entity and a second linker connecting the sFab to the C-terminal end of the CH2-CH3 Ig domain. The first and second linkers can be the same or different.

In another example of a blood-brain barrier shuttle with more than one linker, the monovalent binding entity can comprise a scFab. In some such blood-brain barrier shuttles, the Fc region of the IgG heavy chain of the brain effector entity antibody is coupled at its C-terminal end to the scFab. For example, such a blood-brain barrier shuttle could include the following components connected in the following order: (1) an IgG heavy chain of the brain effector entity antibody; (2) a linker coupling the C-terminal end of the Fc region of the IgG heavy chain to the N-terminal end of the variable light chain domain of the scFab; (3) the variable light chain domain and a C-kappa light chain domain of the scFab; (4) a linker coupling the C-terminal end of the C-kappa light chain domain of the scFab to the N-terminal end of the variable heavy chain domain of the scFab; and (5) the variable heavy chain domain of the scFab and an IgG CH1 heavy chain domain. The first and second linkers can be the same or different.

Linkers can be single-chain peptide linkers. Some such linkers can include one to twenty amino acids joined by peptide bonds. The amino acids can be selected from the twenty naturally occurring amino acids. In some instances, one or more of the amino acids can be selected from glycine, alanine, proline, asparagine, glutamine, and lysine. Other such linkers can include at least 20 amino acids or at least 25 amino acids. For example, a linker can have a length of 32 to 50 amino acids. Some linkers have the formula of $(G_xS)_nG_m$, where G=glycine and S=serine. For some linkers, x=3; n=8, 9 or 10; and m=0, 1, 2 or 3. For other linkers, x=4; n=6, 7 or 8; and m=0, 1, 2 or 3. For yet other linkers, x=4; n=6 or 7; and m=0, 1, 2 or 3. For yet other linkers, x=4, n=7, and m=2. Three representative linkers have the formulas $(G_4S)_4$ (SEQ ID NO: 42), $(G_4S)_6G_2$ (SEQ ID NO: 41), and $G_3S(G_4S)_3$ (SEQ ID NO: 73).

Coupling of different entities on the blood-brain barrier shuttle (e.g., an anti-alpha-synuclein antibody disclosed herein and a monovalent binding entity) can also be through conjugation using a variety of chemical linkers. For example, the monovalent binding entity and the brain effector entity can be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). The linker can be a cleavable linker, facilitating release of the brain effector entity upon delivery to the brain. For example, an acid-labile linker, peptidase-sensitive linker, photolabile linker, dimethyl linker, or disulfide-containing linker can be used (see, e.g., Chari et al., Cancer Res. 52: 127-131 (1992); U.S. Pat. No. 5,208,020).

Different entities in the blood-brain barrier shuttle can also be coupled with a label. Such labels can be markers used for detection or imaging. Examples of such labels include radiolabels, fluorophores, chromophores, and affinity tags. Such labels can be radiolabels used for medical imaging (e.g., technetium-99m (tc99m) or iodine-123 (1123)), or spin labels used for nuclear magnetic resonance (NMR) imaging or magnetic resonance imaging (MRI), such as iodine-123, iodine-131, indium-111, fluorine-19, carbon-13, nitrogen-15, oxygen-17, gadolinium, manganese, or iron.

D. Nucleic Acids

The invention further provides nucleic acids encoding any of the blood-brain barrier shuttles described above. Coding sequences of nucleic acids can be in operable linkage with regulatory sequences to ensure expression of the coding sequences, such as a promoter, enhancer, ribosome binding site, transcription termination signal, and the like. The nucleic acids can occur in isolated form or can be cloned into one or more vectors. For example, nucleic acids encoding SEQ ID NOS: 53, 57, and 59 can be cloned into one, two, three, or more vectors. Similarly, nucleic acids encoding SEQ ID NOS: 55, 58, and 59 can be cloned into one, two, three, or more vectors. The nucleic acids can be synthesized by, for example, solid state synthesis or PCR of overlapping oligonucleotides. Nucleic acids encoding heavy and light chains of the brain effector entity antibody can be joined as one contiguous nucleic acid, e.g., within an expression vector, or can be separate, e.g., each cloned into its own expression vector. Nucleic acids encoding two different versions of the heavy chain of the brain effector entity antibody (e.g., a first dimerization module and a second dimerization module, or a "knob" version and a "hole" version according to the "knobs-into-holes" strategy) can be cloned into one expression vector or separate expression vectors. Nucleic acids encoding the monovalent binding entity can be cloned into one expression vector or multiple expression vectors. Nucleic acids encoding all or some of the brain effector entity and all or some of the monovalent binding entity can be cloned into one expression vector or separate expression vectors.

E. Expression of Blood-Brain Barrier Shuttles

Blood-brain barrier shuttles can be produced by recombinant expression. Recombinant nucleic acid constructs typically include an expression control sequence operably linked to the coding sequences of components of the blood-brain barrier shuttles, including naturally associated or heterologous expression control element(s), such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the blood-brain barrier shuttles.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

Suitable host cells useful for expression of the blood-brain barrier shuttle nucleic acids sequence are described in section IV.F and include *E. coli*, microbes such as yeast, and mammalian cells. The vectors containing the DNA segments of interest can be transferred into the host cells using the methods described in Section IV.F.

Having introduced vector(s) encoding the components of the blood-brain barrier shuttles into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Blood-brain barrier shuttles produced by single cell clones can also be tested for turbidity, filtration properties, PAGE, IEF, UV scan, HP-SEC, carbohydrate-oligosaccharide mapping, mass spectrometry, and binding assays, such as ELISA or Biacore. A selected clone can then be banked in multiple vials and stored frozen for subsequent use.

Once expressed, blood-brain barrier shuttles can be purified according to standard procedures, including protein A capture, HPLC purification, column chromatography, gel electrophoresis, and the like (see generally, Scopes, *Protein Purification* (Springer-Verlag, NY, 1982)).

VI. Therapeutic Applications

The invention provides methods of treating or effecting prophylaxis of synucleinopathies, such as Lewy body diseases (LBDs) or MSA, in patients suffering from or at risk of such a disease. Patients amenable to treatment include individuals at risk of disease but not showing symptoms, as well as patients presently showing symptoms or the early warning signs of synucleinopathies, for example, EEG slowing, neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia) and miscellaneous other signs and symptoms (fatigue, diplopia, blurred vision, seborrhea, weight loss/gain). Therefore, the present methods can be administered prophylactically to individuals who have a known genetic risk of a LBD. Such individuals include those having relatives who have experienced this disease and those whose risk is determined by analysis of genetic or biochemical markers. Genetic markers of risk toward Parkinson's disease include mutations in the alpha-synuclein gene, particularly duplications or triplications of the alpha-synuclein gene and point mutations at positions 30 and 53 of the alpha-synuclein protein, or mutations in the LRRK2, GBA, Parkin, UCHL1, and CYP2D6 genes. Individuals presently suffering from Parkinson's disease can be recognized from its clinical manifestations including resting tremor, muscular rigidity, bradykinesia and postural instability.

In asymptomatic patients, treatment can begin at any age (e.g., 10, 20, or 30 years of age). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to a therapeutic agent (e.g., a truncated form of alpha-synuclein peptide) over time. If the response falls, a booster dosage is indicated.

The invention provides methods of treating or effecting prophylaxis of a synucleinopathy, such as a Lewy body disease or MSA, in a patient by administration of blood-brain barrier shuttle compositions under conditions that generate a beneficial therapeutic response (e.g., reduction of neuritic and/or axonal alpha-synuclein aggregates, reduction of neuritic dystrophy, improving cognitive function, and/or reversing, treating or inhibiting cognitive decline) in the patient. In some methods, the areas of neuritic dystrophy in the neuropil of neocortex and/or basal ganglia can be reduced by 10%, 20%, 30%, 40% or more as compared to a control.

Cognitive impairment, progressive decline in cognitive function, changes in brain morphology, and changes in cerebrovascular function are commonly observed in patients suffering from or at risk of Lewy body disease. The invention provides methods of inhibiting decline of cognitive function in such patients.

The invention also provides methods of preserving or increasing synaptic density and/or dendritic density. An index of changes in synaptic or dendritic density can be measured by markers of synapse formation (synaptophysin) and/or dendrites (MAP2). In some methods, the synaptic or dendritic density can be restored to the level of synaptic or dendritic density in a healthy subject. In some methods, the level of synaptic or dendritic density in a patient can be elevated by 5%, 10%, 15%, 20%, 25%, 30% or more as compared to a control.

VII. Pharmaceutical Compositions and Methods of Treatment

In prophylactic applications, a blood-brain barrier shuttle disclosed herein or a pharmaceutical composition of the same is administered to a patient susceptible to or otherwise at risk of a disease in a regime (dose, frequency and route of administration) effective to reduce the risk, lessen the severity, or delay the onset of at least one sign or symptom of the disease. In some prophylactic applications, the regime is effective to inhibit or delay accumulation of alpha-synuclein and truncated fragments in the brain, and/or inhibit or delay its toxic effects and/or inhibit/or delay development of behavioral deficits. In therapeutic applications, a blood-brain-barrier shuttle is administered to a patient suspected of having, or already suffering from, a synucleinopathy, such as a Lewy body disease or MSA, in a regime (dose, frequency and route of administration) effective to ameliorate or at least inhibit further deterioration of at least one sign or symptom of the disease. In some therapeutic applications, the regime is effective to reduce or at least inhibit further increase of levels of alpha-synuclein and truncated fragments, associated toxicities and/or behavioral deficits.

A regime is considered therapeutically or prophylactically effective if an individual treated patient achieves an outcome more favorable than the mean outcome in a control population of comparable patients not treated by methods described herein, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses vary depending on many different factors, including type of blood-brain barrier shuttle being used, means of administration, target site, physiological state of the patient including type of synucleinopathy, whether the patient is a carrier of a certain genetic risk factor for neurodegenerative disorders including synucleinoapthies (such as genetic risk factors present in, e.g., ApoE, GBA, LRRK2, MAPT, and SNCA), whether the patient is human or an animal, other medications administered, and whether treatment is prophylactic or therapeutic.

An exemplary dosage range for the blood-brain barrier shuttles is from about 0.001 to 15 mg/kg, and more usually 0.05 to 10 mg/kg or 0.1 to 3 mg/kg or 0.15-2 mg/kg or 0.15-1.5 mg/kg, of patient body weight. Blood-brain barrier shuttles can be administered at such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. In some cases, an initial higher loading dose, followed by one or more lower doses, may be administered. Dosing schedules can include monovalent or multiple administrations over various time points, bolus administration, and pulse infusion.

Blood-brain barrier shuttles can be administered via a peripheral route (i.e., one in which an administered blood-brain barrier shuttle crosses the blood-brain barrier to reach an intended site in the brain). Routes of administration include topical, intravenous, oral, subcutaneous, intraarterial, intracranial, intrathecal, intraperitoneal, intranasal, intralesional, intrapulmonary, or intramuscular. Some routes for administration of blood-brain barrier shuttles are intravenous and subcutaneous. This type of injection is most typically performed in the arm or leg muscles. In some methods, blood-brain barrier shuttles are injected directly into a particular tissue where deposits have accumulated, for example by intracranial injection.

Pharmaceutical compositions for parenteral administration can be sterile and substantially isotonic, implying an osmolality of about 250-350 mOsm/kg water, and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients, or auxiliaries (see, e.g., Remington's Pharmaceutical Sciences 16th edition, Osol, A. Ed. (1980)). Such carriers, diluents, excipients, and auxiliaries can be nontoxic to recipients at the dosages and concentrations employed. The formulation depends on the route of administration chosen. For injection, blood-brain barrier shuttles can be formulated in aqueous solutions, such as in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, blood-brain barrier shuttles can be in lyophilized form for constitution with a suitable vehicle, e.g., sterile pyrogen-free water, before use. Sustained-release preparations can also be prepared (see, e.g., WO 2014/033074). The active ingredients can also be entrapped in microcapsules (see, e.g., WO 2014/033074).

The present regimes can be administered in combination with another agent effective in treatment or prophylaxis of the disease being treated. Such other agents can have complementary activities so that they do not adversely affect the present regimes. For example, in the case of Parkinson's disease, immunotherapy against alpha-synuclein WO/2008/103472, Levodopa, dopamine agonists, COMT inhibitors, MAO-B inhibitors, amantadine, or anticholinergic agents can be used in combination with the present regimes. Such combination therapies encompass combined administration (where two or more therapeutic agents are included in the same or separate formulations) and separate administration (i.e., administration of the blood-brain barrier shuttle can occur prior to, simultaneously, and/or following administration of the additional therapeutic agent and/or adjuvant). The blood-brain barrier shuttles can also be used in combination with other interventional therapies such as radiation therapy, behavioral therapy, or other therapies appropriate for the disease to be treated or prevented.

VIII. Other Applications

The blood-brain barrier shuttles described above can be used for bringing an entity to the brain that can detect alpha-synuclein in the context of clinical diagnosis or treatment or in research. The blood-brain barrier shuttles can also be used as research reagents for laboratory research in detecting cells bearing alpha-synuclein and their response to various stimuli. In such uses, the brain effector entity antibodies can be labeled with fluorescent molecules, spin-labeled molecules, enzymes or radioisotopes, and the blood-brain barrier shuttles can be provided in the form of kit with all the necessary reagents to perform the assay for alpha-synuclein.

The blood-brain barrier shuttles can be used for bringing an entity to the brain that can detect alpha-synuclein aggregates such as LBs in a patient. Such methods are useful to diagnose or confirm diagnosis of Parkinson's disease, other diseases associated with the presence of alpha-synuclein aggregates in the brain, or susceptibility thereto. For example, the methods can be used on a patient presenting with symptoms of dementia. If the patient has LBs, then the patient is likely suffering from a Lewy body disease, such as Parkinson's disease. The methods can also be used on asymptomatic patients. Presence of Lewy bodies or other abnormal deposits of alpha-synuclein indicates susceptibility to future symptomatic disease. The methods are also useful for monitoring disease progression and/or response to treatment in patients who have been previously diagnosed with a synucleinopathy, such as a Lewy body disease.

The methods can be performed by administering a blood-brain barrier shuttle comprising an anti-alpha-synuclein antibody disclosed herein and then detecting the antibody after it has bound. If desired, the clearing response can be avoided by using an antibody fragment lacking a full-length constant region, such as a Fab. In some methods, the same antibody can serve as both a treatment and diagnostic reagent.

For diagnosis (e.g., in vivo imaging), the blood-brain barrier shuttles can be administered by intravenous injection into the body of the patient, or directly into the brain by intracranial injection or by drilling a hole through the skull. The dosage of reagent should be within the same ranges as for treatment methods. Typically, the brain effector entity antibody is labeled, although in some methods, the antibody is unlabeled and a secondary labeling agent is used to bind to the antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci to corresponding baseline values. The baseline values can represent the mean levels in a population of undiseased individuals. Baseline values can also represent previous levels determined in the same patient. For example, baseline values can be determined in a patient before beginning treatment, and measured values thereafter are compared with the baseline values. A decrease in values relative to baseline signals a positive response to treatment.

The blood-brain barrier shuttles comprising anti-alpha-synuclein antibodies can be used to generate anti-idiotype antibodies (see, e.g., Greenspan & Bona, FASEB J. 7(5): 437-444 (1989) and Nissinoff, J. Immunol. 147:2429-2438 (1991)). Such anti-idiotype antibodies can be utilized in pharmacokinetics, pharmacodynamics, biodistribution studies as well as in studies of clinical human-anti-human antibody (HAHA) responses in individuals treated with the antibodies. For example, anti-idiotypic antibodies bind specifically the variable region of the brain effector entity 5C1 antibodies and therefore can be used to detect the antibodies in pharmacokinetic studies and help to quantify human-anti-human antibody (HAHA) responses in treated individuals.

IX. Kits

Also provided are kits including a blood-brain barrier shuttle as disclosed herein and instructions for use. Such kits can be used for, e.g., performing the diagnostic methods described above. A kit can also include a label. Kits also typically contain labeling providing directions for use of the kit. The labeling may also include a chart or other correspondence regime correlating levels of measured label with levels of antibodies to alpha-synuclein. Labeling generally refers to any written or recorded material that is attached to, or otherwise accompanies, a kit at any time during its manufacture, transport, sale or use. For example, the term labeling encompasses advertising leaflets and brochures, packaging materials, instructions, audio or video cassettes, computer discs, as well as writing imprinted directly on kits.

Also provided are diagnostic kits for performing in vivo imaging. Such kits typically contain a blood-brain barrier shuttle comprising an antibody binding to an epitope of alpha-synuclein as described herein. The antibody can be labeled or a secondary labeling reagent is included in the kit. The kit can include instructions for performing an in vivo imaging assay.

X. Articles of Manufacture

Also provided are articles of manufacture containing materials useful for the treatment and/or prevention of a synucleinopathy such as a Lewy body disease (e.g., Parkinson's disease) or MSA. The article manufacture can include a container and a label or package insert on, or associated with, the container. Examples of such containers include bottles, vials, syringes, and IV solution bags. Such containers may be formed from a variety of materials such as glass or plastic. The container holds a composition which is by itself or combined with another composition for treating, preventing, and/or diagnosing the disease. At least one active agent in the composition is a blood-brain barrier shuttle as disclosed herein. The label or package insert indicates that the composition is used for treating the disease. Some articles of manufacture may include a first container containing a composition comprising the blood-brain barrier shuttle and a second container containing a composition comprising a further cytotoxic or therapeutic agent. The articles of manufacture can also include a package insert indicating that the compositions can be used to treat the disease. They can also include a package insert with instructions for treating the disease in a subject. Such package inserts may indicate that the blood-brain barrier shuttle has improved uptake across the blood-brain barrier. The articles of manufacture can also include one or more other containers containing a pharmaceutically acceptable buffer. Other materials that can be included are those materials that are desirable from a commercial and user standpoint, such as other buffers, diluents, filters, needles, and syringes.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1: Isolation of Murine 5C1

The murine 5C1 antibody was generated in a mouse injected with a peptide conjugate containing the peptide immunogen VDPDNEAYEGGC (SEQ ID NO: 4) coupled to a sheep anti-mouse antibody. The peptide, which includes residuees 118-126 of alpha-synuclein fused to a C-terminal GGC peptide, was coupled to the sheep anti-mouse antibody via a maleimide linker bound to the C-terminal cysteine residue.

Example 2: Passive Immunization with Alpha-Synuclein Antibodies

To test the effect of alpha-synuclein antibodies on an animal model for Lewy body disease, various alpha-synuclein antibodies were used to passively immunize mice. 3-4 month old wild-type, alpha-synuclein knockout, and alpha-synuclein transgenic (line 61) female mice were used (n=14/group). Antibodies that were tested included:

9E4 (IgG1, epitope: amino acids 118-126 of alpha-synuclein);

5C1 (IgG1, immunogen: amino acids 118-126 of alpha-synuclein, cys-linker);

5D12 (IgG2, immunogen: amino acids 118-126 of alpha-synuclein, n-linker);

1H7 (IgG1, epitope: amino acids 91-99 of alpha-synuclein); and 27-1 (IgG1 control antibody).

Mice received an antibody dosage of 10 mg/kg over a 5 month period, for a total of 21 injections. In addition, the animals were injected with lentivirus (LV) expressing human alpha-synuclein (wt) by unilateral introduction of human alpha-synuclein (wt) into the hippocampus.

Readout antibodies included alpha-synuclein antibodies from Chemicon (epitope: full-length alpha-synuclein), Millipore (epitope: full-length alpha-synuclein), and ELADW 105 (epitope: amino acids 121-124 of alpha-synuclein, in some instances with alpha-synuclein truncated at residues 122-124).

Endpoints:

Antibody titers were monitored prior to termination of the experiment. Behavior was assessed using the Morris Water Maze (MWM) and horizontal round beam tests. The round beam test assesses motor balance, coordination, and gait using two beams of varying diameter. Beam A (the training beam) is larger in diameter, and therefore easier to traverse. Beam D (the testing beam) is smaller in diameter, and therefore more difficult to traverse. Water maze performance was carried out at weeks 10 and just prior to termination. On termination of the experiment, mice were sacrificed and neuropathology measurements were obtained for alpha-synuclein aggregation, synaptophysin, and MAP2. In addition, biochemistry measurements were obtained for alpha-synuclein, PSD95, and synaptophysin. Selected multilabeling and confocal labeling were carried out using synaptic, neuronal and glial markers.

Results:

The results showed that all antibodies, except 5D12, produced significant reduction in alpha-synuclein accumulation and preservation of synaptic and dendritic densities, as well as positive outcomes in MWM performance. The 9E4 antibody was effective in in vitro and in vivo studies as well as behavioral assays. In particular, the results indicate that alpha-synuclein antibodies may reduce neuritic/axonal alpha-synuclein aggregates.

Behavioral Results:

The 5C1 and 9E4 antibodies improved water maze performance in alpha-synuclein transgenic mice, as did 1H7, albeit to a lesser extent. See FIG. 3. In contrast, the 5D12 antibody did not improve water maze performance in alpha-synuclein transgenic mice. With regard to the horizontal round beam test, the 9E4 and 1H7 antibodies improved performance as measured both by speed and number of errors, whereas the 5D12 and 5C1 antibodies did not. See FIG. 4. The data in FIG. 4 are presented as the number of slips/10 cm (i.e., "errors") and the ratio of distance traveled divided by time taken to travel the distance (i.e., "speed," measured in units of 10 cm/sec).

Neuropathology Results:

The 5C1, 9E4, and 1H7 antibodies reduced ELADW-105 positive neuritic dystrophy, whereas the 5D12 antibody did not. In alpha-synuclein transgenic mice, the 9E4 antibody reduced the area of neuropil by 43% in the neocortex and by 40% in the basal ganglia, as compared to control mice (i.e., mice receiving the 27-1 IgG1 control antibody). The 9E4 antibody also preserved staining for synaptophysin and MAP2 in the neocortex and basal ganglia.

Example 3: Sequencing of Variable Domains of 5C1 mRNA was extracted and purified from a 5C1 hybridoma cell pellet using QIAGEN® OLIGOTEX® mRNA kit. Purified mRNA was next transcribed into cDNA using an oligo dT anti-sense primer and the INVITROGEN® SUPERSCRIPT® II kit. Nucleic acid sequences coding for the 5C1 heavy chain and light chain variable regions were amplified from the cDNA by PCR, using degenerate VH and VL sense primers and a gene-specific (CH/CL) anti-sense primer. The PCR products, which were designed to include the sequence of the signal peptide, variable domain, and constant domain (up to the anti-sense primer), were gel-purified, cloned into a blunt vector or TA vector, and then sequenced. Sequences were deduced from analysis of at least 3 independent clones having an open reading frame starting with a methionine and extending through the variable region into the constant region.

A nucleic acid encoding the 5C1 heavy chain variable region has the sequence of SEQ ID NO: 5. The corresponding protein sequence (FIG. 1), which includes a signal peptide at positions 1-19, has the sequence of SEQ ID NO: 6.

A nucleic acid encoding the 5C1 light chain variable region has the sequence of SEQ ID NO: 7. The corresponding protein sequence (FIG. 2), which includes a signal peptide at positions 1-19, has the sequence of SEQ ID NO: 8.

The amino acid sequence for the mature 5C1 heavy chain variable region (SEQ ID NO: 9) is shown in Table 1 (below), and the corresponding amino acid sequence for the mature 5C1 light chain variable region (SEQ ID NO: 24) is shown in Table 2 (below). Kabat numbering is used throughout.

Example 4: Humanization of Murine 5C1

Analysis of the CDRs of the 5C1 Vh region reveals a 5 residue CDR-H1 (SEQ ID NO: 10), a 17 residue CDR-H2 (SEQ ID NO: 11), and a 6 residue CDR-H3 (SEQ ID NO: 12). Similar analysis of the CDRs of the 5C1 Vk region reveals a 16 residue CDR-L1 (SEQ ID NO: 25), a 7 residue CDR-L2 (SEQ ID NO: 26), and a 9 residue CDR-L3 (SEQ ID NO: 27).

Analysis of the residues at the interface between the 5C1 Vk and Vh regions reveals that most of the residues are the ones commonly found.

A search of the non-redundant protein sequence database from NCBI allowed selection of suitable human frameworks into which to graft the 5C1 murine CDRs. For Vk, a human kappa light chain with NCBI accession code CAB51293.1 (GI:5578786; SEQ ID NO: 28) was chosen. For Vh, human Ig heavy chain AAY42876.1 (GI:66096557; SEQ ID NO: 13) was chosen.

Exemplary humanized Vh and Vk designs, with backmutations based on the selected human frameworks, are shown in Table 1 and Table 2, respectively.

Exemplary Humanized Vh Designs

Five different humanized versions of the 5C1 Vh region were designed, H1, H2, H3, H4, and H5. In selecting backmutations, residues H11, H27, H30, H48, H67, H69, H73, H91, and H94 were ultimately focused on. In each of the humanized Vh region designs, residues H11, H27, H30, H48, and H73 were backmutated to L, Y, T, I, and K, respectively, because the residues formed part of CDR-H1 according to the Chothia definition (H27 and H30) or the corresponding residues in the human framework sequence are low frequency residues (V at position H11, M at position H48, and E at position H73). For version H1 (SEQ ID NO: 14), additional residues H67 and H69 were backmutated (to A and L, respectively) to preserve CDR packing. In version H2 (SEQ ID NO: 15), no further backmutations were introduced (i.e., the backmutations at positions H67 and H69 in version H1 were eliminated). In version H3 (SEQ ID NO: 16), additional residues H67, H69, H91, and H94 were backmutated (to A, L, F, and S, respectively). The H67, H69, and H94 backmutations were to preserve CDR packing, while H91, a VhNk interface residue, was backmutated to test its impact on the interface. In version H4 (SEQ ID NO: 17), additional residues H67, H69, and H94 were backmutated (to A, L, and S, respectively). Thus, version H4 differs from H3 in that the backmutation at H91 is eliminated. In version H5 (SEQ ID NO: 18), additional residue H94 was also backmutated (to S), to preserve CDR packing.

TABLE 1

Humanized 5C1 Vh Regions

| Kabat # | Linear # | FR or CDR | Murine 5C1 (SEQ ID NO: 9) | Hu VH Acceptor FR (SEQ ID NO: 13) Acc#AAY42876.1 | 5C1 H1 (SEQ ID NO: 14) | 5C1 H2 (SEQ ID NO: 15) | 5HC H3 (SEQ ID NO: 16) | 5C1 H4 (SEQ ID NO: 17) | 5C1 H5 SEQ ID NO: 18) |
|---|---|---|---|---|---|---|---|---|---|
| 1 | 1 | Fr1 | Q | Q | Q | Q | Q | Q | Q |
| 2 | 2 | Fr1 | V | V | V | V | V | V | V |
| 3 | 3 | Fr1 | Q | Q | Q | Q | Q | Q | Q |
| 4 | 4 | Fr1 | L | L | L | L | L | L | L |
| 5 | 5 | Fr1 | Q | V | V | V | V | V | V |
| 6 | 6 | Fr1 | Q | Q | Q | Q | Q | Q | Q |
| 7 | 7 | Fr1 | S | S | S | S | S | S | S |
| 8 | 8 | Fr1 | G | G | G | G | G | G | G |
| 9 | 9 | Fr1 | A | A | A | A | A | A | A |
| 10 | 10 | Fr1 | E | E | E | E | E | E | E |
| 11 | 11 | Fr1 | L | V | L | L | L | L | L |
| 12 | 12 | Fr1 | A | K | K | K | K | K | K |
| 13 | 13 | Fr1 | K | K | K | K | K | K | K |
| 14 | 14 | Fr1 | P | P | P | P | P | P | P |
| 15 | 15 | Fr1 | G | G | G | G | G | G | G |
| 16 | 16 | Fr1 | T | S | S | S | S | S | S |

TABLE 1-continued

Humanized 5C1 Vh Regions

| Kabat # | Linear # | FR or CDR | Murine 5C1 (SEQ ID NO: 9) | Hu VH Acceptor FR (SEQ ID NO: 13) Acc#AAY42876.1 | 5C1 H1 (SEQ ID NO: 14) | 5C1 H2 (SEQ ID NO: 15) | 5HC H3 (SEQ ID NO: 16) | 5C1 H4 (SEQ ID NO: 17) | 5C1 H5 (SEQ ID NO: 18) |
|---|---|---|---|---|---|---|---|---|---|
| 17 | 17 | Fr1 | S | S | S | S | S | S | S |
| 18 | 18 | Fr1 | V | V | V | V | V | V | V |
| 19 | 19 | Fr1 | Q | K | K | K | K | K | K |
| 20 | 20 | Fr1 | M | V | V | V | V | V | V |
| 21 | 21 | Fr1 | S | S | S | S | S | S | S |
| 22 | 22 | Fr1 | C | C | C | C | C | C | C |
| 23 | 23 | Fr1 | K | K | K | K | K | K | K |
| 24 | 24 | Fr1 | A | A | A | A | A | A | A |
| 25 | 25 | Fr1 | S | S | S | S | S | S | S |
| 26 | 26 | Fr1 | G | G | G | G | G | G | G |
| 27 | 27 | Fr1 | Y | G | Y | Y | Y | Y | Y |
| 28 | 28 | Fr1 | T | T | T | T | T | T | T |
| 29 | 29 | Fr1 | F | F | F | F | F | F | F |
| 30 | 30 | Fr1 | T | N | T | T | T | T | T |
| 31 | 31 | CDR-H1 | N | N | N | N | N | N | N |
| 32 | 32 | CDR-H1 | Y | Y | Y | Y | Y | Y | Y |
| 33 | 33 | CDR-H1 | W | A | W | W | W | W | W |
| 34 | 34 | CDR-H1 | M | I | M | M | M | M | M |
| 35 | 35 | CDR-H1 | N | N | N | N | N | N | N |
| 35A | | CDR-H1 | — | — | — | — | — | — | — |
| 35B | | CDR-H1 | — | — | — | — | — | — | — |
| 36 | 36 | Fr2 | W | W | W | W | W | W | W |
| 37 | 37 | Fr2 | I | V | V | V | V | V | V |
| 38 | 38 | Fr2 | K | R | R | R | R | R | R |
| 39 | 39 | Fr2 | A | Q | Q | Q | Q | Q | Q |
| 40 | 40 | Fr2 | R | A | A | A | A | A | A |
| 41 | 41 | Fr2 | P | P | P | P | P | P | P |
| 42 | 42 | Fr2 | G | G | G | G | G | G | G |
| 43 | 43 | Fr2 | Q | Q | Q | Q | Q | Q | Q |
| 44 | 44 | Fr2 | G | G | G | G | G | G | G |
| 45 | 45 | Fr2 | L | L | L | L | L | L | L |
| 46 | 46 | Fr2 | E | E | E | E | E | E | E |
| 47 | 47 | Fr2 | W | W | W | W | W | W | W |
| 48 | 48 | Fr2 | I | M | I | I | I | I | I |
| 49 | 49 | Fr2 | G | G | G | G | G | G | G |
| 50 | 50 | CDR-H2 | A | G | A | A | A | A | A |
| 51 | 51 | CDR-H2 | T | I | T | T | T | T | T |
| 52 | 52 | CDR-H2 | N | I | N | N | N | N | N |
| 52A | 53 | CDR-H2 | P | P | P | P | P | P | P |
| 52B | | CDR-H2 | — | — | — | — | — | — | — |
| 52C | | CDR-H2 | — | — | — | — | — | — | — |
| 53 | 54 | CDR-H2 | N | I | N | N | N | N | N |
| 55 | 56 | CDR-H2 | G | G | G | G | G | G | G |
| 56 | 57 | CDR-H2 | Y | T | Y | Y | Y | Y | Y |
| 57 | 58 | CDR-H2 | T | T | T | T | T | T | T |
| 58 | 59 | CDR-H2 | D | T | D | D | D | D | D |
| 59 | 60 | CDR-H2 | Y | Y | Y | Y | Y | Y | Y |
| 60 | 61 | CDR-H2 | N | A | N | N | N | N | N |
| 61 | 62 | CDR-H2 | Q | Q | Q | Q | Q | Q | Q |
| 62 | 63 | CDR-H2 | R | K | R | R | R | R | R |
| 63 | 64 | CDR-H2 | F | F | F | F | F | F | F |
| 65 | 66 | CDR-H2 | D | G | D | D | D | D | D |
| 66 | 67 | Fr3 | K | R | R | R | R | R | R |
| 67 | 68 | Fr3 | A | V | A | V | A | A | V |
| 68 | 69 | Fr3 | I | T | T | T | T | T | T |
| 69 | 70 | Fr3 | L | I | L | I | L | L | I |
| 70 | 71 | Fr3 | T | T | T | T | T | T | T |
| 71 | 72 | Fr3 | A | A | A | A | A | A | A |
| 72 | 73 | Fr3 | D | D | D | D | D | D | D |
| 73 | 74 | Fr3 | K | E | K | K | K | K | K |
| 74 | 75 | Fr3 | S | S | S | S | S | S | S |
| 75 | 76 | Fr3 | S | T | T | T | T | T | T |
| 76 | 77 | Fr3 | N | N | N | N | N | N | N |
| 77 | 78 | Fr3 | T | T | T | T | T | T | T |
| 78 | 79 | Fr3 | A | A | A | A | A | A | A |
| 79 | 80 | Fr3 | Y | Y | Y | Y | Y | Y | Y |
| 80 | 81 | Fr3 | M | M | M | M | M | M | M |
| 81 | 82 | Fr3 | H | E | E | E | E | E | E |
| 82 | 83 | Fr3 | L | L | L | L | L | L | L |
| 82A | 84 | Fr3 | S | S | S | S | S | S | S |
| 82B | 85 | Fr3 | S | S | S | S | S | S | S |
| 82C | 86 | Fr3 | L | L | L | L | L | L | L |
| 83 | 87 | Fr3 | T | R | R | R | R | R | R |

TABLE 1-continued

Humanized 5C1 Vh Regions

| Kabat # | Linear # | FR or CDR | Murine 5C1 (SEQ ID NO: 9) | Hu VH Acceptor FR (SEQ ID NO: 13) Acc#AAY42876.1 | 5C1 H1 (SEQ ID NO: 14) | 5C1 H2 (SEQ ID NO: 15) | 5HC H3 (SEQ ID NO: 16) | 5C1 H4 (SEQ ID NO: 17) | 5C1 H5 (SEQ ID NO: 18) |
|---|---|---|---|---|---|---|---|---|---|
| 84 | 88 | Fr3 | S | S | S | S | S | S | S |
| 85 | 89 | Fr3 | E | E | E | E | E | E | E |
| 86 | 90 | Fr3 | D | D | D | D | D | D | D |
| 87 | 91 | Fr3 | S | T | T | T | T | T | T |
| 88 | 92 | Fr3 | A | A | A | A | A | A | A |
| 89 | 93 | Fr3 | V | V | V | V | V | V | V |
| 90 | 94 | Fr3 | Y | Y | Y | Y | Y | Y | Y |
| 91 | 95 | Fr3 | F | Y | Y | Y | F | Y | Y |
| 92 | 96 | Fr3 | C | C | C | C | C | C | C |
| 93 | 97 | Fr3 | A | A | A | A | A | A | A |
| 94 | 98 | Fr3 | S | R | R | R | S | S | S |
| 95 | 99 | CDR-H3 | G | E | G | G | G | G | G |
| 96 | 100 | CDR-H3 | G | G | G | G | G | G | G |
| 97 | 101 | CDR-H3 | H | N | H | H | H | H | H |
| 98 | | CDR-H3 | — | L | — | — | — | — | — |
| 99 | | CDR-H3 | — | N | — | — | — | — | — |
| 100 | | CDR-H3 | — | W | — | — | — | — | — |
| 100A | 102 | CDR-H3 | L | L | L | L | L | L | L |
| 100B | | CDR-H3 | — | — | — | — | — | — | — |
| 100C | | CDR-H3 | — | — | — | — | — | — | — |
| 100D | | CDR-H3 | — | — | — | — | — | — | — |
| 100E | | CDR-H3 | — | — | — | — | — | — | — |
| 100F | | CDR-H3 | — | — | — | — | — | — | — |
| 100G | | CDR-H3 | — | — | — | — | — | — | — |
| 100H | | CDR-H3 | — | — | — | — | — | — | — |
| 100I | | CDR-H3 | — | — | — | — | — | — | — |
| 100J | | CDR-H3 | — | — | — | — | — | — | — |
| 100K | | CDR-H3 | — | — | — | — | — | — | — |
| 101 | 103 | CDR-H3 | A | D | A | A | A | A | A |
| 102 | 104 | CDR-H3 | Y | P | Y | Y | Y | Y | Y |
| 103 | 105 | Fr4 | W | W | W | W | W | W | W |
| 104 | 106 | Fr4 | G | G | G | G | G | G | G |
| 105 | 107 | Fr4 | Q | Q | Q | Q | Q | Q | Q |
| 106 | 108 | Fr4 | G | G | G | G | G | G | G |
| 107 | 109 | Fr4 | T | T | T | T | T | T | T |
| 108 | 110 | Fr4 | V | L | L | L | L | L | L |
| 109 | 111 | Fr4 | V | V | V | V | V | V | V |
| 110 | 112 | Fr4 | T | T | T | T | T | T | T |
| 111 | 113 | Fr4 | V | V | V | V | V | V | V |
| 112 | 114 | Fr4 | S | S | S | S | S | S | S |
| 113 | 115 | Fr4 | A | S | S | S | S | S | S |

Exemplary nucleic acid sequences encoding humanized 5C1 H1, H2, H3, H4, and H5 are provided in SEQ ID NOS: 19, 20, 21, 22, and 23, respectively.

Exemplary Humanized Vk Designs

Four different humanized versions of the 5C1 Vk region were designed, L1, L2, L3, and L4. In selecting backmutations, residues L2, L12, L14, L45, L49, and L87 were ultimately focused on. In each of the humanized Vk region designs, residues L12 and L14 were backmutated to S because the corresponding residues in the human framework sequence (P and T, respectively) are low frequency residues. For version L1 (SEQ ID NO: 29), additional residues L2, L45, L49, and L87 were backmutated (to V, K, N, and F, respectively). L2 is a canonical/CDR interacting residue; L45 undergoes a polarity/charge switch from the murine to human framework sequences (K to Q), and thus could impact folding; L49 is a Vernier residue; and L87 is a VhNk interface residue. In version L2 (SEQ ID NO: 30), additional residue L45 was backmutated to K. Thus, relative to L1, the backmutations at residues L2, L49, and L87 were eliminated. In version L3 (SEQ ID NO: 31), additional residues L2, L49, and L87 were backmutated (to V, N, and F, respectively). Thus, relative to L1, the backmutation at residue L45 was eliminated. In version L4 (SEQ ID NO: 32), no additional residues were backmutated (i.e., only residues L12 and L14 were backmutated).

TABLE 2

Humanized 5C1 Vk Regions

| Kabat # | Linear # | FR or CDR | Murine 5C1 VL (SEQ ID NO: 24) | Hu Vk Acceptor Fr (SEQ ID NO: 28) Acc# CAB51293.1 | 5C1 L1 (SEQ ID NO: 29) | 5C1 L2 (SEQ ID NO: 30) | 5C1 L3 (SEQ ID NO: 31) | 5C1 L4 (SEQ ID NO: 32) |
|---|---|---|---|---|---|---|---|---|
| 1 | 1 | Fr1 | D | D | D | D | D | D |
| 2 | 2 | Fr1 | V | I | V | I | V | I |
| 3 | 3 | Fr1 | V | V | V | V | V | V |
| 4 | 4 | Fr1 | M | M | M | M | M | M |

TABLE 2-continued

Humanized 5C1 Vk Regions

| Kabat # | Linear # | FR or CDR | Murine 5C1 VL (SEQ ID NO: 24) | Hu Vk Acceptor Fr (SEQ ID NO: 28) Acc# CAB51293.1 | 5C1 L1 (SEQ ID NO: 29) | 5C1 L2 (SEQ ID NO: 30) | 5C1 L3 (SEQ ID NO: 31) | 5C1 L4 (SEQ ID NO: 32) |
|---|---|---|---|---|---|---|---|---|
| 5 | 5 | Fr1 | T | T | T | T | T | T |
| 6 | 6 | Fr1 | Q | Q | Q | Q | Q | Q |
| 7 | 7 | Fr1 | I | S | S | S | S | S |
| 8 | 8 | Fr1 | P | P | P | P | P | P |
| 9 | 9 | Fr1 | L | L | L | L | L | L |
| 10 | 10 | Fr1 | Y | S | S | S | S | S |
| 11 | 11 | Fr1 | L | L | L | L | L | L |
| 12 | 12 | Fr1 | S | P | S | S | S | S |
| 13 | 13 | Fr1 | V | V | V | V | V | V |
| 14 | 14 | Fr1 | S | T | S | S | S | S |
| 15 | 15 | Fr1 | P | P | P | P | P | P |
| 16 | 16 | Fr1 | G | G | G | G | G | G |
| 17 | 17 | Fr1 | D | E | E | E | E | E |
| 18 | 18 | Fr1 | Q | P | P | P | P | P |
| 19 | 19 | Fr1 | A | A | A | A | A | A |
| 20 | 20 | Fr1 | S | S | S | S | S | S |
| 21 | 21 | Fr1 | I | I | I | I | I | I |
| 22 | 22 | Fr1 | S | S | S | S | S | S |
| 23 | 23 | Fr1 | C | C | C | C | C | C |
| 24 | 24 | CDR-L1 | R | R | R | R | R | R |
| 25 | 25 | CDR-L1 | S | S | S | S | S | S |
| 26 | 26 | CDR-L1 | S | S | S | S | S | S |
| 27 | 27 | CDR-L1 | Q | Q | Q | Q | Q | Q |
| 27A | 28 | CDR-L1 | S | S | S | S | S | S |
| 27B | 29 | CDR-L1 | L | L | L | L | L | L |
| 27C | 30 | CDR-L1 | F | L | F | F | F | F |
| 27D | 31 | CDR-L1 | H | H | H | H | H | H |
| 27E | 32 | CDR-L1 | S | S | S | S | S | S |
| 27F |  | CDR-L1 | — | — | — | — | — | — |
| 28 | 33 | CDR-L1 | K | N | K | K | K | K |
| 29 | 34 | CDR-L1 | G | G | G | G | G | G |
| 30 | 35 | CDR-L1 | N | Y | N | N | N | N |
| 31 | 36 | CDR-L1 | T | N | T | T | T | T |
| 32 | 37 | CDR-L1 | Y | Y | Y | Y | Y | Y |
| 33 | 38 | CDR-L1 | L | L | L | L | L | L |
| 34 | 39 | CDR-L1 | H | D | H | H | H | H |
| 35 | 40 | Fr2 | W | W | W | W | W | W |
| 36 | 41 | Fr2 | Y | Y | Y | Y | Y | Y |
| 37 | 42 | Fr2 | L | L | L | L | L | L |
| 38 | 43 | Fr2 | Q | Q | Q | Q | Q | Q |
| 39 | 44 | Fr2 | K | K | K | K | K | K |
| 40 | 45 | Fr2 | P | P | P | P | P | P |
| 41 | 46 | Fr2 | G | G | G | G | G | G |
| 42 | 47 | Fr2 | Q | Q | Q | Q | Q | Q |
| 43 | 48 | Fr2 | S | S | S | S | S | S |
| 44 | 49 | Fr2 | P | P | P | P | P | P |
| 45 | 50 | Fr2 | K | Q | K | K | Q | Q |
| 46 | 51 | Fr2 | L | L | L | L | L | L |
| 47 | 52 | Fr2 | L | L | L | L | L | L |
| 48 | 53 | Fr2 | I | I | I | I | I | I |
| 49 | 54 | Fr2 | N | Y | N | Y | N | Y |
| 50 | 55 | CDR-L2 | R | L | R | R | R | R |
| 51 | 56 | CDR-L2 | V | G | V | V | V | V |
| 52 | 57 | CDR-L2 | S | S | S | S | S | S |
| 53 | 58 | CDR-L2 | N | N | N | N | N | N |
| 54 | 59 | CDR-L2 | R | R | R | R | R | R |
| 55 | 60 | CDR-L2 | F | A | F | F | F | F |
| 56 | 61 | CDR-L2 | S | S | S | S | S | S |
| 57 | 62 | Fr3 | G | G | G | G | G | G |
| 58 | 63 | Fr3 | V | V | V | V | V | V |
| 59 | 64 | Fr3 | P | P | P | P | P | P |
| 60 | 65 | Fr3 | D | D | D | D | D | D |
| 61 | 66 | Fr3 | R | R | R | R | R | R |
| 62 | 67 | Fr3 | F | F | F | F | F | F |
| 63 | 68 | Fr3 | S | S | S | S | S | S |
| 64 | 69 | Fr3 | G | G | G | G | G | G |
| 65 | 70 | Fr3 | S | S | S | S | S | S |
| 66 | 71 | Fr3 | G | G | G | G | G | G |
| 67 | 72 | Fr3 | S | S | S | S | S | S |
| 68 | 73 | Fr3 | G | G | G | G | G | G |
| 69 | 74 | Fr3 | T | T | T | T | T | T |
| 70 | 75 | Fr3 | D | D | D | D | D | D |
| 71 | 76 | Fr3 | F | F | F | F | F | F |
| 72 | 77 | Fr3 | T | T | T | T | T | T |

TABLE 2-continued

Humanized 5C1 Vk Regions

| Kabat # | Linear # | FR or CDR | Murine 5C1 VL (SEQ ID NO: 24) | Hu Vk Acceptor Fr (SEQ ID NO: 28) Acc# CAB51293.1 | 5C1 L1 (SEQ ID NO: 29) | 5C1 L2 (SEQ ID NO: 30) | 5C1 L3 (SEQ ID NO: 31) | 5C1 L4 (SEQ ID NO: 32) |
|---|---|---|---|---|---|---|---|---|
| 73 | 78 | Fr3 | L | L | L | L | L | L |
| 74 | 79 | Fr3 | K | K | K | K | K | K |
| 75 | 80 | Fr3 | I | I | I | I | I | I |
| 76 | 81 | Fr3 | S | S | S | S | S | S |
| 77 | 82 | Fr3 | G | R | R | R | R | R |
| 78 | 83 | Fr3 | V | V | V | V | V | V |
| 79 | 84 | Fr3 | E | E | E | E | E | E |
| 80 | 85 | Fr3 | A | A | A | A | A | A |
| 81 | 86 | Fr3 | E | E | E | E | E | E |
| 82 | 87 | Fr3 | D | D | D | D | D | D |
| 83 | 88 | Fr3 | L | V | V | V | V | V |
| 84 | 89 | Fr3 | G | G | G | G | G | G |
| 85 | 90 | Fr3 | V | V | V | V | V | V |
| 86 | 91 | Fr3 | Y | Y | Y | Y | Y | Y |
| 87 | 92 | Fr3 | F | Y | F | Y | F | Y |
| 88 | 93 | Fr3 | C | C | C | C | C | C |
| 89 | 94 | CDR-L3 | S | M | S | S | S | S |
| 90 | 95 | CDR-L3 | Q | Q | Q | Q | Q | Q |
| 91 | 96 | CDR-L3 | S | A | S | S | S | S |
| 92 | 97 | CDR-L3 | A | L | A | A | A | A |
| 93 | 98 | CDR-L3 | H | Q | H | H | H | H |
| 94 | 99 | CDR-L3 | V | T | V | V | V | V |
| 95 | 100 | CDR-L3 | P | P | P | P | P | P |
| 95A | | CDR-L3 | — | — | — | — | — | — |
| 95B | | CDR-L3 | — | — | — | — | — | — |
| 95C | | CDR-L3 | — | — | — | — | — | — |
| 95D | | CDR-L3 | — | — | — | — | — | — |
| 95E | | CDR-L3 | — | — | — | — | — | — |
| 95F | | CDR-L3 | — | — | — | — | — | — |
| 96 | 101 | CDR-L3 | W | P | W | W | W | W |
| 97 | 102 | CDR-L3 | T | T | T | T | T | T |
| 98 | 103 | Fr4 | F | F | F | F | F | F |
| 99 | 104 | Fr4 | G | G | G | G | G | G |
| 100 | 105 | Fr4 | G | G | G | G | G | G |
| 101 | 106 | Fr4 | G | G | G | G | G | G |
| 102 | 107 | Fr4 | T | T | T | T | T | T |
| 103 | 108 | Fr4 | K | K | K | K | K | K |
| 104 | 109 | Fr4 | L | V | V | V | V | V |
| 105 | 110 | Fr4 | E | E | E | E | E | E |
| 106 | 111 | Fr4 | I | I | I | I | I | I |
| 106A | | Fr4 | — | — | — | — | — | — |
| 107 | 112 | Fr4 | R | K | K | K | K | K |

Exemplary nucleic acid sequences encoding humanized 5C1 L1, L2, L3, and L4 are provided in SEQ ID NOS: 33, 34, 35, and 36, respectively.

Example 5: Affinity of Humanized 5C1 Antibodies for Alpha-Synuclein

Figure 5:
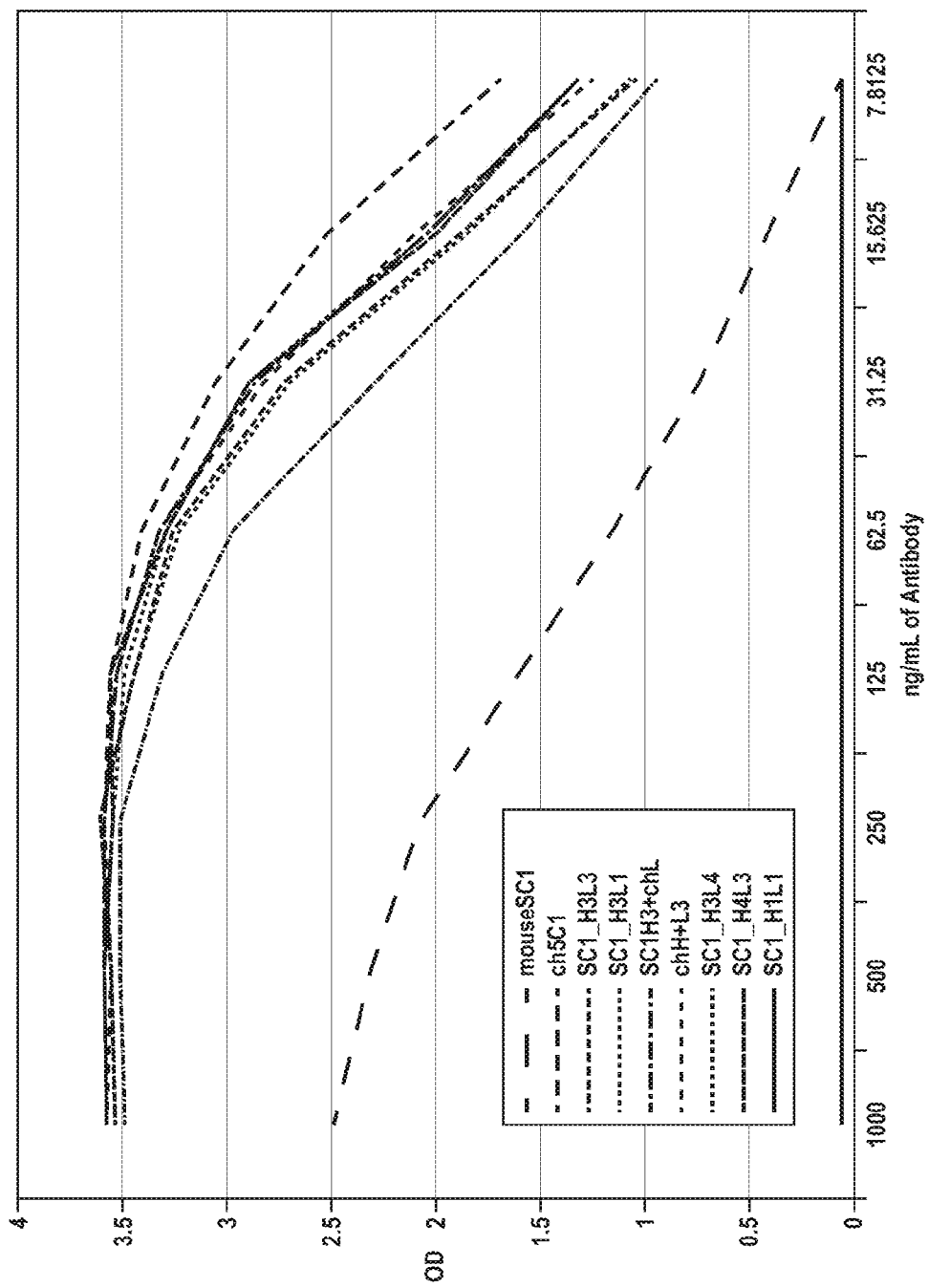
FIG. 5 shows the results of an ELISA assay testing the affinity of different humanized 5C1 antibodies.

The affinity of various combinations of 5C1 humanized heavy chains and humanized light chain proteins for alpha-synuclein was analyzed by ELISA. As shown in FIG. 5, the H1L1 version of humanized 5C1 antibody displayed no affinity for alpha-synuclein under the assay conditions. In contrast, the chimeric 5C1 antibody had a higher affinity for alpha-synuclein than the murine 5C1 antibody. Humanized versions H3L4, H4L3, and chimeric H+L3 performed comparably and almost as well as the chimeric 5C1 antibody. In addition, humanized versions H3L3 and H3L1 performed comparably, though with slightly lower affinity than H3L4, H4L3, and chimeric H+L3. The x-axis in FIG. 5 represents ng/mL of the respective antibodies, and the y-axis represents optical density.

Various humanized 5C1 antibody versions were also analyzed by Biacore, to more precisely determine binding affinities. An anti-human IgG CMS Biacore chip was prepared following the protocol supplied by GE Healthcare. Each humanized 5C1 antibody version was independently captured to a level were $R_{max}$ would not exceed 50, using the equation:

$$R_{max} = (RU \text{ of captured antibody}) * (MW \text{ of Synuclein})/(MW \text{ of captured antibody}) * 2$$

The factor of 2 in the denominator is for the number of binding sites on the antibody. Alpha-synuclein was flowed over the chop at a concentration varied from ~10× above the expected KD to ~10× below the expected KD. Data were collected and double reference subtracted to account for drift and a small amount of nonspecific binding. The data were analyzed using Biacore evaluation software using a 1:1 model and a global fit.

The results of the Biacore analysis are summarized in Table 3 (below). The data indicate that most of the loss in affinity for alpha-synuclein is due to an increased off rate in some of the antibody versions. H4L3 was identified as having a high affinity.

TABLE 3

Biacore-Determined Affinities of 5C1 Variant Antibodies

| 5C1 Variant | # Framework Mouse AAs HC | # Framework Mouse AAs LC | $K_D$ | $K_{on}$ | $K_{off}$ |
|---|---|---|---|---|---|
| m5C1 | 82 | 80 | 68.7 nM | $7.5 \times 10^4$/s | $5.1 \times 10^3$/s |
| Ch5C1 | 82 | 80 | 86.0 nM | $6.1 \times 10^4$/s | $5.3 \times 10^3$/s |
| h5C1_H3L4 | 65, incl. 9 backmutations (V11L, G27Y, N30T, M48I, V67A, I69L, E73K, Y91F, R94S) | 69, incl. 2 backmutations (P12S, T14S) | 1237.0 nM | $4.4 \times 10^4$/s | $54.5 \times 10^3$/s |
| h5C1_H4L3 | 64, incl. 8 backmutations (V11L, G27Y, N30T, M48I, V67A, I69L, E73K, R94S) | 72, incl. 5 backmutations (I2V, P12S, T14S, Y49N, Y87F) | 119.8 nM | $4.4 \times 10^4$/s | $5.1 \times 10^3$/s |
| h5C1_H4L4 | | 69, incl. 2 backmutations (P12S, T14S) | 600.9 nM | $5.3 \times 10^4$/s | $32.4 \times 10^3$/s |
| h5C1_H5L3 | 62, incl. 6 backmutations (V11L, G27Y, N30T, M48I, E73K, R94S) | 72, incl. 5 backmutations (I2V, P12S, T14S, Y49N, Y87F) | 283.1 nM | $3.9 \times 10^4$/s | $11.1 \times 10^3$/s |
| h5C1_H5L4 | | 69, incl. 2 backmutations (P12S, T14S) | 1062.0 nM | $3.7 \times 10^4$/s | $40.3 \times 10^3$/s |

Example 6: Alanine Scanning Mutagenesis

The epitopes bound by antibodies 5C1, 9E4 and 5D12 have been approximately mapped to being within residues 118-126 of alpha-synuclein due to the antibodies binding to overlapping peptides. This example describes a more precise mapping, by alanine scanning mutagenesis, of each residue between positions 118 and 126 of alpha-synuclein. Alanine is used because of its non-bulky, chemically inert, methyl functional group that nevertheless mimics the secondary structure preferences that many of the other amino acids possess. The upper portions of FIGS. 6, 7 and 8 show the results of Western blots stained with antibodies 9E4, 5C1 and 5D12, respectively. The blots include full-length alpha-synuclein and point mutants of alpha-synuclein produced by alanine scanning mutagenesis of residues 118-126 and were stained with 0.5 μg/ml of antibody. Mutations at positions 122 and 125 essentially abolish binding of 9E4, whereas mutations at other positions have little if any effect. Thus, 9E4 predominantly contacts residues 122 and 125. Mutations at positions 120-122 essentially abolish binding of 5C1, and mutations at positions 123 and 124 substantially reduce but do not abolish binding. Thus, 5C1 predominantly contacts residues 120-122 and, to a lesser extent, residues 123-124. Mutations at positions 120-122 essentially abolished binding of 5D12, and mutations at positions 118, 119, 123 and 124 substantially reduced but did not abolish binding. Thus, 5D12 binds predominantly to positions 120-122 and, to a lesser extent, positions 118, 119, 123, and 124. In the lower portion of each of FIGS. 6-8, the size of the residues within SEQ ID NO: 74 correlates with the contribution of these residues to binding of the respective antibodies to alpha-synuclein. For example, the "P" at residue 120 in FIG. 8 is large because mutation of this residue essentially abolished binding of 5D12 to alpha-synuclein, the "V" residue at 118 is smaller because mutation of this residue reduced but did not abolish binding of 5D12 to alpha-synuclein, and the "E" at residue 126 is even smaller because mutation of this residue had very little effect on binding of 5D12 to alpha-synuclein. In each of FIGS. 6-8, 1H7 antibody is used as a control. 1H7 binds to residues 91-98 of alpha-synuclein, and therefore is expected to bind to the alpha-synuclein regardless of presence of mutations in residues 118-126.

The different binding specificities of 9E4 compared to 5C1 and 5D12 may in part reflect their respective methods of production. 9E4 was made by immunization with full-length alpha-synuclein resulting in an antibody binding a conformational epitope. 5C1 and 5D12 were made by immunizing with a peptide of 10 amino acids resulting in a linear epitope.

FIG. 9 is a ball and stick model of the amino acids in alpha-synuclein proximate to the binding sites of the 9E4, 5C1 and 5D12 antibodies. The two discontinuous residues of the epitope bound by 9E4, residues 122 and 125, form a pocket in the conformation of the full-length alpha-synuclein protein.

Example 7: Generation of Expression Plasmids

Expression plasmids coding for the following antibody-sFab fusion polypeptides are constructed:

Composition of the knob 5C1-H4-scFab(8D3) heavy chain fusion protein (5C1-H4_HU-IGG1-HC-KNOB) (see FIG. 10) (SEQ ID NO: 57, but SEQ ID NO: 58 can also be used):

5C1-H4 heavy chain variable region (SEQ ID NO: 17);

human IgG1 heavy chain constant region containing the CH3 knob mutation T366W and the S354C mutation for the formation of an additional disulfide bridge (SEQ ID NO: 67, but SEQ ID NO: 68 can also be used);
glycine-serine linker (SEQ ID NO: 73; but SEQ ID NOS: 41 and 42 can also be used);
variable light chain domain variant (L596V and L598I) of the mouse 8D3 anti-transferrin antibody (Boado et al., Biotechnology and Bioengineering 102:1251-1258 (2009)) (SEQ ID NO: 63);
human C-kappa light chain (SEQ ID NO: 52);
glycine-serine linker (SEQ ID NO: 41; but SEQ ID NOS: 42 and 73 can also be used);
variable heavy chain domain of the mouse 8D3 anti-transferrin antibody (SEQ ID NO: 64); and
human IgG1 CH1 heavy chain domain (SEQ ID NO: 65).
Composition of the hole 5C1-H4 heavy chain fusion protein (5C1-H4_HU-IGG1-HC-HOLE) (see FIG. 11) (SEQ ID NO: 53, but SEQ ID NO: 55 could also be used):
5C1-H4 heavy chain variable region (SEQ ID NO: 17); and
human IgG1 heavy chain constant region containing the CH3 hole mutations T366S, L368A, and Y407V, as well as the Y349C mutation for the formation of an additional disulfide bridge (SEQ ID NO: 46, but SEQ ID NO: 48 can also be used).
Composition of the hole 5C1-L3 light chain protein (5C1-L3_HU-IGKAPPA-LC) (see FIG. 12) (SEQ ID NO: 59):
5C1-L3 light chain variable region (SEQ ID NO: 31); and
human Ckappa light chain (SEQ ID NO: 52).

The "knob" and "hole" mutations described above are enclosed in rectangles in FIGS. 10 and 11, and the mutations to cysteine for the formation of an additional disulfide bridge are enclosed in circles in FIGS. 10 and 11.

Figure 13:
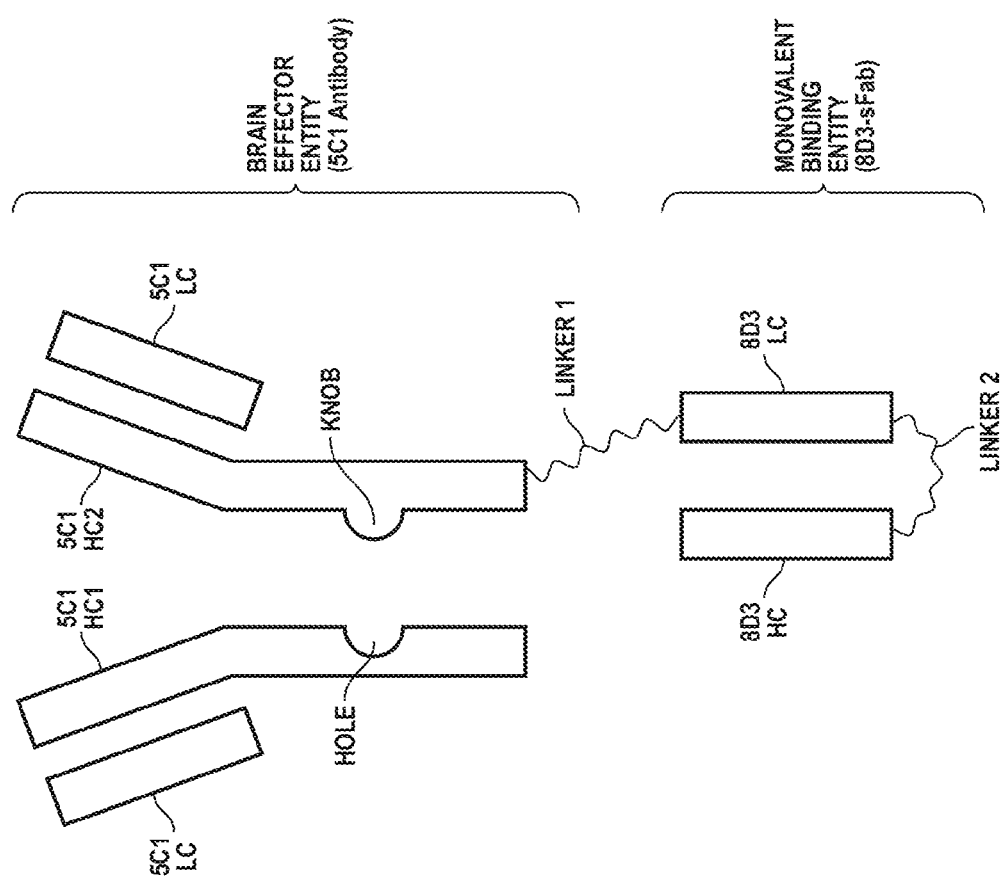
FIG. 13 depicts a version of the blood-brain barrier shuttle in which the brain effector entity comprises a 5C1 antibody and the monovalent binding entity comprises an 8D3-sFab.

A blood-brain barrier shuttle created through use of these expression plasmids is depicted in FIG. 13. In FIG. 13, HC indicates heavy chain, and LC indicates light chain.

Example 8: Purification of 5C1-sFab Constructs

The antibody chains are generated by transient transfection of HEK293 cells (human embryonic kidney cell line 293-derived) cultivated in F17 Medium (Invitrogen Corp.). For transfection, "293-Fectin" Transfection Reagent (Invitrogen) is used. The antibody chains are expressed from three different plasmids coding for the "knob" and "hole" 5C1-scFab(8D3) heavy chains and the corresponding 5C1 light chain, respectively. The three plasmids are used at an equimolar plasmid ratio upon transfection. Transfections are performed as specified in the manufacturer's instructions. Antibody-fusion-protein-containing cell culture supernatants are harvested seven days after transfection. Supernatants are stored frozen until purification.

Proteins are purified from filtered cell culture supernatants. Supernatants are applied to a protein A Sepharose column (GE Healthcare) and washed with PBS pH 7.4. Elution of antibodies is achieved with 100 mM citrate buffer at pH 3.0 followed by immediate neutralization of the sample to pH6.5. After concentration, aggregated protein and other byproducts are separated from monomeric antibodies by size exclusion chromatography (Superdex 200; GE Healthcare) in 20 mM histidine, 140 mM NaCl, pH 6.0. Every fraction is analyzed on analytical SEC (TSK G3000SWXL) and on a chip-based capillary electrophoresis system (CE-SDS, LabChipGX, Caliper) for the quantification of incompletely assembled molecules and other byproducts. Monomeric antibody fractions without byproducts are pooled. After concentration using a MILLIPORE Amicon Ultra (30 molecular weight cut off) centrifugal concentrator, the protein is stored at −80° C. Analytical characterization of the end product is done by UV protein determination, CE-SDS, size-exclusion chromatography, mass spectrometry and also by endotoxin determination.

What is claimed is:

1. A blood-brain barrier shuttle comprising:
   (a) a humanized brain effector entity antibody comprising three heavy chain CDRs having amino acid sequences of SEQ ID NOS: 10, 11, and 12, respectively, and three light chain CDRs having amino acid sequences of SEQ ID NOS: 25, 26, and 27, respectively; and
   (b) a monovalent binding entity that binds to a blood-brain barrier receptor;
   wherein the brain effector entity is coupled to the monovalent binding entity.

2. The blood-brain barrier shuttle of claim 1, wherein the brain effector entity antibody binds to human alpha-synuclein at an epitope consisting essentially of residues 120-122 of SEQ ID NO: 1 and excluding residues 118-119 of SEQ ID NO: 1.

3. The blood-brain barrier shuttle of claim 1, wherein the brain effector entity antibody binds to human alpha-synuclein at an epitope consisting of residues 120-124 of SEQ ID NO: 1.

4. The blood-brain barrier shuttle of claim 1, wherein the brain effector entity antibody is of the isotype human IgG1.

5. The blood-brain barrier shuttle of claim 1, wherein the brain effector entity antibody has at least one mutation in the constant region.

6. The blood-brain barrier shuttle of claim 5, wherein the mutation reduces complement fixation or activation by the constant region compared to a brain effector entity antibody lacking the at least one mutation.

7. The blood-brain barrier shuttle of claim 1, wherein the brain effector entity antibody is a Fab fragment, F(ab')2 fragment, or scFv.

8. The blood-brain barrier shuttle of claim 1, wherein the monovalent binding entity comprises a blood-brain barrier receptor ligand or antibody fragment.

9. The blood-brain barrier shuttle of claim 8, wherein the monovalent binding entity comprises an antibody fragment that is a scFv, Fv, scFab, sFab, or VHH.

10. The blood-brain barrier shuttle of claim 9, wherein the antibody fragment is a sFab.

11. The blood-brain barrier shuttle of claim 8, wherein the blood-brain barrier receptor is a transferrin receptor, insulin receptor, insulin-like growth factor receptor, low density lipoprotein receptor-related protein 8, low density lipoprotein receptor-related protein 1, or heparin-binding epidermal growth factor-like growth factor receptor.

12. The blood-brain barrier shuttle of claim 11, wherein the blood-brain barrier receptor is a transferrin receptor.

13. The blood-brain barrier shuttle of claim 12, wherein the monovalent binding entity comprises a sFab that specifically binds to a transferrin receptor.

14. The blood-brain barrier shuttle of claim 13, wherein the sFab binds to an epitope within SEQ ID NO: 43, SEQ ID NO: 44, and/or SEQ ID NO: 45.

15. The blood-brain barrier shuttle of claim 1, wherein the brain effector entity is coupled to the monovalent binding entity by a first linker.

16. The blood-brain barrier shuttle of claim 15, wherein the first linker is a peptide linker.

17. The blood-brain barrier shuttle of claim 16, wherein the peptide linker has a length of at least 20 amino acids.

18. The blood-brain barrier shuttle of claim 17, wherein the peptide linker has a length of 25 to 50 amino acids.

19. The blood-brain barrier shuttle of claim 17, wherein the peptide linker has an amino acid sequence of SEQ ID NO: 41, 42 or 73.

20. The blood-brain barrier shuttle of claim 15, wherein the monovalent binding entity is coupled to the C-terminal end of a heavy chain of the brain effector entity antibody by the first linker.

21. The blood-brain barrier shuttle of claim 1, wherein the monovalent binding entity comprises a CH2-CH3 Ig entity and a sFab that specifically binds to the blood-brain barrier receptor, wherein the sFab is coupled to the C-terminal end of the CH2-CH3 Ig entity.

22. The blood-brain barrier shuttle of claim 1, wherein:
(a) the monovalent binding entity comprises a CH2-CH3 Ig entity and a sFab that specifically binds to the blood-brain barrier receptor;
(b) a first linker couples the N-terminal end of the CH2-CH3 Ig domain to the brain effector entity; and
(c) a second linker couples the C-terminal end of the CH2-CH3 Ig domain to the sFab.

23. The blood-brain barrier shuttle of claim 21, wherein the CH2-CH3 Ig entity is a CH2-CH3 IgG entity.

24. The blood-brain barrier shuttle of claim 1, wherein the brain effector entity antibody includes the Fc region of a heavy chain, and wherein the monovalent binding entity is coupled to the C-terminal end of the Fc region of the heavy chain.

25. The blood-brain barrier shuttle of claim 24, wherein the brain effector entity antibody comprises two heavy chains, and wherein the monovalent binding entity is coupled to the C-terminal end of the Fc region of only one of the heavy chains.

26. The blood-brain barrier shuttle of claim 24, wherein the brain effector entity antibody comprises a heterodimerized heavy chain comprising first and second dimerization modules, and only one the first and second dimerization modules is coupled to the monovalent binding entity.

27. The blood-brain barrier shuttle of claim 26, wherein the first dimerization module comprises knobs and the second dimerization module comprises holes to receive the knobs.

28. The blood-brain barrier shuttle of claim 24, wherein:
(a) the brain effector entity antibody comprises an IgG heavy chain including an Fc region;
(b) the monovalent binding entity comprises a sFab;
(c) the C-terminal end of the Fc region of the brain effector entity antibody heavy chain is coupled to the N-terminal end of the variable light chain domain of the sFab; and
(d) the C-terminal end of the C-kappa light chain domain of the sFab is coupled to the N-terminal end of the variable heavy chain domain of the sFab.

29. A pharmaceutical composition comprising a blood-brain barrier shuttle of claim 1 and a pharmaceutically acceptable carrier.

30. A blood-brain barrier shuttle comprising:
(a) a brain effector entity comprising an antibody comprising a mature heavy chain variable region having an amino acid sequence at least 90% identical to H4 (SEQ ID NO: 17) and comprising three heavy chain CDRs having amino acid sequences of SEQ ID NOS: 10, 11, and 12, respectively, and a mature light chain variable region having an amino acid sequence at least 90% identical to L3 (SEQ ID NO: 31) and comprising three light chain CDRs having amino acid sequences of SEQ ID NOS: 25, 26, and 27, wherein the antibody specifically binds to human alpha-synuclein; and
(b) a monovalent binding entity that binds to a blood-brain barrier receptor;
wherein the brain effector entity is coupled to the monovalent binding entity.

31. The blood-brain barrier shuttle of claim 30, provided at least one of positions 11, 27, 30, 48, and 73 of SEQ ID NO:17 is occupied by L, Y, T, I, and K, respectively, and at least one of positions 12 and 14 of SEQ ID NO: 31 is occupied by S.

32. The blood-brain barrier shuttle of claim 31, provided positions 11, 27, 30, 48, and 73 of SEQ ID NO:17 are occupied by L, Y, T, I, and K, respectively, and positions 12 and 14 of SEQ ID NO: 31 are occupied by S.

33. The blood-brain barrier shuttle of claim 30, provided at least one of positions 67, 69 and 94 of SEQ ID NO: 17 is occupied by A, L, and S, respectively.

34. The blood-brain barrier shuttle of claim 33, provided positions 67, 69 and 94 of SEQ ID NO:31 are occupied by A, L, and S, respectively.

35. The blood-brain barrier shuttle of claim 33, provided position 94 of SEQ ID NO:17 is occupied by S.

36. The blood-brain barrier shuttle of claim 30, provided at least one of positions 2, 49 and 87 of SEQ ID NO:31 is occupied by V, N, and F, respectively.

37. The blood-brain barrier shuttle of claim 36, provided positions 2, 49 and 87 of SEQ ID NO:31 are occupied by V, N, and F, respectively.

38. The blood-brain barrier shuttle of claim 30, wherein the brain effector entity antibody comprises a mature heavy chain variable region having an amino acid sequence at least 95% identical to H4 (SEQ ID NO: 17) and a mature light chain variable region at least 95% identical to L3 (SEQ ID NO: 31).

39. The blood-brain barrier shuttle of claim 30, wherein the brain effector entity antibody's mature heavy chain variable region has an amino acid sequence designated H4 (SEQ ID NO: 17) and the brain effector entity antibody's mature light chain variable region has an amino acid sequence designated L3 (SEQ ID NO: 31).

40. The blood-brain barrier shuttle of claim 30, wherein the brain effector entity antibody's mature heavy chain variable region has an amino acid sequence designated H5 (SEQ ID NO: 18) and the brain effector entity antibody's mature light chain variable region has an amino acid sequence designated L3 (SEQ ID NO: 31).

* * * * *

SEQUENCE LISTING

```
<160> NUMBER OF SEQ ID NOS: 75

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110
```

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 35
<212> TYPE: PRT
<213> ORGANISM: Artificial Sequence
<220> FEATURE:
<223> OTHER INFORMATION: Non-amyloid component (NAC) domain of
      alpha-synuclein, as reported by Jensen et al.
      (1995)

<400> SEQUENCE: 2

Glu Gln Val Thr Asn Val Gly Gly Ala Val Val Thr Gly Val Thr Ala
1               5                   10                  15

Val Ala Gln Lys Thr Val Glu Gly Ala Gly Ser Ile Ala Ala Ala Thr
            20                  25                  30

Gly Phe Val
        35

<210> SEQ ID NO 3
<211> LENGTH: 28
<212> TYPE: PRT
<213> ORGANISM: Artificial Sequence
<220> FEATURE:
<223> OTHER INFORMATION: Non-amyloid component (NAC) domain of
      alpha-synuclein, as reported by Ueda et al. (1993)

<400> SEQUENCE: 3

Lys Glu Gln Val Thr Asn Val Gly Gly Ala Val Val Thr Gly Val Thr
1               5                   10                  15

Ala Val Ala Gln Lys Thr Val Glu Gly Ala Gly Ser
            20                  25

<210> SEQ ID NO 4
<211> LENGTH: 12
<212> TYPE: PRT
<213> ORGANISM: Artificial Sequence
<220> FEATURE:
<223> OTHER INFORMATION: Amino acid residues 118-129 of human
      alpha-synuclein

<400> SEQUENCE: 4

Val Asp Pro Asp Asn Glu Ala Tyr Glu Gly Gly Cys
1               5                   10

<210> SEQ ID NO 5
<211> LENGTH: 402
<212> TYPE: DNA
<213> ORGANISM: Artificial Sequence
<220> FEATURE:
<223> OTHER INFORMATION: Nucleic acid sequence encoding the murine 5C1
      heavy chain variable region with signal peptide
<220> FEATURE:
<221> NAME/KEY: sig_peptide
<222> LOCATION: (1)...(57)
<223> OTHER INFORMATION: Nucleic acid sequence encoding signal peptide

<400> SEQUENCE: 5
atggaaaggc actggatctt tctcttcctg ttatcagtaa ctggaggtgt ccactcccag     60
gtccagctgc agcagtctgg ggctgaactg gcaaaacctg gacctcagt gcagatgtcc    120 tgcaaggctt ctggctacac ctttactaat tactggatga actggataaa agcgaggcct    180

```
ggacagggtc tggaatggat tggggctact aatcctaaca atggttatac tgactacaat    240
cagaggttca aggacaaggc catattaact gcagacaaat cctccaatac agcctacatg    300
cacctgagca gcctgacatc tgaagactct gcagtctatt tctgtgcaag tgggggcac    360 ttggcttact ggggccaggg gactgtggtc actgtctctg ca                       402
```

```
<210> SEQ ID NO 6
<211> LENGTH: 134
<212> TYPE: PRT
<213> ORGANISM: Artificial Sequence
<220> FEATURE:
<223> OTHER INFORMATION: Murine 5C1 heavy chain variable region with
      signal peptide
<220> FEATURE:
<221> NAME/KEY: SIGNAL
<222> LOCATION: (1)...(19)
<223> OTHER INFORMATION: Signal peptide

<400> SEQUENCE: 6
```

```
Met Glu Arg His Trp Ile Phe Leu Phe Leu Leu Ser Val Thr Gly Gly
                -15                 -10                 -5

Val His Ser Gln Val Gln Leu Gln Gln Ser Gly Ala Glu Leu Ala Lys
                1               5                   10

Pro Gly Thr Ser Val Gln Met Ser Cys Lys Ala Ser Gly Tyr Thr Phe
    15                  20                  25

Thr Asn Tyr Trp Met Asn Trp Ile Lys Ala Arg Pro Gly Gln Gly Leu
30                  35                  40                  45

Glu Trp Ile Gly Ala Thr Asn Pro Asn Asn Gly Tyr Thr Asp Tyr Asn
                50                  55                  60

Gln Arg Phe Lys Asp Lys Ala Ile Leu Thr Ala Asp Lys Ser Ser Asn
                65                  70                  75

Thr Ala Tyr Met His Leu Ser Ser Leu Thr Ser Glu Asp Ser Ala Val
                80                  85                  90

Tyr Phe Cys Ala Ser Gly Gly His Leu Ala Tyr Trp Gly Gln Gly Thr
    95                  100                 105

Val Val Thr Val Ser Ala
110                 115
```

```
<210> SEQ ID NO 7
<211> LENGTH: 393
<212> TYPE: DNA
<213> ORGANISM: Artificial Sequence
<220> FEATURE:
<223> OTHER INFORMATION: Nucleic acid sequence encoding the murine 5C1
      light chain variable region with signal peptide
<220> FEATURE:
<221> NAME/KEY: sig_peptide
<222> LOCATION: (1)...(57)
<223> OTHER INFORMATION: Nucleic acid sequence encoding signal peptide

<400> SEQUENCE: 7
```

```
atgaagttgc ctgttaggct gttggtgctg atgttctgga ttcctgcttc agcagtgat    60 gttgtgatga cccaaattcc actctacctg tctgtcagtc ctggagatca agcctccatc    120
tcttgcagat ctagtcagag cctttttccat agtaaaggaa acacctattt acattggtat    180
ctgcagaagc caggccagtc tccaaagctc ctgatcaaca gggtttccaa ccgattttct    240
ggggtcccag acaggttcag tggcagtgga tcagggacag atttcacact caagatcagc    300
ggagtggagg ctgaagatct gggagtttat ttctgttctc aaagtgcaca tgttccgtgg    360
acgttcggtg gaggcaccaa gctggaaatc aga                                393
```

```
<210> SEQ ID NO 8
<211> LENGTH: 131
<212> TYPE: PRT
<213> ORGANISM: Artificial Sequence
<220> FEATURE:
<223> OTHER INFORMATION: Murine 5C1 light chain variable region sequence
      with signal peptide
<220> FEATURE:
<221> NAME/KEY: SIGNAL
<222> LOCATION: (1)...(19)
<223> OTHER INFORMATION: Signal peptide

<400> SEQUENCE: 8

Met Lys Leu Pro Val Arg Leu Leu Val Leu Met Phe Trp Ile Pro Ala
              -15                 -10                  -5

Ser Ser Ser Asp Val Val Met Thr Gln Ile Pro Leu Tyr Leu Ser Val
              1               5                  10

Ser Pro Gly Asp Gln Ala Ser Ile Ser Cys Arg Ser Ser Gln Ser Leu
          15                  20                  25

Phe His Ser Lys Gly Asn Thr Tyr Leu His Trp Tyr Leu Gln Lys Pro
 30                  35                  40                  45

Gly Gln Ser Pro Lys Leu Leu Ile Asn Arg Val Ser Asn Arg Phe Ser
              50                  55                  60

Gly Val Pro Asp Arg Phe Ser Gly Ser Gly Ser Gly Thr Asp Phe Thr
              65                  70                  75

Leu Lys Ile Ser Gly Val Glu Ala Glu Asp Leu Gly Val Tyr Phe Cys
              80                  85                  90

Ser Gln Ser Ala His Val Pro Trp Thr Phe Gly Gly Gly Thr Lys Leu
              95                 100                 105

Glu Ile Arg
110

<210> SEQ ID NO 9
<211> LENGTH: 115
<212> TYPE: PRT
<213> ORGANISM: Artificial Sequence
<220> FEATURE:
<223> OTHER INFORMATION: Murine 5C1 mature heavy chain variable region
<220> FEATURE:
<221> NAME/KEY: DOMAIN
<222> LOCATION: (26)...(35)
<223> OTHER INFORMATION: CDR1 as defined by composite of Kabat and
      Chothia definitions
<220> FEATURE:
<221> NAME/KEY: DOMAIN
<222> LOCATION: (50)...(66)
<223> OTHER INFORMATION: CDR2 as defined by Kabat
<220> FEATURE:
<221> NAME/KEY: DOMAIN
<222> LOCATION: (99)...(104)
<223> OTHER INFORMATION: CDR3 as defined by Kabat

<400> SEQUENCE: 9

Gln Val Gln Leu Gln Gln Ser Gly Ala Glu Leu Ala Lys Pro Gly Thr
  1               5                  10                  15

Ser Val Gln Met Ser Cys Lys Ala Ser Gly Tyr Thr Phe Thr Asn Tyr
              20                  25                  30

Trp Met Asn Trp Ile Lys Ala Arg Pro Gly Gln Gly Leu Glu Trp Ile
          35                  40                  45

Gly Ala Thr Asn Pro Asn Asn Gly Tyr Thr Tyr Asn Gln Arg Phe
 50                  55                  60

Lys Asp Lys Ala Ile Leu Thr Ala Asp Lys Ser Ser Asn Thr Ala Tyr
65                   70                  75                  80
```

Met His Leu Ser Ser Leu Thr Ser Glu Asp Ser Ala Val Tyr Phe Cys
                85                  90                  95

Ala Ser Gly Gly His Leu Ala Tyr Trp Gly Gln Gly Thr Val Val Thr
            100                 105                 110

Val Ser Ala
        115

<210> SEQ ID NO 10
<211> LENGTH: 5
<212> TYPE: PRT
<213> ORGANISM: Artificial Sequence
<220> FEATURE:
<223> OTHER INFORMATION: 5C1 heavy chain CDR1 as defined by Kabat

<400> SEQUENCE: 10

Asn Tyr Trp Met Asn
1               5

<210> SEQ ID NO 11
<211> LENGTH: 17
<212> TYPE: PRT
<213> ORGANISM: Artificial Sequence
<220> FEATURE:
<223> OTHER INFORMATION: 5C1 heavy chain CDR2 as defined by Kabat

<400> SEQUENCE: 11

Ala Thr Asn Pro Asn Asn Gly Tyr Thr Asp Tyr Asn Gln Arg Phe Lys
1               5                   10                  15

Asp

<210> SEQ ID NO 12
<211> LENGTH: 6
<212> TYPE: PRT
<213> ORGANISM: Artificial Sequence
<220> FEATURE:
<223> OTHER INFORMATION: 5C1 heavy chain CDR3 as defined by Kabat

<400> SEQUENCE: 12

Gly Gly His Leu Ala Tyr
1               5

<210> SEQ ID NO 13
<211> LENGTH: 118
<212> TYPE: PRT
<213> ORGANISM: Artificial Sequence
<220> FEATURE:
<223> OTHER INFORMATION: Human VH Acceptor FR (Acc#AAY42876.1)

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Thr Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asn Leu Asn Trp Leu Asp Pro Trp Gly Gln Gly Thr
            100                 105                 110

Leu Val Thr Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: Synthetic

<400> SEQUENCE: 14

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly His Leu Ala Tyr Trp Gly Gln Gly Thr Leu Val Thr
            100                 105                 110

Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: Synthetic

<400> SEQUENCE: 15

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly His Leu Ala Tyr Trp Gly Gln Gly Thr Leu Val Thr
            100                 105                 110

Val Ser Ser
        115

<210> SEQ ID NO 16
<211> LENGTH: 115
<212> TYPE: PRT
<213> ORGANISM: Artificial Sequence

```
<220> FEATURE:
<223> OTHER INFORMATION: Synthetic

<400> SEQUENCE: 16

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Ser Gly Gly His Leu Ala Tyr Trp Gly Gln Gly Thr Leu Val Thr
            100                 105                 110

Val Ser Ser
        115

<210> SEQ ID NO 17
<211> LENGTH: 115
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser
        115

<210> SEQ ID NO 18
<211> LENGTH: 115
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30
```

Trp Met Asn Trp Val Arg Gln Ala Pro Gly Gln Gly Leu Glu Trp Ile
         35                  40                  45

Gly Ala Thr Asn Pro Asn Asn Gly Tyr Thr Asp Tyr Asn Gln Arg Phe
 50                  55                  60

Lys Asp Arg Val Thr Ile Thr Ala Asp Lys Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Ser Gly Gly His Leu Ala Tyr Trp Gly Gln Gly Thr Leu Val Thr
             100                 105                 110

Val Ser Ser
     115

<210> SEQ ID NO 19
<211> LENGTH: 402
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)...(57)
<223> OTHER INFORMATION: Nucleic acid sequence encoding signal peptide

<400> SEQUENCE: 19
atggagttcg gcctgtcctg gctgttcctg gtggccatcc tgaagggcgt gcagtgccag      60
gtgcagctgg tgcagtccgg cgccgagctg aagaagcccg gctcctccgt gaaggtgtcc     120
tgcaaggcct ccggctacac cttcaccaac tactggatga actgggtgcg ccaggccccc     180
ggccagggcc tggagtggat cggcgccacc aaccccaaca acggctacac cgactacaac     240
cagcgcttca ggaccgcgc accctgaccgc cgacaagt ccaccaacac cgcctacatg        300
gagctgtcct ccctgcgctc cgaggacacc gccgtgtact actgcgcccg cggcggccac     360
ctggcctact ggggccaggg caccctggtg accgtgtcct cc                         402

<210> SEQ ID NO 20
<211> LENGTH: 402
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)...(57)
<223> OTHER INFORMATION: Nucleic acid sequence encoding signal peptide

<400> SEQUENCE: 20
atggagttcg gcctgtcctg gctgttcctg gtggccatcc tgaagggcgt gcagtgccag      60
gtgcagctgg tgcagtccgg cgccgagctg aagaagcccg gctcctccgt gaaggtgtcc     120
tgcaaggcct ccggctacac cttcaccaac tactggatga actgggtgcg ccaggccccc     180
ggccagggcc tggagtggat cggcgccacc aaccccaaca acggctacac cgactacaac     240
cagcgcttca aggaccgcgt gaccatcacc gccgacaagt ccaccaacac cgcctacatg     300
gagctgtcct ccctgcgctc cgaggacacc gccgtgtact actgcgcccg cggcggccac     360
ctggcctact ggggccaggg caccctggtg accgtgtcct cc                         402

<210> SEQ ID NO 21
<211> LENGTH: 402
<212> TYPE: DNA
<213> ORGANISM: Artificial Sequence

```
<220> FEATURE:
<223> OTHER INFORMATION: Synthetic
<220> FEATURE:
<221> NAME/KEY: sig_peptide
<222> LOCATION: (1)...(57)
<223> OTHER INFORMATION: Nucleic acid sequence encoding signal peptide

<400> SEQUENCE: 21
atggagttcg gcctgtcctg gctgttcctg gtggccatcc tgaagggcgt gcagtgccag    60
gtgcagctgg tgcagtccgg cgccgagctg aagaagcccg gctcctccgt gaaggtgtcc   120
tgcaaggcct ccggctacac cttcaccaac tactggatga ctgggtgcg ccaggccccc    180 ggccagggcc tggagtggat cggcgccacc aaccccaaca cggctacac cgactacaac    240 cagcgcttca aggaccgcgc caccctgacc gccgacaagt ccaccaacac cgcctacatg    300
gagctgtcct ccctgcgctc cgaggacacc gccgtgtact ctgcgcctc cggcggccac    360 ctggcctact ggggccaggg caccctggtg accgtgtcct cc                      402

<210> SEQ ID NO 22
<211> LENGTH: 402
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)...(57)
<223> OTHER INFORMATION: Nucleic acid sequence encoding signal peptide

<400> SEQUENCE: 22
atggagttcg gcctgtcctg gctgttcctg gtggccatcc tgaagggcgt gcagtgccag    60
gtgcagctgg tgcagtccgg cgccgagctg aagaagcccg gctcctccgt gaaggtgtcc   120
tgcaaggcct ccggctacac cttcaccaac tactggatga ctgggtgcg ccaggccccc    180 ggccagggcc tggagtggat cggcgccacc aaccccaaca cggctacac cgactacaac    240 cagcgcttca aggaccgcgc caccctgacc gccgacaagt ccaccaacac cgcctacatg    300
gagctgtcct ccctgcgctc cgaggacacc gccgtgtact actgcgcctc cggcggccac    360
ctggcctact ggggccaggg caccctggtg accgtgtcct cc                      402

<210> SEQ ID NO 23
<211> LENGTH: 402
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)...(57)
<223> OTHER INFORMATION: Nucleic acid sequence encoding signal peptide

<400> SEQUENCE: 23
atggagttcg gcctgtcctg gctgttcctg gtggccatcc tgaagggcgt gcagtgccag    60
gtgcagctgg tgcagtccgg cgccgagctg aagaagcccg gctcctccgt gaaggtgtcc   120
tgcaaggcct ccggctacac cttcaccaac tactggatga ctgggtgcg ccaggccccc    180 ggccagggcc tggagtggat cggcgccacc aaccccaaca cggctacac cgactacaac    240 cagcgcttca aggaccgcgt gaccatcacc gccgacaagt ccaccaacac cgcctacatg    300
gagctgtcct ccctgcgctc cgaggacacc gccgtgtact actgcgccag cggcggccac    360
ctggcctact ggggccaggg caccctggtg accgtgtcct cc                      402
```

```
<210> SEQ ID NO 24
<211> LENGTH: 112
<212> TYPE: PRT
<213> ORGANISM: Artificial Sequence
<220> FEATURE:
<223> OTHER INFORMATION: Murine 5C1 mature light chain variable region
<220> FEATURE:
<221> NAME/KEY: DOMAIN
<222> LOCATION: (24)...(39)
<223> OTHER INFORMATION: CDR1 as defined by Kabat
<220> FEATURE:
<221> NAME/KEY: DOMAIN
<222> LOCATION: (55)...(61)
<223> OTHER INFORMATION: CDR2 as defined by Kabat
<220> FEATURE:
<221> NAME/KEY: DOMAIN
<222> LOCATION: (94)...(102)
<223> OTHER INFORMATION: CDR3 as defined by Kabat

<400> SEQUENCE: 24

Asp Val Val Met Thr Gln Ile Pro Leu Tyr Leu Ser Val Ser Pro Gly
1               5                   10                  15

Asp Gln Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Lys Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Arg
            100                 105                 110

<210> SEQ ID NO 25
<211> LENGTH: 16
<212> TYPE: PRT
<213> ORGANISM: Artificial Sequence
<220> FEATURE:
<223> OTHER INFORMATION: 5C1 light chain CDR1 as defined by Kabat

<400> SEQUENCE: 25

Arg Ser Ser Gln Ser Leu Phe His Ser Lys Gly Asn Thr Tyr Leu His
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: 5C1 light chain CDR2 as defined by Kabat

<400> SEQUENCE: 26

Arg Val Ser Asn Arg Phe Ser
1               5

<210> SEQ ID NO 27
<211> LENGTH: 9
<212> TYPE: PRT
<213> ORGANISM: Artificial Sequence
<220> FEATURE:
<223> OTHER INFORMATION: 5C1 light chain CDR3 as defined by Kabat
```

<400> SEQUENCE: 27

Ser Gln Ser Ala His Val Pro Trp Thr
1               5

<210> SEQ ID NO 28
<211> LENGTH: 112
<212> TYPE: PRT
<213> ORGANISM: Artificial Sequence
<220> FEATURE:
<223> OTHER INFORMATION: Human VL Acceptor FR (Acc#CAB51293.1)

<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gly Gly Thr Lys Val Glu Ile Lys
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: Synthetic

<400> SEQUENCE: 29

Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Lys Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Synthetic

```
<400> SEQUENCE: 30

Asp Ile Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Ala His Val Pro Trp Thr Phe Gly Gly Gly Thr Lys Val Glu Ile Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Synthetic

<400> SEQUENCE: 31

Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Gln Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Synthetic

<400> SEQUENCE: 32

Asp Ile Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Ser Gln Ser
            85                  90                  95

Ala His Val Pro Trp Thr Phe Gly Gly Gly Thr Lys Val Glu Ile Lys
           100                 105                 110

<210> SEQ ID NO 33
<211> LENGTH: 402
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)...(66)
<223> OTHER INFORMATION: Nucleic acid sequence encoding signal peptide

<400> SEQUENCE: 33
atggacatgc gcgtgcccgc ccagctgctg ggcctgctga tgctgtgggt gtccggctcc    60
tccggcgacg tggtgatgac ccagtccccc ctgtccctgt ccgtgtcccc cggcgagccc   120
gcctccatct cctgccgctc ctcccagtcc ctgttccact ccaagggcaa cacctacctg   180
cactggtacc tgcagaagcc cggccagtcc cccaagctgc tgatcaaccg cgtgtccaac   240
cgcttctccg gcgtgcccga ccgcttctcc ggctccggct ccggcaccga cttcaccctg   300
aagatctccc gcgtggaggc cgaggacgtg ggcgtgtact tctgctccca gtccgcccac   360
gtgccctgga ccttcggcgg cggcaccaag gtggagatca ag                      402

<210> SEQ ID NO 34
<211> LENGTH: 402
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)...(66)
<223> OTHER INFORMATION: Nucleic acid sequence encoding signal peptide

<400> SEQUENCE: 34
atggacatgc gcgtgcccgc ccagctgctg ggcctgctga tgctgtgggt gtccggctcc    60
tccggcgaca tcgtgatgac ccagtccccc ctgtccctgt ccgtgtcccc cggcgagccc   120
gcctccatct cctgccgctc ctcccagtcc ctgttccact ccaagggcaa cacctacctg   180
cactggtacc tgcagaagcc cggccagtcc cccaagctgc tgatctaccg cgtgtccaac   240
cgcttctccg gcgtgcccga ccgcttctcc ggctccggct ccggcaccga cttcaccctg   300
aagatctccc gcgtggaggc cgaggacgtg ggcgtgtact actgctccca gtccgcccac   360
gtgccctgga ccttcggcgg cggcaccaag gtggagatca ag                      402

<210> SEQ ID NO 35
<211> LENGTH: 402
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)...(66)
<223> OTHER INFORMATION: Nucleic acid sequence encoding signal peptide

<400> SEQUENCE: 35
atggacatgc gcgtgcccgc ccagctgctg ggcctgctga tgctgtgggt gtccggctcc    60
tccggcgacg tggtgatgac ccagtccccc ctgtccctgt ccgtgtcccc cggcgagccc   120

```
gcctccatct cctgccgctc ctcccagtcc ctgttccact ccaagggcaa cacctacctg     180
cactggtacc tgcagaagcc cggccagtcc ccccagctgc tgatcaaccg cgtgtccaac     240
cgcttctccg gcgtgcccga ccgcttctcc ggctccggct ccggcaccga cttcaccctg     300
aagatctccc gcgtggaggc cgaggacgtg ggcgtgtact tctgctccca gtccgcccac     360
gtgccctgga ccttcggcgg cggcaccaag gtggagatca ag                        402
```

<210> SEQ ID NO 36
<211> LENGTH: 402
<212> TYPE: DNA
<213> ORGANISM: Artificial Sequence
<220> FEATURE:
<223> OTHER INFORMATION: Synthetic
<220> FEATURE:
<221> NAME/KEY: sig_peptide
<222> LOCATION: (1)...(66)
<223> OTHER INFORMATION: Nucleic acid sequence encoding signal peptide

<400> SEQUENCE: 36

```
atggacatgc gcgtgcccgc ccagctgctg ggcctgctga tgctgtgggt gtccggctcc      60
tccggcgaca tcgtgatgac ccagtccccc ctgtccctgt ccgtgtcccc cggcgagccc     120
gcctccatct cctgccgctc ctcccagtcc ctgttccact ccaagggcaa cacctacctg     180
cactggtacc tgcagaagcc cggccagtcc ccccagctgc tgatctaccg cgtgtccaac     240
cgcttctccg gcgtgcccga ccgcttctcc ggctccggct ccggcaccga cttcaccctg     300
aagatctccc gcgtggaggc cgaggacgtg ggcgtgtact actgctccca gtccgcccac     360
gtgccctgga ccttcggcgg cggcaccaag gtggagatca ag                        402
```

<210> SEQ ID NO 37
<211> LENGTH: 993
<212> TYPE: DNA
<213> ORGANISM: Artificial Sequence
<220> FEATURE:
<223> OTHER INFORMATION: Nucleic acid sequence encoding an exemplary
      human IgG1 constant region

<400> SEQUENCE: 37

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggggga     360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgtc aagacaaagc cgcggaggga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacacgc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
```

```
cagcagggga acgtcttctc atgctccgtg atgcatgagg ctctgcacaa ccactacacg    960
cagaagagcc tctccctgtc cccgggtaaa tga                                 993
```

<210> SEQ ID NO 38
<211> LENGTH: 330
<212> TYPE: PRT
<213> ORGANISM: Artificial Sequence
<220> FEATURE:
<223> OTHER INFORMATION: Amino acid sequence of an exemplary human IgG1
      constant region

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 39
<211> LENGTH: 321
<212> TYPE: DNA
<213> ORGANISM: Artificial Sequence
<220> FEATURE:
<223> OTHER INFORMATION: Nucleic acid sequence encoding an exemplary human kappa light chain constant region without an N-terminal arginine

<400> SEQUENCE: 39

```
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                              321
```

<210> SEQ ID NO 40
<211> LENGTH: 106
<212> TYPE: PRT
<213> ORGANISM: Artificial Sequence
<220> FEATURE:
<223> OTHER INFORMATION: Amino acid sequence of an exemplary human kappa light chain constant region without an N-terminal arginine

<400> SEQUENCE: 40

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 41
<211> LENGTH: 32
<212> TYPE: PRT
<213> ORGANISM: Artificial Sequence
<220> FEATURE:
<223> OTHER INFORMATION: Synthetic

<400> SEQUENCE: 41

```
Gly Gly Gly Gly Ser Gly Gly Gly Ser Gly Gly Gly Ser
1               5                   10                  15

Gly Gly Gly Ser Gly Gly Gly Gly Ser Gly Gly Gly Ser Gly Gly
            20                  25                  30
```

<210> SEQ ID NO 42
<211> LENGTH: 20
<212> TYPE: PRT
<213> ORGANISM: Artificial Sequence
<220> FEATURE:
<223> OTHER INFORMATION: Synthetic

```
<400> SEQUENCE: 42

Gly Gly Gly Gly Ser Gly Gly Gly Ser Gly Gly Gly Ser Gly
1               5                   10                  15

Gly Gly Gly Ser
            20

<210> SEQ ID NO 43
<211> LENGTH: 15
<212> TYPE: PRT
<213> ORGANISM: Artificial Sequence
<220> FEATURE:
<223> OTHER INFORMATION: 8D3 epitope mapping peptide 373

<400> SEQUENCE: 43

Ile Gly Gln Asn Met Val Thr Ile Val Gln Ser Asn Gly Asn Leu
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: 8D3 epitope mapping peptide 374

<400> SEQUENCE: 44

Asn Met Val Thr Ile Val Gln Ser Asn Gly Asn Leu Asp Pro Val
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: 8D3 epitope mapping peptide 375

<400> SEQUENCE: 45

Gln Ser Asn Gly Asn Leu Asp Pro Val Glu Ser Pro Glu Gly Tyr
1               5                   10                  15

<210> SEQ ID NO 46
<211> LENGTH: 330
<212> TYPE: PRT
<213> ORGANISM: Artificial Sequence
<220> FEATURE:
<223> OTHER INFORMATION: Synthetic

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 47
<211> LENGTH: 330
<212> TYPE: PRT
<213> ORGANISM: Artificial Sequence
<220> FEATURE:
<223> OTHER INFORMATION: Synthetic

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 48
<211> LENGTH: 330
<212> TYPE: PRT
<213> ORGANISM: Artificial Sequence
<220> FEATURE:
<223> OTHER INFORMATION: Synthetic

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
    275                 280                 285

Leu Val Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 49
<211> LENGTH: 330
<212> TYPE: PRT
<213> ORGANISM: Artificial Sequence
<220> FEATURE:
<223> OTHER INFORMATION: Synthetic

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

Lys Ala Leu Gly Ala Pro Ile Glu Lys Thr Ile Ser Lys Ala Lys Gly
210                 215                 220

Gln Pro Arg Glu Pro Gln Val Tyr Thr Leu Pro Pro Cys Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 50
<211> LENGTH: 814
<212> TYPE: PRT
<213> ORGANISM: Artificial Sequence
<220> FEATURE:
<223> OTHER INFORMATION: Synthetic

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Cys Arg Asp Glu
225                 230                 235                 240

```
Leu Thr Lys Asn Gln Val Ser Leu Trp Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Gly Ser Gly Gly Gly Gly
            325                 330                 335

Ser Gly Gly Gly Gly Ser Gly Gly Gly Ser Asp Ile Gln Met Thr
            340                 345                 350

Gln Ser Pro Ala Ser Leu Ser Ala Ser Leu Glu Glu Ile Val Thr Ile
            355                 360                 365

Thr Cys Gln Ala Ser Gln Asp Ile Gly Asn Trp Leu Ala Trp Tyr Gln
            370                 375                 380

Gln Lys Pro Gly Lys Ser Pro Gln Leu Leu Ile Tyr Gly Ala Thr Ser
385                 390                 395                 400

Leu Ala Asp Gly Val Pro Ser Arg Phe Ser Gly Ser Arg Ser Gly Thr
                405                 410                 415

Gln Phe Ser Leu Lys Ile Ser Arg Val Gln Val Glu Asp Ile Gly Ile
            420                 425                 430

Tyr Tyr Cys Leu Gln Ala Tyr Asn Thr Pro Trp Thr Phe Gly Gly Gly
            435                 440                 445

Thr Lys Val Glu Ile Lys Arg Thr Val Ala Ala Pro Ser Val Phe Ile
            450                 455                 460

Phe Pro Pro Ser Asp Glu Gln Leu Lys Ser Gly Thr Ala Ser Val Val
465                 470                 475                 480

Cys Leu Leu Asn Asn Phe Tyr Pro Arg Glu Ala Lys Val Gln Trp Lys
                485                 490                 495

Val Asp Asn Ala Leu Gln Ser Gly Asn Ser Gln Glu Ser Val Thr Glu
            500                 505                 510

Gln Asp Ser Lys Asp Ser Thr Tyr Ser Leu Ser Ser Thr Leu Thr Leu
            515                 520                 525

Ser Lys Ala Asp Tyr Glu Lys His Lys Val Tyr Ala Cys Glu Val Thr
            530                 535                 540

His Gln Gly Leu Ser Ser Pro Val Thr Lys Ser Phe Asn Arg Gly Glu
545                 550                 555                 560

Cys Gly Gly Gly Gly Ser Gly Gly Gly Gly Ser Gly Gly Gly Gly Ser
                565                 570                 575

Gly Gly Gly Gly Ser Gly Gly Gly Ser Gly Gly Gly Gly Ser Gly
            580                 585                 590

Gly Glu Val Gln Leu Val Glu Ser Gly Gly Leu Val Gln Pro Gly
            595                 600                 605

Asn Ser Leu Thr Leu Ser Cys Val Ala Ser Gly Phe Thr Phe Ser Asn
            610                 615                 620

Tyr Gly Met His Trp Ile Arg Gln Ala Pro Lys Lys Gly Leu Glu Trp
625                 630                 635                 640

Ile Ala Met Ile Tyr Tyr Asp Ser Ser Lys Met Asn Tyr Ala Asp Thr
                645                 650                 655
```

```
Val Lys Gly Arg Phe Thr Ile Ser Arg Asp Asn Ser Lys Asn Thr Leu
            660                 665                 670

Tyr Leu Glu Met Asn Ser Leu Arg Ser Glu Asp Thr Ala Met Tyr Tyr
            675                 680                 685

Cys Ala Val Pro Thr Ser His Tyr Val Val Asp Val Trp Gly Gln Gly
            690                 695                 700

Val Ser Val Thr Val Ser Ser Ala Ser Thr Lys Gly Pro Ser Val Phe
705                 710                 715                 720

Pro Leu Ala Pro Ser Ser Lys Ser Thr Ser Gly Gly Thr Ala Ala Leu
            725                 730                 735

Gly Cys Leu Val Lys Asp Tyr Phe Pro Glu Pro Val Thr Val Ser Trp
            740                 745                 750

Asn Ser Gly Ala Leu Thr Ser Gly Val His Thr Phe Pro Ala Val Leu
            755                 760                 765

Gln Ser Ser Gly Leu Tyr Ser Leu Ser Ser Val Val Thr Val Pro Ser
            770                 775                 780

Ser Ser Leu Gly Thr Gln Thr Tyr Ile Cys Asn Val Asn His Lys Pro
785                 790                 795                 800

Ser Asn Thr Lys Val Asp Lys Lys Val Glu Pro Lys Ser Cys
            805                 810
```

<210> SEQ ID NO 51
<211> LENGTH: 814
<212> TYPE: PRT
<213> ORGANISM: Artificial Sequence
<220> FEATURE:
<223> OTHER INFORMATION: Synthetic

<400> SEQUENCE: 51

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Gly Ala Pro Ile Glu Lys Thr Ile Ser Lys Ala Lys Gly
210                 215                 220

Gln Pro Arg Glu Pro Gln Val Tyr Thr Leu Pro Pro Cys Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Gly Ser Gly Gly Gly Gly
                325                 330                 335

Ser Gly Gly Gly Gly Ser Gly Gly Gly Ser Asp Ile Gln Met Thr
            340                 345                 350

Gln Ser Pro Ala Ser Leu Ser Ala Ser Leu Glu Glu Ile Val Thr Ile
            355                 360                 365

Thr Cys Gln Ala Ser Gln Asp Ile Gly Asn Trp Leu Ala Trp Tyr Gln
        370                 375                 380

Gln Lys Pro Gly Lys Ser Pro Gln Leu Leu Ile Tyr Gly Ala Thr Ser
385                 390                 395                 400

Leu Ala Asp Gly Val Pro Ser Arg Phe Ser Gly Ser Arg Ser Gly Thr
                405                 410                 415

Gln Phe Ser Leu Lys Ile Ser Arg Val Gln Val Glu Asp Ile Gly Ile
            420                 425                 430

Tyr Tyr Cys Leu Gln Ala Tyr Asn Thr Pro Trp Thr Phe Gly Gly Gly
        435                 440                 445

Thr Lys Val Glu Ile Lys Arg Thr Val Ala Ala Pro Ser Val Phe Ile
450                 455                 460

Phe Pro Pro Ser Asp Glu Gln Leu Lys Ser Gly Thr Ala Ser Val Val
465                 470                 475                 480

Cys Leu Leu Asn Asn Phe Tyr Pro Arg Glu Ala Lys Val Gln Trp Lys
                485                 490                 495

Val Asp Asn Ala Leu Gln Ser Gly Asn Ser Gln Glu Ser Val Thr Glu
            500                 505                 510

Gln Asp Ser Lys Asp Ser Thr Tyr Ser Leu Ser Ser Thr Leu Thr Leu
            515                 520                 525

Ser Lys Ala Asp Tyr Glu Lys His Lys Val Tyr Ala Cys Glu Val Thr
530                 535                 540

His Gln Gly Leu Ser Ser Pro Val Thr Lys Ser Phe Asn Arg Gly Glu
545                 550                 555                 560

Cys Gly Gly Gly Gly Ser Gly Gly Gly Gly Ser Gly Gly Gly Gly Ser
                565                 570                 575

Gly Gly Gly Gly Ser Gly Gly Gly Ser Gly Gly Gly Gly Ser Gly
            580                 585                 590

Gly Glu Val Gln Leu Val Glu Ser Gly Gly Leu Val Gln Pro Gly
        595                 600                 605

Asn Ser Leu Thr Leu Ser Cys Val Ala Ser Gly Phe Thr Phe Ser Asn
    610                 615                 620
```

Tyr Gly Met His Trp Ile Arg Gln Ala Pro Lys Lys Gly Leu Glu Trp
625                 630                 635                 640

Ile Ala Met Ile Tyr Tyr Asp Ser Ser Lys Met Asn Tyr Ala Asp Thr
            645                 650                 655

Val Lys Gly Arg Phe Thr Ile Ser Arg Asp Asn Ser Lys Asn Thr Leu
        660                 665                 670

Tyr Leu Glu Met Asn Ser Leu Arg Ser Glu Asp Thr Ala Met Tyr Tyr
    675                 680                 685

Cys Ala Val Pro Thr Ser His Tyr Val Val Asp Val Trp Gly Gln Gly
690                 695                 700

Val Ser Val Thr Val Ser Ser Ala Ser Thr Lys Gly Pro Ser Val Phe
705                 710                 715                 720

Pro Leu Ala Pro Ser Ser Lys Ser Thr Ser Gly Gly Thr Ala Ala Leu
            725                 730                 735

Gly Cys Leu Val Lys Asp Tyr Phe Pro Glu Pro Val Thr Val Ser Trp
        740                 745                 750

Asn Ser Gly Ala Leu Thr Ser Gly Val His Thr Phe Pro Ala Val Leu
    755                 760                 765

Gln Ser Ser Gly Leu Tyr Ser Leu Ser Ser Val Val Thr Val Pro Ser
770                 775                 780

Ser Ser Leu Gly Thr Gln Thr Tyr Ile Cys Asn Val Asn His Lys Pro
785                 790                 795                 800

Ser Asn Thr Lys Val Asp Lys Lys Val Glu Pro Lys Ser Cys
            805                 810

<210> SEQ ID NO 52
<211> LENGTH: 107
<212> TYPE: PRT
<213> ORGANISM: Artificial Sequence
<220> FEATURE:
<223> OTHER INFORMATION: HU-IGKAPPA-LC (with N-terminal arginine)

<400> SEQUENCE: 52

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 53
<211> LENGTH: 445
<212> TYPE: PRT
<213> ORGANISM: Artificial Sequence
<220> FEATURE:
<223> OTHER INFORMATION: Synthetic

```
<400> SEQUENCE: 53

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415
```

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 54
<211> LENGTH: 445
<212> TYPE: PRT
<213> ORGANISM: Artificial Sequence
<220> FEATURE:
<223> OTHER INFORMATION: Synthetic

<400> SEQUENCE: 54

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

```
Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 55
<211> LENGTH: 445
<212> TYPE: PRT
<213> ORGANISM: Artificial Sequence
<220> FEATURE:
<223> OTHER INFORMATION: Synthetic

<400> SEQUENCE: 55

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
            325                 330                 335

Ala Lys Gly Gln Pro Arg Glu Pro Gln Val Cys Thr Leu Pro Pro Ser
        340                 345                 350

Arg Asp Glu Leu Thr Lys Asn Gln Val Ser Leu Ser Cys Ala Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 56
<211> LENGTH: 445
<212> TYPE: PRT
<213> ORGANISM: Artificial Sequence
<220> FEATURE:
<223> OTHER INFORMATION: Synthetic

<400> SEQUENCE: 56

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Ala Ser Gly Gly His Leu Ala Tyr Trp Gly Gln Gly Thr Leu Val Thr
        100                 105                 110

Val Ser Ser Ala Ser Thr Lys Gly Pro Ser Val Phe Pro Leu Ala Pro
    115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 57
<211> LENGTH: 929
<212> TYPE: PRT
<213> ORGANISM: Artificial Sequence
<220> FEATURE:
<223> OTHER INFORMATION: Synthetic

<400> SEQUENCE: 57

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Ser Gly
            435                 440                 445

Gly Gly Gly Ser Gly Gly Gly Ser Gly Gly Gly Gly Ser Asp Ile
            450                 455                 460

Gln Met Thr Gln Ser Pro Ala Ser Leu Ser Ala Ser Leu Glu Glu Ile
465                 470                 475                 480

Val Thr Ile Thr Cys Gln Ala Ser Gln Asp Ile Gly Asn Trp Leu Ala
            485                 490                 495

Trp Tyr Gln Gln Lys Pro Gly Lys Ser Pro Gln Leu Leu Ile Tyr Gly
            500                 505                 510

```
Ala Thr Ser Leu Ala Asp Gly Val Pro Ser Arg Phe Ser Gly Ser Arg
            515                 520                 525

Ser Gly Thr Gln Phe Ser Leu Lys Ile Ser Arg Val Gln Val Glu Asp
            530                 535                 540

Ile Gly Ile Tyr Tyr Cys Leu Gln Ala Tyr Asn Thr Pro Trp Thr Phe
545                 550                 555                 560

Gly Gly Gly Thr Lys Val Glu Ile Lys Arg Thr Val Ala Ala Pro Ser
            565                 570                 575

Val Phe Ile Phe Pro Pro Ser Asp Glu Gln Leu Lys Ser Gly Thr Ala
            580                 585                 590

Ser Val Val Cys Leu Leu Asn Asn Phe Tyr Pro Arg Glu Ala Lys Val
            595                 600                 605

Gln Trp Lys Val Asp Asn Ala Leu Gln Ser Gly Asn Ser Gln Glu Ser
            610                 615                 620

Val Thr Glu Gln Asp Ser Lys Asp Ser Thr Tyr Ser Leu Ser Ser Thr
625                 630                 635                 640

Leu Thr Leu Ser Lys Ala Asp Tyr Glu Lys His Lys Val Tyr Ala Cys
            645                 650                 655

Glu Val Thr His Gln Gly Leu Ser Ser Pro Val Thr Lys Ser Phe Asn
            660                 665                 670

Arg Gly Glu Cys Gly Gly Gly Ser Gly Gly Gly Ser Gly Gly
            675                 680                 685

Gly Gly Ser Gly Gly Gly Ser Gly Gly Gly Ser Gly Gly
            690                 695                 700

Gly Ser Gly Gly Glu Val Gln Leu Val Glu Ser Gly Gly Gly Leu Val
705                 710                 715                 720

Gln Pro Gly Asn Ser Leu Thr Leu Ser Cys Val Ala Ser Gly Phe Thr
            725                 730                 735

Phe Ser Asn Tyr Gly Met His Trp Ile Arg Gln Ala Pro Lys Lys Gly
            740                 745                 750

Leu Glu Trp Ile Ala Met Ile Tyr Tyr Asp Ser Ser Lys Met Asn Tyr
            755                 760                 765

Ala Asp Thr Val Lys Gly Arg Phe Thr Ile Ser Arg Asp Asn Ser Lys
            770                 775                 780

Asn Thr Leu Tyr Leu Glu Met Asn Ser Leu Arg Ser Glu Asp Thr Ala
785                 790                 795                 800

Met Tyr Tyr Cys Ala Val Pro Thr Ser His Tyr Val Asp Val Trp
            805                 810                 815

Gly Gln Gly Val Ser Val Thr Val Ser Ser Ala Ser Thr Lys Gly Pro
            820                 825                 830

Ser Val Phe Pro Leu Ala Pro Ser Ser Lys Ser Thr Ser Gly Gly Thr
            835                 840                 845

Ala Ala Leu Gly Cys Leu Val Lys Asp Tyr Phe Pro Glu Pro Val Thr
            850                 855                 860

Val Ser Trp Asn Ser Gly Ala Leu Thr Ser Gly Val His Thr Phe Pro
865                 870                 875                 880

Ala Val Leu Gln Ser Ser Gly Leu Tyr Ser Leu Ser Ser Val Val Thr
            885                 890                 895

Val Pro Ser Ser Ser Leu Gly Thr Gln Thr Tyr Ile Cys Asn Val Asn
            900                 905                 910

His Lys Pro Ser Asn Thr Lys Val Asp Lys Lys Val Glu Pro Lys Ser
            915                 920                 925

Cys
```

```
<210> SEQ ID NO 58
<211> LENGTH: 929
<212> TYPE: PRT
<213> ORGANISM: Artificial Sequence
<220> FEATURE:
<223> OTHER INFORMATION: Synthetic

<400> SEQUENCE: 58

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365
```

```
Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Gly Gly Ser Gly
            435                 440                 445

Gly Gly Gly Ser Gly Gly Gly Gly Ser Gly Gly Gly Gly Ser Asp Ile
450                 455                 460

Gln Met Thr Gln Ser Pro Ala Ser Leu Ser Ala Ser Leu Glu Glu Ile
465                 470                 475                 480

Val Thr Ile Thr Cys Gln Ala Ser Gln Asp Ile Gly Asn Trp Leu Ala
                485                 490                 495

Trp Tyr Gln Gln Lys Pro Gly Lys Ser Pro Gln Leu Leu Ile Tyr Gly
                500                 505                 510

Ala Thr Ser Leu Ala Asp Gly Val Pro Ser Arg Phe Ser Gly Ser Arg
                515                 520                 525

Ser Gly Thr Gln Phe Ser Leu Lys Ile Ser Arg Val Gln Val Glu Asp
530                 535                 540

Ile Gly Ile Tyr Tyr Cys Leu Gln Ala Tyr Asn Thr Pro Trp Thr Phe
545                 550                 555                 560

Gly Gly Gly Thr Lys Val Glu Ile Lys Arg Thr Val Ala Ala Pro Ser
                565                 570                 575

Val Phe Ile Phe Pro Pro Ser Asp Glu Gln Leu Lys Ser Gly Thr Ala
                580                 585                 590

Ser Val Val Cys Leu Leu Asn Asn Phe Tyr Pro Arg Glu Ala Lys Val
                595                 600                 605

Gln Trp Lys Val Asp Asn Ala Leu Gln Ser Gly Asn Ser Gln Glu Ser
610                 615                 620

Val Thr Glu Gln Asp Ser Lys Asp Ser Thr Tyr Ser Leu Ser Ser Thr
625                 630                 635                 640

Leu Thr Leu Ser Lys Ala Asp Tyr Glu Lys His Lys Val Tyr Ala Cys
                645                 650                 655

Glu Val Thr His Gln Gly Leu Ser Pro Val Thr Lys Ser Phe Asn
                660                 665                 670

Arg Gly Glu Cys Gly Gly Gly Gly Ser Gly Gly Gly Gly Ser Gly Gly
                675                 680                 685

Gly Gly Ser Gly Gly Gly Gly Ser Gly Gly Gly Gly Ser Gly Gly Gly
                690                 695                 700

Gly Ser Gly Gly Glu Val Gln Leu Val Glu Ser Gly Gly Gly Leu Val
705                 710                 715                 720

Gln Pro Gly Asn Ser Leu Thr Leu Ser Cys Val Ala Ser Gly Phe Thr
                725                 730                 735

Phe Ser Asn Tyr Gly Met His Trp Ile Arg Gln Ala Pro Lys Lys Gly
                740                 745                 750

Leu Glu Trp Ile Ala Met Ile Tyr Tyr Asp Ser Ser Lys Met Asn Tyr
                755                 760                 765

Ala Asp Thr Val Lys Gly Arg Phe Thr Ile Ser Arg Asp Asn Ser Lys
770                 775                 780
```

```
Asn Thr Leu Tyr Leu Glu Met Asn Ser Leu Arg Ser Glu Asp Thr Ala
785                 790                 795                 800

Met Tyr Tyr Cys Ala Val Pro Thr Ser His Tyr Val Val Asp Val Trp
            805                 810                 815

Gly Gln Gly Val Ser Val Thr Val Ser Ser Ala Ser Thr Lys Gly Pro
        820                 825                 830

Ser Val Phe Pro Leu Ala Pro Ser Ser Lys Ser Thr Ser Gly Gly Thr
        835                 840                 845

Ala Ala Leu Gly Cys Leu Val Lys Asp Tyr Phe Pro Glu Pro Val Thr
    850                 855                 860

Val Ser Trp Asn Ser Gly Ala Leu Thr Ser Gly Val His Thr Phe Pro
865                 870                 875                 880

Ala Val Leu Gln Ser Ser Gly Leu Tyr Ser Leu Ser Ser Val Val Thr
            885                 890                 895

Val Pro Ser Ser Ser Leu Gly Thr Gln Thr Tyr Ile Cys Asn Val Asn
                900                 905                 910

His Lys Pro Ser Asn Thr Lys Val Asp Lys Lys Val Glu Pro Lys Ser
        915                 920                 925

Cys
```

<210> SEQ ID NO 59
<211> LENGTH: 219
<212> TYPE: PRT
<213> ORGANISM: Artificial Sequence
<220> FEATURE:
<223> OTHER INFORMATION: Synthetic

<400> SEQUENCE: 59

```
Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Gln Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

-continued

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 60
<211> LENGTH: 467
<212> TYPE: PRT
<213> ORGANISM: Artificial Sequence
<220> FEATURE:
<223> OTHER INFORMATION: Synthetic

<400> SEQUENCE: 60

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
            85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys Gly Gly Gly Ser Gly Gly Gly Gly Gly Ser
    210                 215                 220

Gly Gly Gly Gly Ser Gly Gly Gly Ser Gly Gly Gly Gly Ser Gly
225                 230                 235                 240

Gly Gly Ser Gly Gly Glu Val Gln Leu Val Glu Ser Gly Gly
            245                 250                 255

Leu Val Gln Pro Gly Asn Ser Leu Thr Leu Ser Cys Val Ala Ser Gly
        260                 265                 270

Phe Thr Phe Ser Asn Tyr Gly Met His Trp Ile Arg Gln Ala Pro Lys
    275                 280                 285

Lys Gly Leu Glu Trp Ile Ala Met Ile Tyr Tyr Asp Ser Ser Lys Met
    290                 295                 300

Asn Tyr Ala Asp Thr Val Lys Gly Arg Phe Thr Ile Ser Arg Asp Asn
305                 310                 315                 320

Ser Lys Asn Thr Leu Tyr Leu Glu Met Asn Ser Leu Arg Ser Glu Asp
            325                 330                 335

```
Thr Ala Met Tyr Tyr Cys Ala Val Pro Thr Ser His Tyr Val Val Asp
            340                 345                 350
Val Trp Gly Gln Gly Val Ser Val Thr Val Ser Ser Ala Ser Thr Lys
        355                 360                 365
Gly Pro Ser Val Phe Pro Leu Ala Pro Ser Ser Lys Ser Thr Ser Gly
    370                 375                 380
Gly Thr Ala Ala Leu Gly Cys Leu Val Lys Asp Tyr Phe Pro Glu Pro
385                 390                 395                 400
Val Thr Val Ser Trp Asn Ser Gly Ala Leu Thr Ser Gly Val His Thr
                405                 410                 415
Phe Pro Ala Val Leu Gln Ser Ser Gly Leu Tyr Ser Leu Ser Ser Val
            420                 425                 430
Val Thr Val Pro Ser Ser Ser Leu Gly Thr Gln Thr Tyr Ile Cys Asn
        435                 440                 445
Val Asn His Lys Pro Ser Asn Thr Lys Val Asp Lys Lys Val Glu Pro
    450                 455                 460
Lys Ser Cys
465

<210> SEQ ID NO 61
<211> LENGTH: 214
<212> TYPE: PRT
<213> ORGANISM: Artificial Sequence
<220> FEATURE:
<223> OTHER INFORMATION: Synthetic

<400> SEQUENCE: 61

Asp Ile Gln Met Thr Gln Ser Pro Ala Ser Leu Ser Ala Ser Leu Glu
1               5                   10                  15
Glu Ile Val Thr Ile Thr Cys Gln Ala Ser Gln Asp Ile Gly Asn Trp
            20                  25                  30
Leu Ala Trp Tyr Gln Gln Lys Pro Gly Lys Ser Pro Gln Leu Leu Ile
        35                  40                  45
Tyr Gly Ala Thr Ser Leu Ala Asp Gly Val Pro Ser Arg Phe Ser Gly
    50                  55                  60
Ser Arg Ser Gly Thr Gln Phe Ser Leu Lys Ile Ser Arg Val Gln Val
65                  70                  75                  80
Glu Asp Ile Gly Ile Tyr Tyr Cys Leu Gln Ala Tyr Asn Thr Pro Trp
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

```
<210> SEQ ID NO 62
<211> LENGTH: 221
<212> TYPE: PRT
<213> ORGANISM: Artificial Sequence
<220> FEATURE:
<223> OTHER INFORMATION: Synthetic

<400> SEQUENCE: 62

Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 63
<211> LENGTH: 107
<212> TYPE: PRT
<213> ORGANISM: Artificial Sequence
<220> FEATURE:
<223> OTHER INFORMATION: 8D3VL

<400> SEQUENCE: 63

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Phe Ser Leu Lys Ile Ser Arg Val Gln Val
65                  70                  75                  80
```

```
Glu Asp Ile Gly Ile Tyr Tyr Cys Leu Gln Ala Tyr Asn Thr Pro Trp
                85                  90                  95

Thr Phe Gly Gly Gly Thr Lys Val Glu Ile Lys
            100                 105

<210> SEQ ID NO 64
<211> LENGTH: 118
<212> TYPE: PRT
<213> ORGANISM: Artificial Sequence
<220> FEATURE:
<223> OTHER INFORMATION: 8D3VH

<400> SEQUENCE: 64

Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110

Ser Val Thr Val Ser Ser
        115

<210> SEQ ID NO 65
<211> LENGTH: 103
<212> TYPE: PRT
<213> ORGANISM: Artificial Sequence
<220> FEATURE:
<223> OTHER INFORMATION: HU-CH1

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 66
<211> LENGTH: 330
<212> TYPE: PRT
<213> ORGANISM: Artificial Sequence
<220> FEATURE:
<223> OTHER INFORMATION: Exemplary human IgG1 constant region of the
      IgG1 G1m3 allotype
```

<400> SEQUENCE: 66

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 67
<211> LENGTH: 328
<212> TYPE: PRT
<213> ORGANISM: Artificial Sequence
<220> FEATURE:
<223> OTHER INFORMATION: Synthetic -continued

<400> SEQUENCE: 67

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 68
<211> LENGTH: 328
<212> TYPE: PRT
<213> ORGANISM: Artificial Sequence
<220> FEATURE:
<223> OTHER INFORMATION: Synthetic

<400> SEQUENCE: 68

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
210                 215                 220

Gln Pro Arg Glu Pro Gln Val Tyr Thr Leu Pro Pro Cys Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 69
<211> LENGTH: 443
<212> TYPE: PRT
<213> ORGANISM: Artificial Sequence
<220> FEATURE:
<223> OTHER INFORMATION: Synthetic

```
<400> SEQUENCE: 69

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

Gln Gly Asn Val Phe Ser Cys Ser Val Met His Glu Ala Leu His Asn
                420                 425                 430

His Tyr Thr Gln Lys Ser Leu Ser Leu Ser Pro
        435                 440

<210> SEQ ID NO 70
<211> LENGTH: 443
<212> TYPE: PRT
<213> ORGANISM: Artificial Sequence
<220> FEATURE:
<223> OTHER INFORMATION: Synthetic

<400> SEQUENCE: 70

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

```
Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440

<210> SEQ ID NO 71
<211> LENGTH: 321
<212> TYPE: DNA
<213> ORGANISM: Artificial Sequence
<220> FEATURE:
<223> OTHER INFORMATION: Nucleic acid sequence of HU-IGKAPPA-LC (with
      N-terminal arginine)

<400> SEQUENCE: 71
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321

<210> SEQ ID NO 72
<211> LENGTH: 990
<212> TYPE: DNA
<213> ORGANISM: Artificial Sequence
<220> FEATURE:
<223> OTHER INFORMATION: Nucleic acid sequence encoding an exemplary
      human IgG1 constant region of the IgG1 G1m3 allotype

<400> SEQUENCE: 72
gcctccacca agggtccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
```

```
atgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctat agcaagctca ccgtggacaa gagcaggtgg      900
cagcagggga acgtcttctc atgctccgtg atgcatgagg ctctgcacaa ccactacacg      960
cagaagagcc tctccctgtc cccgggtaaa                                       990
```

```
<210> SEQ ID NO 73
<211> LENGTH: 19
<212> TYPE: PRT
<213> ORGANISM: Artificial Sequence
<220> FEATURE:
<223> OTHER INFORMATION: Synthetic

<400> SEQUENCE: 73
```

Gly Gly Gly Ser Gly Gly Gly Gly Ser Gly Gly Gly Ser Gly Gly
1               5                   10                  15

Gly Gly Ser

```
<210> SEQ ID NO 74
<211> LENGTH: 9
<212> TYPE: PRT
<213> ORGANISM: Artificial Sequence
<220> FEATURE:
<223> OTHER INFORMATION: Amino acid residues 118-126 of human
      alpha-synuclein

<400> SEQUENCE: 74
```

Val Asp Pro Asp Asn Glu Ala Tyr Glu
1               5

```
<210> SEQ ID NO 75
<211> LENGTH: 330
<212> TYPE: PRT
<213> ORGANISM: Artificial Sequence
<220> FEATURE:
<223> OTHER INFORMATION: Exemplary human IgG1 constant region of the
      IgG1 G1m3 allotype

<400> SEQUENCE: 75
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

-continued

```
Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
        180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
        290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```